US011685768B2

(12) United States Patent
Borodina et al.

(10) Patent No.: US 11,685,768 B2
(45) Date of Patent: *Jun. 27, 2023

(54) METHOD FOR PRODUCTION OF MOTH PHEROMONES IN YEAST

(71) Applicant: Danmarks Tekniske Universitet, Kgs. Lyngby (DK)

(72) Inventors: Irina Borodina, Nivå (DK); Carina Holkenbrink, Kongens Lyngby (DK); Marie Inger Dam, Birkerød (DK); Christer Löfstedt, Lund (SE); Baojian Ding, Södra Sandby (SE); Hong-Lei Wang, Lund (SE)

(73) Assignee: Danmarks Tekniske Universitet, Kongens Lyngby (DK)

( * ) Notice: Subject to any disclaimer, the term of this patent is extended or adjusted under 35 U.S.C. 154(b) by 197 days.

This patent is subject to a terminal disclaimer.

(21) Appl. No.: 15/580,320

(22) PCT Filed: Jun. 24, 2016

(86) PCT No.: PCT/EP2016/064651
§ 371 (c)(1),
(2) Date: Dec. 7, 2017

(87) PCT Pub. No.: WO2016/207339
PCT Pub. Date: Dec. 29, 2016

(65) Prior Publication Data
US 2018/0162916 A1    Jun. 14, 2018

(30) Foreign Application Priority Data
Jun. 26, 2015 (EP) .................................... 15174099

(51) Int. Cl.
*C12P 7/04* (2006.01)
*C07K 14/435* (2006.01)
*C12P 7/24* (2006.01)
*C12P 7/6436* (2022.01)
*C12N 1/16* (2006.01)

(52) U.S. Cl.
CPC .......... *C07K 14/43563* (2013.01); *C12N 1/16* (2013.01); *C12P 7/04* (2013.01); *C12P 7/24* (2013.01); *C12P 7/6436* (2013.01); *C12Y 102/01084* (2015.07); *C12Y 114/19005* (2013.01); *C12Y 203/01086* (2013.01); *Y02P 20/582* (2015.11)

(58) Field of Classification Search
CPC ............... C07K 14/43563; C12N 1/16; C12Y 102/01084; C12Y 114/19005; C12Y 203/01086; C12P 7/6436; C12P 7/24; C12P 7/04; Y02P 20/582
See application file for complete search history.

(56) References Cited

U.S. PATENT DOCUMENTS 5,876,994 A    3/1999 Knipple et al.
9,157,103 B2   10/2015 Hattendorf et al.

FOREIGN PATENT DOCUMENTS

| CN | 102795997 A | 11/2012 |
| WO | WO 03/074715 | 9/2003 |
| WO | WO 2004/031395 | 4/2004 |
| WO | WO 2012/087958 | 6/2012 |
| WO | WO 2013/096082 | 6/2013 |
| WO | 20150171057 A1 | 11/2015 |
| WO | WO 2017/087846 | 5/2017 |

OTHER PUBLICATIONS

Ding et al., Genbank accession No. AID66659, Jun. 30, 2014.*
Hagström et al., Gen Bank accession No. AGP26039, Aug. 3, 2014.*
Duronio, R. J., GenBank accession No. CAA46957, Jul. 24, 1992.*
Hagström et al., PLoS ONE 7(5):e37230, pp. 1-11, published May 16, 2012.*
Rodriguez et al., Nature Chemical Biology 10:259-265, Apr. 2014.*
Fujii et al., Gen Bank accession No. ATF1_YEAST, May 14, 2014.*
Bjostad et al., Journal of Chemical Ecology 10(4):681-691, 1984.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Guo et al., PNAS 101(25):9205-9210, 2004.*
Dujon et al., GenBank accession No. CAG81151, Feb. 27, 2015.*
Suckling, D.M. et al.; "Improving the Pheromone Lure for Diamondback Moth", New Zealand Plant Protection, vol. 55; pp. 182-187; Year: 2002.
Sheng, J. et al., Metabolic engineering of yeast to produce fatty acid-derived biofuels: bottlenecks and solutions, Frontiers in Microbiology; vol. 6, pp. 1-11; Year: 2015.
Rosenfield, C-L. et al., "Structural and functional conservation and divergence among acyl-CoA desaturases of two noctuid species, the corn earworm, *Helicoverpa zea1*, and the cabbage looper, *Trichoplusia ni*", Insect Biochemistry and Molecular Biology, vol. 31, pp. 949-964; Year: 2001.
Lee, S. et al., "Sex pheromone composition if the diamondback moth *Plutella xylostella* in Korea", J. Asia-Pacific Entomol., 8(3), pp. 243-248; Year: 2005.
Iwama, R. et al., "Alcohol dehydrogenases and an alcohol oxidase involved in the assimilation of exogenous fatty alcohols in *Yarrowia lipolytica*", FEMS Yeast Research, vol. 15, No. 3; Year: 2015.

(Continued)

*Primary Examiner* — Delia M Ramirez
(74) *Attorney, Agent, or Firm* — Dinsmore & Shohl LLP; Weston R. Gould

(57) ABSTRACT

The present disclosure relates to methods for production of (Z)-11-hexadecen-1-ol in a yeast cell using desaturases and fatty acyl-CoA reductase. Also disclosed are methods for production of (Z)-11-hexadecenal in a yeast cell. Also disclosed are methods for production of (Z)-11-hexadecen-1-yl acetate in a yeast cell. The disclosure also provides for nucleic acid constructs and yeast cells useful for performing the present methods, as well as to pheromone compositions.

14 Claims, 3 Drawing Sheets

Specification includes a Sequence Listing.

(56) References Cited

OTHER PUBLICATIONS

Heath, R. et al., "Periodicity of Female Sex Pheromone Titer and Release in Heliothis subflexa and H. virescens (Lepidoptera: Noctuidae)", Annals of the Entomological Society of America, 84:2; pp. 182-189; Year: 1991.
Gatter, M.; "A newly identified fatty alcohol oxidase gene is mainly responsible for the oxidation of long-chain x-hydroxy fatty acids in Yarrowia lipolytica", FEMS Yeast Res 14, 858-872; Year: 2014.
Ando, T. et al.; "LepidopteranSex Pheromone, Topics in Current Chemistry"; 239: pp. 51-96; Year: 2004.
Alfaro et al.: Optimization of pheromone dispenser density for managing the rice striped stem borer, Chilo suppressalis (Walker), by mating disruption. Crop Protection. 28:567-572, 2009.
Angerer et al.: "The LYR protein subunit NB4M/NDUFA6 of mitochondrial complex I anchors an acyl carrier protein and is essential for catalytic activity", PNAS. 111(14), 2014.
Bari: "Development of pheromone mating disruption strategies for the suppression of the artichoke plume moth in artichokes grown on the central coast of California", 2003.
Chen et al.: One-step transformation of the dimorphic yeast Yarrowia lipolvtica. Appl Microbiol Biotechnol. 48(2):232-5, 1997.
Subname: Full=Delta 11 desaturase {ECO: 0000313 EMBL: AG096562.1}, retrieved from EBI accession No. UNIPROT:S4WAY4, Oct. 16, 2013.
Ding: "On the way of making plants smell lige moths—a synthetic biology approach", 2013.
Eizaguirre et al.: "Effects of mating disruption against the Mediterranean corn borer, Sesamia nonagrioides, on the European corn borer Ostrinia nubilalis", Use of pheromones and other semiochemicals in integrated production, IOBC wprs Bulletin vol. 25, 2002.
Ferrell et al., 1972. Reductive and oxidative synthesis of saturated and unsaturated fatty aldehydes, J Lipid Res. 13(1):23-6.).
Gietz et al.: Quick and easy yeast transformation using the LiAc/SS carrier DNA/PEG method, Nat Protoc 2: 35-37, 2007.
Jensen et al., 2014. EasyClone: method for iterative chromosomal integration of multiple genes in Saccharomyces cerevisiae, FEMS Yeast Res. 14(2):238-48.
Kehat: Sex Pheromones: achievements in monitoring and mating disruption of cotton pests in Israel, Achieves of Insect Biochemistry and Physiology. 22:425-431, 1993.
Li et al., 2009. An environmentally benign TEMPO-catalyzed efficient alcohol oxidation system with a recyclable hypervalent iodine (III) reagent andilts facile preparation. Synthesis, 1163-1169a.
Maury et al.: EasyCloneMulti: A Set of Vectors for Simultaneous and Multiple Genomic Integrations in Saccharomyces cerevisiae, PLoS One, 11(3):e0150394, 2016.
Meyer et al., 1994. Acceleration of the Dess-Martin oxidation by water J. Org. Chem., 59, 7549-7552.
Okada et al., 2014. Sodium hypochlorite pentahydrate (NaOCl•5H2O) crystals as an extraordinary oxidant for primary and secondary alcohols. Synlett, 25, 596-598.
Stovicek et al.: "EasyClone 2.0: expanded toolkit of integrative vectors for stable gene expression in industrial Saccharomyces cerevisiae strains", J Ind Microbiol Biotechnol, 42, 1519-31, 2015.
Tamura et al., 2012. Novel [4-Hydroxy-Tempo + NaCl]/SiO2 as a reusable catalyst for aerobic oxidation of alcohols to carbonyls. Synlett, 23, 1397-1407.
Wu et al., 2012. Management of diamondback moth, Pluteila xylostella (Lepidoptera: Piutellidae) by mating disruption. Insect Science 19 (6), 643-648.
Yadav et al., 2004. Recyclable 2nd generation ionic liquids as green solvents for the oxidation of alcohols with hypervalent iodine reagents, Tetrahedron, 60, 2131-2135.
European Search Report of corresponding PCT/EP2016/064651 dated Sep. 20, 2016.
Bao-Jian Ding et al, "A Plant Factory for moth pheromone production," Nature Communications, vol. 5, Feb. 25, 2014, XP055227342.
Asa K. Hagstrom et al, "A moth pheromone brewery: production of (Z)-11-hexadecenol by heterologous co-expression of two biosynethic genes from a noctuid moth in a yeast cell factory," Microbial Cell Factories, Biomed Central, GB, vol. 12, No. 1, Dec. 13, 2013, p. 125.
Subname: Uniprot; Oct. 29, 2014; XP002750785.
Dunkelblum et al.: "Identification of the sex pheromone of the cotton bollworm, Heliothis armigera, in Israel", Phytoparasitica 8, 209-211 Year: 1980.
Fujii et al.: "Molecular Cloning, Sequence Analysis, and Expression of the Yeast Alcohol Acetyltransferase Gene", Applied and Environmental Microbiology, Aug. 1994, p. 2786-2792.
Kehat et al.: "Behavioral responses of male Heliothis armigera (lepidoptera: noctuidae) moths in a flight tunnel to combinations of components identified from female sex pheromone glands", Journal of Insect Behavior, 3(1):75-83, Year: 1990.
Knipple et al.: "Cloning and functional expression of a cDNA encoding a pheromone gland-specific acyl-CoA D11-desaturase of the cabbage looper moth, Trichoplusia ni", Proc. Natl. Acad. Sci. USA, vol. 95, p. 15287-15292, Dec. 1998, Biochemistry.
Knoll et al.: "Biochemical Studies of Three Saccharomyces cerevisiae Acyl-CoA Synthetases, FaaIp, FaaZp, and Faa3p", The Journal of Biological Chemistry, vol. 269, No. 23, Issue of Jun. 10, pp. 16348-16356, Year 1994.
Moto et al.: "Pheromone gland-specific fatty-acyl reductase of the silkmoth, Bombyx mori", 9156-9161, PNAS, Aug. 5, 2003, vol. 100, No. 16.
Nesbitt et al.: (Z)-9-Hexadecenal: a minor component of the female sex pheromone of Heliothis armigera (Hübner) (Lepidoptera, Noctuidae). Entomol. Exp. Appl., 27, 306-308 (Year: 1980).
Zhang et al.: "An overlooked component: (Z)-9-tetradecenal as a sex pheromone in Helicoverpa armigera", J. Insect Physiol., 58, 1209-1216 (Year: 2012).
Roelofs, W. et al., Molecular genetics and evolution of pheromone biosynthesis in Lepidoptera, PNAS, 10016): 9179-9184, Aug. 5, 2003.
Machine English translation of CN102795997A, Jan. 20, 2021.
Zhang, Y. et al., Identification and Expression Profiles of Sex Pheromone Biosynthesis and Transport Related Genes in Spodoptera litura, PLoS ONE 10(10): e0140019, 2015.
Devos et al., Proteins Structure, Function and Genetics, 2000, vol. 41: 98-107.
Whisstock et al., Quarterly Reviews of Biophysics 2003, vol. 36 (3): 307-340.
Kisselev L., Structure, 2002, vol. 10: 8-9.
Rodriguez, G. et al., Expanding ester biosynthesis in Escherichia coli, Nat Chem Biol., 10(4): 259-265, Apr. 2014.
Bjostad, L. et al., Biosynthesis Of Sex Pheromone Components and Glycerolipid Precursors From Sodium [lj4c] Acetate In Redbanded Leafroller Moth, Journal of Chemical Ecology, 10(4): 681-691, 1984.

\* cited by examiner

A

B

METHOD FOR PRODUCTION OF MOTH PHEROMONES IN YEAST

FIELD OF INVENTION

Herein are disclosed methods for production of (Z)-11-hexadecen-1-ol in a yeast cell. Also disclosed are methods for production of (Z)-11-hexadecenal in a yeast cell. Also disclosed are methods for production of (Z)-11-hexadecen-1-yl acetate in a yeast cell. The disclosure also provides for nucleic acid constructs and yeast cells useful for performing the present methods, as well as to pheromone compositions.

BACKGROUND OF INVENTION

Integrated Pest Management (IPM) is expected to play a major role for both increasing the crop yield and for minimizing environmental impact and enabling organic food production. IPM employs alternative pest control methods, such as mating disruption using pheromones, mass trapping using pheromones, beneficial insects, etc.

Pheromones constitute a group of diverse chemicals that insects (like other organisms) use to communicate with individuals of the same species in various contexts, including mate attraction, alarm, trail marking and aggregation. Insect pheromones associated with long-range mate finding are already used in agriculture and forestry applications for monitoring and control of pests, as a safe and environmentally friendly alternative to pesticides.

Pheromones for pest control can be divided up in four categories: sex pheromones, aggregation pheromones, oviposition-deterring pheromones and alarm pheromones. Sex pheromones are the largest product segment accounting for 64.8% of the global IPM pheromones market revenues in 2013. Sex pheromones are widely used for pest monitoring and for pest control by mating disruption (e.g., in apple and peach orchards, in forests) and mass trapping (e.g., protection of tomatoes in green houses). Mating disruption occurs when pheromones are released in small amounts into the air and prevent males from locating females, which leads to the eventual cessation of breeding and collapse of the insect infestation. Aggregation pheromones are used to attract both male and female pests and hence are applied for mass trapping. Mass trapping helps maintain population densities below economic damage threshold when insects are caught using attractive baits.

Application of insect pheromones for pest control became possible only after industrial-scale synthesis of pheromones started at the end of the 1980s. Nevertheless, the prices for chemically synthesized pheromones remain high and present a major barrier for expanding their usage in agriculture and forestry. Another drawback with the chemical production of pheromones is the requirement for toxic chemicals to be used as precursors, catalyzers and solvents, and large amounts of organic waste generated during the purification.

Pheromones are currently produced by complex chemical synthesis-based processes, which make the products prohibitively expensive for widespread use in many of the potential applications in agriculture and forestry.

There are several advantages to biological production methods as compared to chemical production methods. First, all the reactions are carried out by engineered cells at ambient temperatures in fermentation tanks instead of multiple chemical reaction steps requiring different precursors, catalyzers and conditions (often high temperatures and pressures). Moreover, the engineered cells use cheap renewable materials, such as sugars or plant oils, instead of using multiple expensive specialty chemicals as precursors. While chemical reactions often suffer from low specificity, and thus require purification of intermediate compounds and extensive purification of the final product, biological reactions carried out by enzymes are typically very specific and formation of by-products is limited, thereby reducing the usage of organic solvents and other toxic chemicals for purification. Moreover, specific stereo-chemistry, which is often important for pheromone activity, can be very difficult to achieve by chemical methods, while enzymatic methods can take advantage of enzymes specific for one of the cis- or trans-isomers.

Hence, there is a need for biological processes for production of insect pheromones. In addition to lower cost benefits, fermentation processes are inherently less hazardous and more environmentally friendly than chemical synthesis.

SUMMARY OF INVENTION

The invention is as defined in the claims.

Herein is provided a method for production of (Z)-11-hexadecen-1-ol in a yeast cell, said method comprising the steps of:

i) providing a yeast cell capable of synthesising hexadecanoyl-CoA, said yeast cell further capable of expressing:

the *Amyelois transitella* Δ11-desaturase (Atr_Δ11; SEQ ID NO: 2), the *Spodoptera littoralis* Δ11-desaturase (Sl_Δ11; SEQ ID NO: 41), the *Agrotis segetum* Δ11-desaturase (Ase_Δ11; SEQ ID NO: 43), the *Trichoplusia ni* Δ11-desaturase (Tni_Δ11; SEQ ID NO: 45) or a variant thereof having at least 65% homology, such as at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 2), Sl_Δ11 (SEQ ID NO: 41), Ase_Δ11 (SEQ ID NO: 43), or Tni_Δ11 (SEQ ID NO: 45), and an alcohol-forming fatty acyl-CoA reductase (FAR) selected from the group consisting of Har_FAR (SEQ ID NO: 8), Hs_FAR (SEQ ID NO: 16), and Has_FAR (SEQ ID NO: 12), or a variant thereof having at least 75% homology, such as at least 80%, such as at least 85%, such as at least 90%, such as at least 95%, such as 100% homology to Har_FAR (SEQ ID NO: 8), Hs_FAR (SEQ ID NO: 16), or Has_FAR (SEQ ID NO: 12);

ii) expressing said Δ11-desaturase and said FAR from said yeast cell; and iii) incubating said yeast cell in a medium, whereby the Δ11-desaturase is capable of converting at least part of said hexadecanoyl-CoA to (Z)11-hexadecenoyl-CoA; and said FAR is capable of converting at least part of said (Z)11-hexadecenoyl-CoA to (Z)-11-hexadecenol, thereby obtaining (Z)-11-hexadecen-1-ol with a titre of at least 0.2 mg/L.

In another aspect, the invention relates to a method for production of (Z)-11-hexadecenal in a yeast cell, said method comprising the steps of:

i) providing a yeast cell capable of synthesising hexadecanoyl-CoA, said yeast cell further capable of expressing:

the *Amyelois transitella* Δ11-desaturase (Atr_Δ11; SEQ ID NO: 2), the *Spodoptera littoralis* Δ11-desaturase (Sl_Δ11; SEQ ID NO: 41), the *Agrotis segetum* Δ11-desaturase (Ase_Δ11; SEQ ID NO: 43), the *Trichoplusia ni* Δ11-desaturase (Tni_Δ11; SEQ ID NO: 45) or a variant thereof having at least 65% homology, such as at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 2), Sl_Δ11 (SEQ ID NO: 41), Ase_Δ11 (SEQ ID NO: 43), or Tni_Δ11 (SEQ ID NO: 45), and an aldehyde-forming fatty acyl-CoA reductase (FAR');

ii) expressing said Δ11-desaturase and said FAR' from said yeast cell; and iii) incubating said yeast cell in a medium, whereby the Δ11-desaturase converts at least part of said hexadecanoyl-CoA to (Z)11-hexadecenoyl-CoA; and said FAR' converts at least part of said (Z)-11-hexadecenoyl-CoA to (Z)-11-hexadecenal, thereby obtaining (Z)-11-hexadecenal.

In yet another aspect, the invention relates to (Z)-11-hexadecen-1-ol obtainable by the methods disclosed herein.

In yet another aspect, the invention relates to (Z)-11-hexadecenal obtainable by the methods disclosed herein.

In yet another aspect, the invention relates to (Z)-11-hexadecen-1-yl acetate obtainable by the methods disclosed herein.

In yet another aspect, the invention relates to a pheromone composition comprising (Z)-11-hexadecenol, (Z)-11-hexadecenal or (Z)-11-hexadecen-1-yl acetate obtainable by the methods disclosed herein.

In yet another aspect, the invention relates to the use of a pheromone composition as defined herein for monitoring the presence of pest and/or disrupting the mating of pest.

In yet another aspect, the invention relates to a method of monitoring the presence of pest or disrupting the mating of pest, said method comprising the steps of:

i) producing (Z)-11-hexadecenol and optionally (Z)-11-hexadecenal and/or (Z)-11-hexadecen-1-yl acetate by the present methods, ii) formulating said (Z)-11-hexadecenol and optionally (Z)-11-hexadecenal and/or (Z)-11-hexadecen-1-yl acetate thus obtained into a pheromone composition, and iii) employing said pheromone composition as an integrated pest management composition.

In yet another aspect, the invention relates to a nucleic acid construct comprising one or more of:

a nucleic acid sequence identical to or having at least 80% homology to SEQ ID NO: 1, SEQ ID NO: 40, SEQ ID NO: 42 or SEQ ID NO: 44; and/or a nucleic acid sequence identical to or having at least 90% homology to SEQ ID NO: 7, SEQ ID NO: 11 or SEQ ID NO: 15; and/or a nucleic acid sequence identical to or having at least 65% homology to SEQ ID NO: 34 or at least 65% homology to SEQ ID NO: 36; and/or a nucleic acid sequence identical to or having at least 65% homology to SEQ ID NO: 38.

In yet another aspect, the invention relates to a yeast cell comprising one or more of:

a nucleic acid sequence identical to or having at least 80% homology to SEQ ID NO: 1, SEQ ID NO: 40, SEQ ID NO: 42 or SEQ ID NO: 44; and/or a nucleic acid sequence identical to or having at least 90% homology to SEQ ID NO: 7, SEQ ID NO: 11 or SEQ ID NO: 15; and/or a nucleic acid sequence identical to or having at least 65% homology to SEQ ID NO: 34 or at least 65% homology to SEQ ID NO: 36; and/or a nucleic acid sequence identical to or having at least 65% homology to SEQ ID NO: 38.

In yet another aspect, the invention relates to a yeast cell capable of synthesising hexadecanoyl-CoA, said yeast cell further capable of expressing:

the *Amyelois transitella* Δ11-desaturase (Atr_Δ11; SEQ ID NO: 2), the *Spodoptera littoralis* Δ11-desaturase (Sl_Δ11; SEQ ID NO: 41), the *Agrotis segetum* Δ11-desaturase (Ase_Δ11; SEQ ID NO: 43), the *Trichoplusia ni* Δ11-desaturase (Tni_Δ11; SEQ ID NO: 45) or a variant thereof having at least 65% homology, such as at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 2), Sl_Δ11 (SEQ ID NO: 41), Ase_Δ11 (SEQ ID NO: 43), or Tni_Δ11 (SEQ ID NO: 45), and an alcohol-forming fatty acyl-CoA reductase (FAR) selected from the group consisting of Har_FAR (SEQ ID NO: 8), Hs_FAR (SEQ ID NO: 16), and Has_FAR (SEQ ID NO: 12), or a variant thereof having at least 75% homology, such as at least 80%, such as at least 85%, such as at least 90%, such as at least 95%, such as 100% homology to Har_FAR (SEQ ID NO: 8), Hs_FAR (SEQ ID NO: 16), or Has_FAR (SEQ ID NO: 12).

In yet another aspect, the invention relates to a yeast cell capable of synthesising hexadecanoyl-CoA, said yeast cell further capable of expressing:

the *Amyelois transitella* Δ11-desaturase (Atr_Δ11; SEQ ID NO: 2), the *Spodoptera littoralis* Δ11-desaturase (Sl_Δ11; SEQ ID NO: 41), the *Agrotis segetum* Δ11-desaturase (Ase_Δ11; SEQ ID NO: 43), the *Trichoplusia ni* Δ11-desaturase (Tni_Δ11; SEQ ID NO: 45) or a variant thereof having at least 65% homology, such as at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 2), Sl_Δ11 (SEQ ID NO: 41), Ase_Δ11 (SEQ ID NO: 43), or Tni_Δ11 (SEQ ID NO: 45), and a fatty acyl-CoA reductase (FAR).

In yet another aspect, the invention relates to a kit of parts comprising a yeast cell and/or a nucleic acid construct as disclosed herein, and instructions for use.

DEFINITIONS

Figure 1:
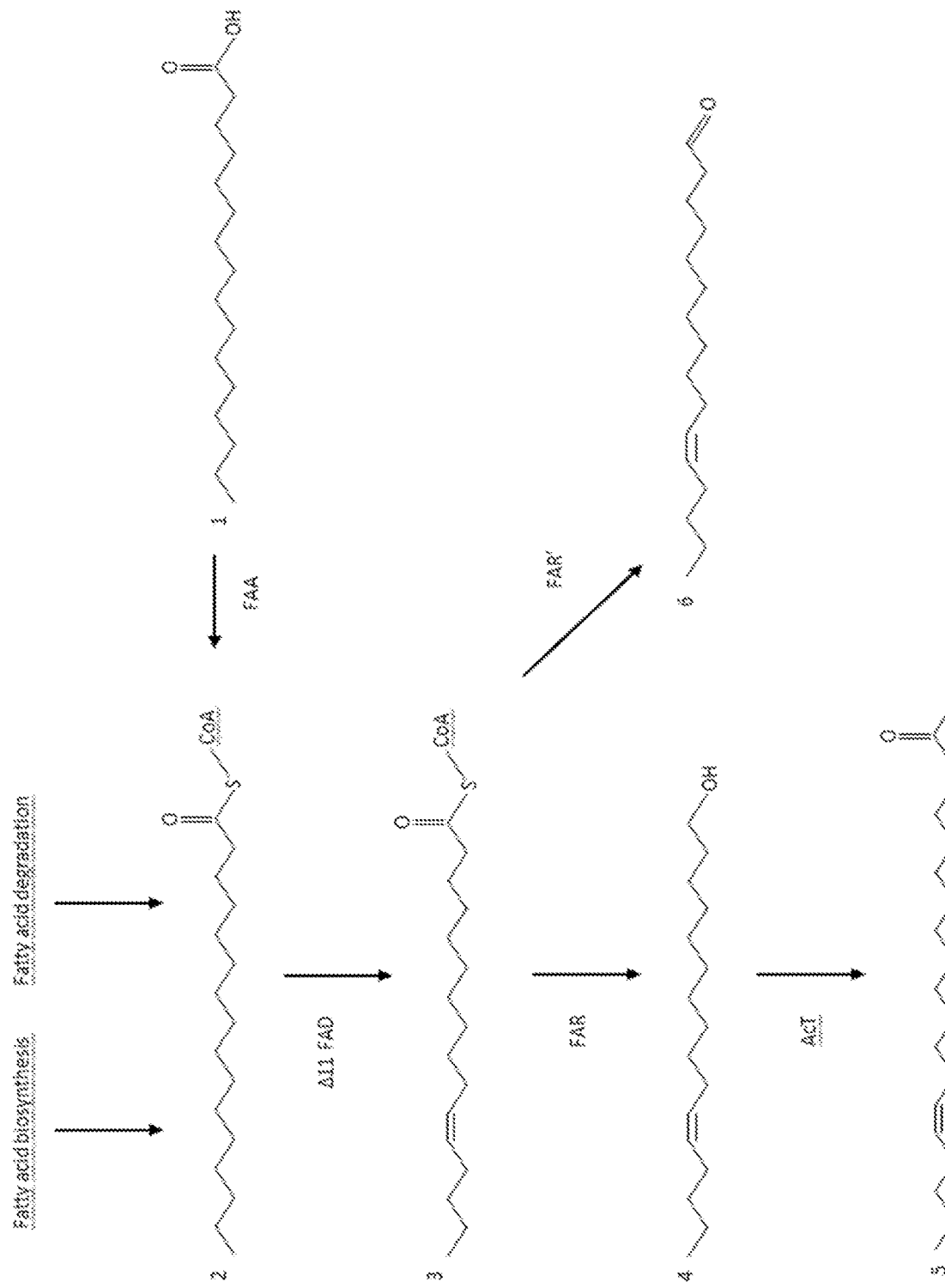
FIG. 1. Heterologous (Z)-11-hexadecen-1-ol pathway. FAA: Fatty acyl CoA synthetase, Δ11 FAD: Δ11-fatty-acyl CoA desaturase, FAR: alcohol-forming fatty acyl-CoA reductase; FAR': aldehyde-forming fatty acyl-CoA reductase, AcT: acetyltransferase; 1: palmitic acid, 2: hexadecanoyl-CoA, 3: (Z)-11-hexadecenoyl-CoA, 4: (Z)-11-hexadecen-1-ol, 5: (Z)-11-hexadecen-1-yl-acetate, 6: (Z)-11-hexadecenal.

Biopesticide: the term 'biopesticide' is a contraction of 'biological pesticide' and refers to several types of pest management intervention: through predatory, parasitic, or chemical relationships. In the EU, biopesticides have been defined as "a form of pesticide based on micro-organisms or natural products". In the US, they are defined by the EPA as "including naturally occurring substances that control pests (biochemical pesticides), microorganisms that control pests (microbial pesticides), and pesticidal substances produced by plants containing added genetic material (plant-incorporated protectants) or PIPs". The present disclosure relates more particularly to biopesticides comprising natural products or naturally occurring substances. They are typically created by growing and concentrating naturally occurring organisms and/or their metabolites including bacteria and other microbes, fungi, nematodes, proteins, etc. They are often considered to be important components of integrated pest management (IPM) programmes, and have received much practical attention as substitutes to synthetic chemical plant protection products (PPPs). The Manual of Biocontrol Agents (2009: formerly the Biopesticide Manual) gives a review of the available biological insecticide (and other biology-based control) products.

Pest: as used herein, the term 'pest' shall refer to an organism, in particular an animal, detrimental to humans or human concerns, in particular in the context of agriculture or livestock production. A pest is any living organism which is invasive or prolific, detrimental, troublesome, noxious, destructive, a nuisance to either plants or animals, human or human concerns, livestock, human structures, wild ecosystems etc. The term often overlaps with the related terms vermin, weed, plant and animal parasites and pathogens. It is possible for an organism to be a pest in one setting but beneficial, domesticated or acceptable in another.

DETAILED DESCRIPTION OF THE INVENTION

The present disclosure relates to methods for producing moth pheromones in a yeast cell, in particular (Z)-11-hexadecen-1-ol, (Z)-11-hexadecenal, and (Z)-11-hexadecen-1-yl acetate, which are components of the insect sex pheromone in large cabbage-heart caterpillar *Crocidolomia binotalis*, diamond back moth *Plutella xylostella*, cabbage moth *Mamestra brassicae*, corn stalk borer *Sesamia nonagrioides*, artichoke plume moth *Platyptilia carduidactyla*, cotton boolworm *Helicoverpa armigera*, stem borer *Chilo suppressalis* and other moths. The inventors have been able to obtain surprisingly high titres of (Z)-11-hexadecen-1-ol using the methods described herein.

Production of (Z)-11-hexadecen-1-ol

Herein are disclosed methods for producing (Z)-11-hexadecen-1-ol from a yeast cell. The inventors have designed a heterologous pathway which is outlined in FIG. 1 by way of example. Hexadecanoyl-CoA is a native fatty acid intermediate in fatty acid metabolism. Hexadecanoyl-CoA is converted to (Z)-11-hexadecenoyl-CoA by a Δ11-fatty acyl desaturase (Δ11 FAD), which in turn is converted to (Z)-11-hexadecen-1-ol by an alcohol-forming fatty acyl-CoA reductase (FAR).

In a first aspect, the present disclosure thus relates to a method for production of (Z)-11-hexadecen-1-ol in a yeast cell, said method comprising the steps of:
i) providing a yeast cell capable of synthesising hexadecanoyl-CoA, said yeast cell further capable of expressing:
the *Amyelois transitella* Δ11-desaturase (Atr_Δ11; SEQ ID NO: 2), the *Spodoptera littoralis* Δ11-desaturase (Sl_Δ11; SEQ ID NO: 41), the *Agrotis segetum* Δ11-desaturase (Ase_Δ11; SEQ ID NO: 43), the *Trichoplusia ni* Δ11-desaturase (Tni_Δ11; SEQ ID NO: 45) or a variant thereof having at least 65% homology, such as at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 2), Sl_Δ11 (SEQ ID NO: 41), Ase_Δ11 (SEQ ID NO: 43), or Tni_Δ11 (SEQ ID NO: 45), and
an alcohol-forming fatty acyl-CoA reductase (FAR) selected from the group consisting of Har_FAR (SEQ ID NO: 8), Hs_FAR (SEQ ID NO: 16), and Has_FAR (SEQ ID NO: 12), or a variant thereof having at least 75% homology, such as at least 80%, such as at least 85%, such as at least 90%, such as at least 95%, such as 100% homology to Har_FAR (SEQ ID NO: 8), Hs_FAR (SEQ ID NO: 16), or Has_FAR (SEQ ID NO: 12);
ii) expressing said Δ11-desaturase and said FAR from said yeast cell; and
iii) incubating said yeast cell in a medium,
whereby
the Δ11-desaturase is capable of converting at least part of said hexadecanoyl-CoA to (Z)11-hexadecenoyl-CoA; and
said FAR is capable of converting at least part of said (Z)11-hexadecenoyl-CoA to (Z)-11-hexadecenol,
thereby obtaining (Z)-11-hexadecen-1-ol with a titre of at least 0.2 mg/L.

Accordingly, the present disclosure provides a method for production of (Z)-11-hexadecen-1-ol in a yeast cell, said method comprising the steps of:
i) providing a yeast cell capable of synthesising hexadecanoyl-CoA, said yeast cell further capable of expressing:
a Δ11-desaturase selected from the group consisting of the *Amyelois transitella* Δ11-desaturase (Atr_Δ11; SEQ ID NO: 2), the *Spodoptera littoralis* Δ11-desaturase (Sl_Δ11; SEQ ID NO: 41), the *Agrotis segetum* Δ11-desaturase (Ase_Δ11; SEQ ID NO: 43) and the *Trichoplusia ni* Δ11-desaturase (Tni_Δ11; SEQ ID NO: 45) or a variant thereof having at least 65% homology, such as at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 2), Sl_Δ11 (SEQ ID NO: 41), Ase_Δ11 (SEQ ID NO: 43), or Tni_Δ11 (SEQ ID NO: 45), and an alcohol-forming fatty acyl-CoA reductase (FAR) selected from the group consisting of Har_FAR (SEQ ID NO: 8), Hs_FAR (SEQ ID NO: 16), and Has_FAR (SEQ ID NO: 12), or a variant thereof having at least 75% homology, such as at least 80%, such as at least 85%, such as at least 90%, such as at least 95%, such as 100% homology to Har_FAR (SEQ ID NO: 8), Hs_FAR (SEQ ID NO: 16), or Has_FAR (SEQ ID NO: 12);

ii) expressing said Δ11-desaturase and said FAR from said yeast cell; and iii) incubating said yeast cell in a medium, whereby the Δ11-desaturase is capable of converting at least part of said hexadecanoyl-CoA to (Z)11-hexadecenoyl-CoA; and said FAR is capable of converting at least part of said (Z)11-hexadecenoyl-CoA to (Z)-11-hexadecenol, thereby obtaining (Z)-11-hexadecen-1-ol with a titre of at least 0.2 mg/L.

Yeast Cell

In the first step of the present method, a yeast cell is provided capable of synthesising hexadecanoyl-CoA.

Any yeast cell capable of synthesising hexadecanoyl-CoA can be used for producing (Z)-11-hexadecen-1-ol as described herein.

In some embodiments, the genus of said yeast is selected from *Saccharomyces, Pichia, Yarrowia, Kluyveromyces, Candida, Rhodotorula, Rhodosporidium, Cryptococcus, Trichosporon* and *Lipomyces*. In some embodiments, the genus of said yeast is *Saccharomyces* or *Yarrowia*.

The yeast cell may be selected from the group consisting of *Saccharomyces cerevisiae, Pichia pastoris, Kluyveromyces marxianus, Cryptococcus albidus, Lipomyces lipofera, Lipomyces starkeyi, Rhodosporidium toruloides, Rhodotorula glutinis, Trichosporon pullulan* and *Yarrowia lipolytica*. In preferred embodiments, the yeast cell is a *Saccharomyces cerevisiae* cell or a *Yarrowia lipolytica* cell.

Fatty Acyl-CoA Synthetase (FAA) (EC 2.3.1.86)

The terms 'fatty acyl-CoA synthetase', 'fatty acyl-CoA synthase' and 'FAA' will be used herein interchangeably.

Hexadecanoyl-CoA is a key intermediate in fatty acid biosynthesis, and it can also be synthesized as an intermediate of lipid degradation. Biosynthesis of hexadecanoyl-CoA can be enhanced by overexpression of genes involved in lipid biosynthesis, such as fatty acid synthases of type I or type II, and/or by overexpression of acetyl-CoA carboxylase, or by improving the supply of acetyl-CoA precursor. Hexadecanoyl-CoA can also be formed via fatty acyl-CoA synthetase from hexadecanoic acid (palmitic acid), which is either supplied in the broth or is synthesized by thioesterase intracellularly. FAA activity is normally present in organisms which are capable of metabolising fatty acids. It may be encoded by several, redundant enzymes. Thus in some embodiments, the yeast cell is further capable of expressing an FAA. The nucleic acid encoding said FAA activity in the yeast cell may be naturally present in the genome of said yeast cell, or it may be introduced by genetic engineering or genome editing. Thus in some embodiments the FAA activity is encoded by introduction of a heterologous nucleic acid in the yeast cell. The heterologous nucleic acid encoding said FAA may be codon-optimised, or may comprise features that can help improve the FAA activity. For example, the heterologous nucleic acid may be modified so as to encode a modified FAA. Such modifications include, but are not limited to, the introduction of localisation signals, gain-of-function or loss-of-function mutations, fusion of the protein to a marker or a tag such as fluorescent tag, insertion of an inducible promoter, introduction of modifications conferring increased stability and/or half-life.

The introduction of the heterologous nucleic acid encoding the FAA activity can be performed by methods known in the art. The skilled person will recognise that such methods include, but are not limited to: cloning and homologous recombination-based methods. Cloning methods may involve the design and construction of a plasmid in an organism such as *Escherichia coli*. The plasmid may be an integrative or a non-integrative vector. Cloning-free methods comprise homologous recombination-based methods such as adaptamer-mediated PCR or gap repair. Such methods often result in integration of the heterologous nucleic acid in the genome of the yeast cell.

In one embodiment, the FAA is Sc_FAA1 (SEQ ID NO: 35) or Yl_FAA (SEQ ID NO: 37), or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 35) or Yl_FAA (SEQ ID NO: 37). Thus in one embodiment, the yeast cell is a *S. cerevisiae* cell and the FAA is Sc_FAA1 (SEQ ID NO:35) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 35). In another embodiment, the yeast cell is a *Y. lipolytica* cell and the FAA is Yl_FAA (SEQ ID NO: 37) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Yl_FAA (SEQ ID NO: 37). In another embodiment, the yeast cell is a *S. cerevisiae* cell and the FAA is Yl_FAA (SEQ ID NO: 37) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Yl_FAA (SEQ ID NO: 37). In yet another embodiment, the yeast cell is a *Y. lipolytica* cell and the FAA is Sc_FAA1 (SEQ ID NO:35) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 35).

In some embodiments, the FAA is Sc_FAA2 (SEQ ID NO: 47).

Δ11-Fatty Acyl Desaturase (Δ11 FAD) (EC 1.14.19.5)

In the present disclosure, the terms 'Δ11-fatty acyl-CoA desaturase', 'Δ11-desaturase' 'Δ11-fatty acyl desaturase' and 'Δ11 FAD' will be used interchangeably and all refer to the EC enzyme having an EC number 1.14.19.5.

In the present method, the yeast cell is further capable of expressing a Δ11 fatty acyl desaturase (Δ11 FAD) which can catalyse the conversion of at least part of the hexadecanoyl-CoA into (Z)-11-hexadecenoyl-CoA (FIG. 1). The inventors have found that the Δ11-desaturase from *Amyelois transitella* (Atr Δ11; SEQ ID NO: 2) or a variant thereof having at least 70% homology to Atr_Δ11 is well suited for catalyzing this step. In some embodiments, the Δ11 FAD has at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Atr_Δ11 (SEQ ID NO: 2).

Another suitable Δ11-desaturase is the *Spodoptera littoralis* Δ11-desaturase (Sl_Δ11; SEQ ID NO: 41) or a variant thereof having at least 70% homology to Atr_Δ11. In some embodiments, the Δ11 FAD has at least 70% homology, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Sl_Δ11 (SEQ ID NO: 41).

In other embodiments, the Δ11-desaturase is the *Agrotis segetum* Δ11-desaturase (Ase_Δ11; SEQ ID NO: 43) or a variant thereof having at least 70% homology to Atr_Δ11. In some embodiments, the Δ11 FAD has at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Ase_Δ11 (SEQ ID NO: 43).

In other embodiments, the Δ11-desaturase is the *Trichoplusia ni* Δ11-desaturase (Tni_Δ11; SEQ ID NO: 45) or a variant thereof having at least 70% homology to Atr_Δ11. In some embodiments, the Δ11 FAD has at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Tni_Δ11 (SEQ ID NO: 45).

In some embodiments, the Δ11 FAD can catalyse the conversion of all of the hexadecanoyl-CoA produced in the previous biosynthetic step into (Z)-11-hexadecenoyl-CoA.

Alcohol-Forming Fatty Acyl-CoA Reductase (EC 1.2.1.84)

The terms 'alcohol-forming fatty acyl-CoA reductase', 'fatty acyl-CoA reductase' and 'FAR' will be used herein interchangeably.

The next step in the biosynthesis pathway of (Z)-11-hexadecen-1-ol is the conversion of at least part of the (Z)-11-hexadecenoyl-CoA to (Z)-11-hexadecen-1-ol by an alcohol-forming fatty acyl-CoA reductase (FAR). The FARs capable of catalyzing this conversion can catalyse two consecutive reduction reactions; first, the fatty acyl-CoA is reduced to a fatty aldehyde; second, the fatty aldehyde is further reduced into a fatty alcohol.

The FARs capable of catalyzing such reaction are alcohol-forming fatty acyl-CoA reductases with an EC number 1.2.1.84.

In some embodiments, the FAR is selected from the group consisting of Har_FAR (SEQ ID NO: 8, FAR from *Helicoverpa armigera*), Hs_FAR (SEQ ID NO: 16, FAR from *Heliothis subflexa*), and Has_FAR (SEQ ID NO: 12, FAR from *Helicoverpa assulta*), or a variant thereof having at least 75% homology.

In one embodiment, the FAR is Har_FAR (SEQ ID NO: 8, FAR from *Helicoverpa armigera*) or a variant thereof having at least 75% homology to Har_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Har_FAR (SEQ ID NO: 8).

In another embodiment, the FAR is Hs_FAR (SEQ ID NO: 16, FAR from *Heliothis subflexa*), or a variant thereof having at least 75% homology to Hs_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Hs_FAR (SEQ ID NO: 16).

In yet another embodiment, the FAR is Has_FAR (SEQ ID NO: 12, FAR from *Helicoverpa assulta*), or a variant thereof having at least 75% homology to Has_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Has_FAR.

In some embodiments, the FAR can catalyse the conversion of all of the (Z)-11-hexadecenoyl-CoA produced in the previous biosynthetic step into (Z)-11-hexadecenol.

The yeast cell provided herein is preferably capable of synthesising hexadecanoyl-CoA and is further capable of expressing a Δ11-desaturase and a FAR as described above.

In some embodiments, expression of the Δ11-desaturase and/or of the FAR can be induced, for example if the genes encoding these enzymes are under the control of inducible promoters, as is known in the art. The yeast cell is incubated under suitable conditions, such as in an appropriate medium and at an appropriate temperature as is known to a person of skill in the art. Suitable media supporting yeast growth are known in the art and include, but are not limited to: undefined, complete media such as YEPD (or YPD, Yeast Extract Peptone Dextrose); defined, complete medium such as SC (Synthetic Complete); defined, drop-out medium such as SD (Synthetic Dextrose) lacking one or more elements such as an amino acid or an inducer; or mineral medium, consisting of salts, vitamins and a carbon source, and others.

Titre

Herein are disclosed methods to produce (Z)-11-hexadecen-1-ol with a titre of at least 0.2 mg/L. In some embodiments, the titre of (Z)-11-hexadecen-1-ol produced by the present methods is at least 0.25 mg/L, such as at least 0.3 mg/L, such as at least 0.4 mg/L, such as at least 0.5 mg/L, such as at least 0.75 mg/L, such as at least 1 mg/L, such as at least 1.5 mg/L, such as at least 2.5 mg/L, such as at least 5.0 mg/L, such as at least 10 mg/L, such as at least 15 mg/L, such as at least 20 mg/L, such as 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L or more.

Methods for determining the titer are known in the art.

In one embodiment, the Δ11-desaturase is Atr_Δ11 as set forth in SEQ ID NO: 2 or a variant thereof having at least 70% homology to Atr_Δ11 and the FAR is Har_FAR as set forth in SEQ ID NO: 8 or a variant thereof having at least 75% homology to Har_FAR. In a particular embodiment, the variant of Har_FAR is as set forth in SEQ ID NO: 10.

In one embodiment, the Δ11-desaturase is Atr_Δ11 as set forth in SEQ ID NO: 2 or a variant thereof having at least 70% homology to Atr_Δ11 and the FAR is Hs_FAR as set forth in SEQ ID NO: 16 or a variant thereof having at least 75% homology to Hs_FAR. In a particular embodiment, the variant of Hs_FAR is as set forth in SEQ ID NO: 16.

In one embodiment, the Δ11-desaturase is Atr_Δ11 as set forth in SEQ ID NO: 2 or a variant thereof having at least 70% homology to Atr_Δ11 and the FAR is Has_FAR as set forth in SEQ ID NO: 12 or a variant thereof having at least 75% homology to Has_FAR. In a particular embodiment, the variant of Has_FAR is as set forth in SEQ ID NO: 12.

In another embodiment, the Δ11-desaturase is Ase_Δ11 as set forth in SEQ ID NO: 43 or a variant thereof having at least 70% homology to Ase_Δ11 and the FAR is Har_FAR as set forth in SEQ ID NO: 8 or a variant thereof having at least 75% homology to Har_FAR. In a particular embodiment, the variant of Har_FAR is as set forth in SEQ ID NO: 10.

In another embodiment, the Δ11-desaturase is SI_Δ11 as set forth in SEQ ID NO: 41 or a variant thereof having at least 70% homology to SI_Δ11 and the FAR is Har_FAR as set forth in SEQ ID NO: 8 or a variant thereof having at least 75% homology to Har_FAR. In a particular embodiment, the variant of Har_FAR is as set forth in SEQ ID NO: 10.

In another embodiment, the Δ11-desaturase is Tni_Δ11 as set forth in SEQ ID NO: 45 or a variant thereof having at least 70% homology to Tni_Δ11 and the FAR is Har_FAR as set forth in SEQ ID NO: 45 or a variant thereof having at least 75% homology to Har_FAR. In a particular embodiment, the variant of Har_FAR is as set forth in SEQ ID NO: 10.

Production of (Z)-11-hexadecen-1-yl acetate

While the present disclosure provides methods for producing (Z)-11-hexadecenol, it may be of interest to further convert said (Z)-11-hexadecen-1-ol to the corresponding acetate, i.e. (Z)-11-hexadecen-1-yl acetate. Thus in some embodiments, the present method further comprises the step of converting at least part of the (Z)-11-hexadecen-1-ol to (Z)-11-hexadecen-1-yl acetate.

In some embodiments, this is done by further expressing an acetyltransferase (AcT, EC 2.3.1.84) or overexpressing a native acetyltransferase from said yeast cell, wherein said acetyltransferase is capable of converting at least part of the (Z)-11-hexadecen-1-ol into (Z)-11-hexadecen-1-yl acetate, thereby further producing (Z)-11-hexadecen-1-yl acetate.

In the present disclosure, the terms 'acetyltransferase', 'alcohol O-acetyltransferase' and 'AcT' will be used interchangeably.

In other embodiments, the conversion of at least part of the (Z)-11-hexadecen-1-ol to (Z)-11-hexadecen-1-yl acetate is done chemically. The skilled person knows how to convert at least part of the (Z)-11-hexadecen-1-ol to (Z)-11-hexadecen-1-yl acetate. For example, acetyl chloride can be added to the (Z)-11-hexadecen-1-ol and incubated at room temperature after mixing.

In some embodiments, the acetyltransferase is the AcT of SEQ ID NO: 39 (Atf1, the S. cerevisiae AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 39.

In some embodiments, (Z)-11-hexadecen-1-yl acetate is produced with a titre of at least 0.2 mg/L. In some embodiments, the titre of (Z)-11-hexadecen-1-yl acetate produced by the present methods is at least 0.25 mg/L, such as at least 0.3 mg/L, such as at least 0.4 mg/L, such as at least 0.5 mg/L, such as at least 0.75 mg/L, such as at least 1 mg/L, such as at least 1.5 mg/L, such as at least 2.5 mg/L, such as at least 5.0 mg/L, such as at least 10 mg/L, such as at least 15 mg/L, such as at least 20 mg/L, such as 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L or more.

Methods for determining the titre are known in the art.

Nucleic Acid Constructs Encoding Δ11-Desaturase, FAR, FAA, AcT

It will be understood that throughout the present disclosure, the term 'nucleic acid encoding an activity' shall refer to a nucleic acid molecule capable of encoding a peptide, a protein or a fragment thereof having said activity. Such nucleic acid molecules may be open reading frames or genes or fragments thereof. The nucleic acid construct may also be a group of nucleic acid molecules, which together may encode several peptides, proteins or fragments thereof having an activity of interest. The term 'activity of interest' shall refer to one of the following activities: Δ11-desaturase, FAR, FAA and/or AcT activities. The nature of the one or more activity of interest will depend on the nature of the desired product one wishes to obtain with the present methods.

In some embodiments of the present methods, each of the nucleic acids encoding each of the present activities, i.e. Δ11-desaturase, FAR, FAA and/or AcT, may be comprised within the genome of the yeast cell or within a vector comprised within yeast cell.

In some embodiments, each of the nucleic acids encoding each of the present activities may be integrated in the genome of said yeast cell, either because the nucleic acid encodes a native protein, or because it has been integrated therein by genome engineering or genome editing or by crossing yeast cells of different mating types. Methods for integrating a nucleic acid are well known in the art. Thus in some embodiments the activity of interest is encoded by introduction of a heterologous nucleic acid in the yeast cell. The heterologous nucleic acid encoding said activity may be codon-optimised, or may comprise features that can help improve the activity. For example, the heterologous nucleic acid may be modified so as to encode a modified FAA. Such modifications include, but are not limited to, the introduction of localisation signals, gain-of-function or loss-of-function mutations, fusion of the protein to a marker or a tag such as fluorescent tag, insertion of an inducible promoter, introduction of modifications conferring increased stability and/or half-life.

The introduction of the heterologous nucleic acid encoding the activity of interest can be performed by methods known in the art. The skilled person will recognise that such methods include, but are not limited to: cloning and homologous recombination-based methods. Cloning methods may involve the design and construction of a plasmid in an organism such as *Escherichia coli*. The plasmid may be an integrative or a non-integrative vector. Cloning-free methods comprise homologous recombination-based methods such as adaptamer-mediated PCR or gap repair. Such methods often result in integration of the heterologous nucleic acid in the genome of the yeast cell.

The nucleic acids encoding the activities of interest may be present in high copy number.

In some embodiments, the Δ11-desaturase activity is encoded by a nucleic acid sequence identical to or having at least 80% homology to SEQ ID NO: 1, SEQ ID NO: 40, SEQ ID NO: 42 or SEQ ID NO: 44.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 1, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1. In preferred embodiments, the nucleic acid sequence has at least 90% homology to SEQ ID NO: 1.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 40, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 40. In preferred embodiments, the nucleic acid sequence has at least 90% homology to SEQ ID NO: 40.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 42, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 42. In preferred embodiments, the nucleic acid sequence has at least 90% homology to SEQ ID NO: 42.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 44, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 44. In preferred embodiments, the nucleic acid sequence has at least 90% homology to SEQ ID NO: 44.

In some embodiments, the FAR activity is encoded by a nucleic acid sequence identical to or having at least 90% homology to SEQ ID NO: 7, SEQ ID NO: 11 or SEQ ID NO: 15.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 7, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 7. In preferred embodiments, the nucleic acid sequence has at least 97% homology to SEQ ID NO: 7.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 11, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 11. In preferred embodiments, the nucleic acid sequence has at least 96% homology to SEQ ID NO: 11.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 15, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 15. In preferred embodiments, the nucleic acid sequence has at least 97% homology to SEQ ID NO: 15.

In some embodiments, the FAA activity is encoded by a nucleic acid sequence identical to or having at least 65% homology to SEQ ID NO: 34 or at least 65% homology SEQ ID NO: 36.

In some embodiments, the nucleic acid sequence identical to or having at least 65% homology to SEQ ID NO: 34 or SEQ ID NO: 36 has at least 70% homology to SEQ ID NO: 34, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34. In preferred embodiments, the nucleic acid sequence has at least 90% homology to SEQ ID NO: 34.

In some embodiments, the nucleic acid sequence identical to or having at least 65% homology to SEQ ID NO: 34 or 36 has at least 65% homology to SEQ ID NO: 36, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36. In preferred embodiments, the nucleic acid sequence has at least 90% homology to SEQ ID NO: 36.

In some embodiments, the FAA activity is encoded by a nucleic acid sequence identical to or having at least 65% homology to SEQ ID NO: 46, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 46.

In some embodiments, the AcT activity is encoded by a nucleic acid sequence identical to or having at least 65% homology to SEQ ID NO: 38.

In some embodiments, the nucleic acid sequence identical to or having at least 65% homology to SEQ ID NO: 38 has at least 70% homology to SEQ ID NO: 38, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 38. In preferred embodiments, the nucleic acid sequence has at least 90% homology to SEQ ID NO: 38.

It follows that herein is disclosed a method for producing (Z)-11-hexadecen-1-ol in a yeast cell as described above, wherein:
the Δ11-desaturase is encoded by a nucleic acid sequence identical to or having at least 80% homology to SEQ ID NO: 1, SEQ ID NO: 40, SEQ ID NO: 42 or SEQ ID NO: 44; and
FAR is encoded by a nucleic acid sequence identical to or having at least 90% homology to SEQ ID NO: 7, SEQ ID NO: 11 or SEQ ID NO: 15, and
FAA is encoded by a native nucleic acid sequence.

Also disclosed herein is a method for producing (Z)-11-hexadecen-1-ol in a yeast cell as described above, wherein:
The Δ11-desaturase is encoded by a nucleic acid sequence identical to or having at least 80% homology to SEQ ID NO: 1, SEQ ID NO: 40, SEQ ID NO: 42 or SEQ ID NO: 44; and
FAR is encoded by a nucleic acid sequence identical to or having at least 90% homology to SEQ ID NO: 7, SEQ ID NO: 11 or SEQ ID NO: 15, and
FAA is encoded by a nucleic acid sequence identical to or having at least 65% homology to SEQ ID NO: 34 or at least 65% homology to SEQ ID NO: 36.

Also disclosed herein is a method for producing (Z)-11-hexadecen-1-yl acetate and/or (Z)-11-hexadecenol, wherein:
The Δ11-desaturase is encoded by a nucleic acid sequence identical to or having at least 80% homology to SEQ ID NO: 1, SEQ ID NO: 40, SEQ ID NO: 42 or SEQ ID NO: 44; and/or
FAR is encoded by a nucleic acid sequence identical to or having at least 90% homology to SEQ ID NO: 7, SEQ ID NO: 11 or SEQ ID NO: 15; and/or
FAA is encoded by a nucleic acid sequence identical to or having at least 65% homology to SEQ ID NO: 34 or at least 65% homology to SEQ ID NO: 36; and/or
AcT is encoded by a nucleic acid sequence identical to or having at least 65% homology to SEQ ID NO: 38.

Also disclosed herein is a method for producing (Z)-11-hexadecen-1-yl acetate and/or (Z)-11-hexadecenol, wherein:
The Δ11-desaturase is encoded by a nucleic acid sequence identical to or having at least 80% homology to SEQ ID NO: 1, SEQ ID NO: 40, SEQ ID NO: 42 or SEQ ID NO: 44; and
FAR is encoded by a nucleic acid sequence identical to or having at least 90% homology to SEQ ID NO: 7, SEQ ID NO: 11 or SEQ ID NO: 15; and FAA is encoded by a nucleic acid sequence identical to or having at least 65% homology to SEQ ID NO: 34 or at least 65% homology to SEQ ID NO: 36; and AcT is encoded by a nucleic acid sequence identical to or having at least 65% homology to SEQ ID NO: 38.

Production of (Z)-11-hexadecenal

While the present disclosure provides methods for producing (Z)-11-hexadecen-1-ol and/or (Z)-11-hexadecen-1-yl acetate, it may be of interest to further convert said (Z)-11-hexadecen-1-ol to the corresponding aldehyde, i.e. (Z)-11-hexadecenal. Thus in some embodiments, the method may further comprise the step of converting at least part of the (Z)-11-hexadecen-1-ol to (Z)-11-hexadecenal, thereby further producing (Z)-11-hexadecenal.

In some embodiments, the step of converting at least part of the (Z)-11-hexadecen-1-ol to (Z)-11-hexadecenal is a step of chemical conversion. The chemical conversion is based on the oxidation of (Z)-11-hexadecen-1-ol to (Z)-11-hexadecenal. Methods for performing this conversion are known in the art. Preferred methods are environmentally friendly and minimize the amount of hazardous waste.

Thus in some embodiments, the chemical conversion may be metal free, avoiding toxic heavy metal based reagents such as manganese oxides, chromium oxides (Jones ox. PDC, PCC) or ruthenium compounds (TPAP, Ley-Griffith ox.). In some embodiments, the conversion does not involve reactions involving activated dimethyl sulfoxide such as the Swern oxidation or the Pfitzner-Moffat type. Such reactions may involve the stereotypic formation of traces of intensively smelling organic sulfur compounds such as dimethyl sulfide which can be difficult to remove from the target product.

In some embodiments, the method comprises a Dess-Martin reaction (Yadav et al., 2004, Meyer et al., 1994).

In other embodiments, the chemical conversion comprises the oxidation with sodium hypochlorite under aqueous/organic two phase conditions (Okada et al., 2014; Tamura et al., 2012; Li et al., 2009).

In some embodiments, the chemical oxidation can be performed with 1-chlorobenzotriazole in a medium of methylene chloride containing 25% pyridine (Ferrell and Yao, 1972).

Alternatively, the oxidation of (Z)-11-hexadecen-1-ol to (Z)-11-hexadecenal can be performed enzymatically by alcohol dehydrogenases. The skilled person will know how to carry out enzymatic oxidation. For example, enzymatic oxidation can be carried out by contacting purified enzymes, cell extracts or whole cells, with (Z)-11-hexadecenol.

Recovery

It may be desirable to recover the products obtained by the methods disclosed herein. Thus the present methods may comprise a further step of recovering (Z)-11-hexadecenol, (Z)-11-hexadecenal and/or (Z)-11-hexadecen-1-yl-acetate.

In some embodiments, the method comprises a step of recovering (Z)-11-hexadecenol. In other embodiments, the method comprises a step of recovering (Z)-11-hexadecen-1-yl-acetate Methods for recovering the products obtained by the present invention are known in the art and may comprise an extraction with a hydrophobic solvent such as decane, hexane or a vegetable oil.

Production of (Z)-11-hexadecenal

In another aspect, the present disclosure relates to a method for production of (Z)-11-hexadecenal in a yeast cell, said method comprising the steps of:

i) providing a yeast cell capable of synthesising hexadecanoyl-CoA, said yeast cell further capable of expressing:

the *Amyelois transitella* Δ11-desaturase (Atr_Δ11; SEQ ID NO: 2), the *Spodoptera littoralis* Δ11-desaturase (Sl_Δ11; SEQ ID NO: 41), the *Agrotis segetum* Δ11-desaturase (Ase_Δ11; SEQ ID NO: 43), the *Trichoplusia ni* Δ11-desaturase (Tni_Δ11; SEQ ID NO: 45) or a variant thereof having at least 70% homology, such as at least 71% homology, such as at least 72%, such as at least 73%, such as at least 74%, such as at least 75%, such as at least 80%, such as at least 85%, such as at least 90%, such as at least 95%, such as 100% homology to Atr_Δ11 (SEQ ID NO: 2), Sl_Δ11 (SEQ ID NO: 41), Ase_Δ11 (SEQ ID NO: 43), or Tni_Δ11 (SEQ ID NO: 45), and an aldehyde-forming fatty acyl-CoA reductase (FAR');

ii) expressing said Δ11-desaturase and said FAR' from said yeast cell; and iii) incubating said yeast cell in a medium, whereby The Δ11-desaturase converts at least part of said hexadecanoyl-CoA to (Z)11-hexadecenoyl-CoA; and said FAR' converts at least part of said (Z)-11-hexadecenoyl-CoA to (Z)-11-hexadecenal, thereby obtaining (Z)-11-hexadecenal.

Yeast Cell

The present disclosure also relates to methods for producing (Z)-11-hexadecenal. In a first step, a yeast cell is provided capable of synthesising hexadecanoyl-CoA.

Any yeast cell capable of synthesising hexadecanoyl-CoA can be used for producing (Z)-11-hexadecenal as described herein.

In some embodiments, the genus of said yeast is selected from *Saccharomyces, Pichia, Yarrowia, Kluyveromyces, Candida, Rhodotorula, Rhodosporidium, Cryptococcus, Trichosporon* and *Lipomyces*. In some embodiments, the genus of said yeast is *Saccharomyces* or *Yarrowia*.

The yeast cell may be selected from the group consisting of *Saccharomyces cerevisiae, Pichia pastoris, Kluyveromyces marxianus, Cryptococcus albidus, Lipomyces lipofera, Lipomyces starkeyi, Rhodosporidium toruloides, Rhodotorula glutinis, Trichosporon pullulan* and *Yarrowia lipolytica*. In preferred embodiments, the yeast cell is a *Saccharomyces cerevisiae* cell or a *Yarrowia lipolytica* cell.

Fatty Acyl-CoA Synthetase (FAA)

Hexadecanoyl-CoA is a natural intermediate of fatty acid metabolism, it can further be generated from palmitic acid (either added externally or synthesized inside the cells by thioesterase) via conversion into hexadecanoyl-CoA by FAA. FAA activity is normally present in organisms which are capable of metabolising fatty acids. It may be encoded by several, redundant enzymes. Thus in some embodiments, the yeast cell is further capable of expressing an FAA. The nucleic acid encoding said FAA activity in the yeast cell may be naturally present in the genome of said yeast cell, or it may be introduced by genetic engineering or genome editing. Thus in some embodiments the FAA activity is encoded by introduction of a heterologous nucleic acid in the yeast cell. The heterologous nucleic acid encoding said FAA may be codon-optimised, or may comprise features that can help improve the FAA activity. For example, the heterologous nucleic acid may be modified so as to encode a modified FAA. Such modifications include, but are not limited to, the introduction of localisation signals, gain-of-function or loss-of-function mutations, fusion of the protein to a marker or a tag such as fluorescent tag, insertion of an inducible promoter, introduction of modifications conferring increased stability and/or half-life.

The introduction of the heterologous nucleic acid encoding the FAA activity can be performed by methods known in the art. The skilled person will recognise that such methods include, but are not limited to: cloning and homologous recombination-based methods. Cloning methods may involve the design and construction of a plasmid in an organism such as *Escherichia coli*. The plasmid may be an integrative or a non-integrative vector. Cloning-free methods comprise homologous recombination-based methods such as adaptamer-mediated PCR or gap repair. Such methods often result in integration of the heterologous nucleic acid in the genome of the yeast cell.

In one embodiment, the FAA is Sc_FAA1 (SEQ ID NO: 35) or Yl_FAA (SEQ ID NO: 37), or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 35) or Yl_FAA (SEQ ID NO: 37). Thus in one embodiment, the yeast cell is a *S. cerevisiae* cell and the FAA is Sc_FAA1 (SEQ ID NO:35) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 35). In another embodiment, the yeast cell is a *Y. lipolytica* cell and the FAA is Yl_FAA (SEQ ID NO: 37) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Yl_FAA (SEQ ID NO: 37). In another embodiment, the yeast cell is a *S. cerevisiae* cell and the FAA is Yl_FAA (SEQ ID NO: 37) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Yl_FAA (SEQ ID NO: 37). In yet another embodiment, the yeast cell is a *Y. lipolytica* cell and the FAA is Sc_FAA1 (SEQ ID NO:35) or a variant thereof having at least 75% homology, such as at least 80% homology, such as at least 85% homology, such as at least 90% homology, such as at least 91% homology, such as at least 92% homology, such as at least 93% homology, such as at least 94% homology, such as at least 95% homology, such as at least 96% homology, such as at least 97% homology, such as at least 98% homology, such as at least 99% homology, such as 100% homology to Sc_FAA1 (SEQ ID NO: 35).

In some embodiments, the FAA is Sc_FAA2 (SEQ ID NO: 47).

Δ11-Fatty Acyl Desaturase (EC 1.14.19.5)

The yeast cell is further capable of expressing a Δ11-fatty acyl desaturase (Δ11 FAD) which can catalyse the conversion of at least part of the hexadecanoyl-CoA into (Z)-11-hexadecenoyl-CoA. The inventors have found that the Δ11-desaturase from *Amyelois transitella* (Atr_Δ11; SEQ ID NO: 2) or a variant thereof having at least 70% homology to Atr_Δ11 is well suited for catalyzing this step. In some embodiments, the Δ11 FAD has at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Atr_Δ11 (SEQ ID NO: 2).

In some embodiments, the Δ11 FAD has at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Sl_Δ11 (SEQ ID NO: 41).

In some embodiments, the Δ11 FAD has at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Ase_Δ11 (SEQ ID NO: 43).

In some embodiments, the Δ11 FAD has at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Tni_Δ11 (SEQ ID NO: 45).

In some embodiments, the Δ11 FAD can catalyse the conversion of all of the hexadecanoyl-CoA produced in the previous biosynthetic step into (Z)-11-hexadecenoyl-CoA.

Aldehyde-Forming Fatty Acyl-CoA Reductase EC 1.2.1.50 (FAR')

Instead of producing hexadecen-1-ol, at least part of the (Z)-11-hexadecenoyl-CoA can be converted to (Z)-11 hexadecenal by an aldehyde-forming fatty acyl-CoA reductase (FAR'). The enzymes capable of catalyzing this conversion can catalyse one reduction reaction, where the fatty acyl-CoA is reduced to a fatty aldehyde. Such enzymes are aldehyde-forming fatty acyl-CoA reductases, herein also referred to as FAR' or aldehyde-forming FAR, with an EC number 1.2.1.50. They catalyse the following reaction:

long-chain acyl-CoA+NADPH=long-chain aldehyde+NADP++coenzyme A, where the term 'long-chain' designates chains with 16 to 22 carbon atoms.

The yeast cell provided is thus capable of synthesising hexadecanoyl-CoA and is further capable of expressing a Δ11-desaturase and an aldehyde-forming FAR catalysing a one-step reduction as described above. In some embodiments, expression of the Δ11-desaturase and/or of the aldehyde-forming FAR can be induced, for example if the genes encoding these enzymes are under the control of inducible promoters, as is known in the art. The yeast cell is incubated under suitable conditions, such as in an appropriate medium and at an appropriate temperature as is known to a person of skill in the art. Suitable media supporting yeast growth are known in the art and include, but are not limited to: undefined, complete media such as YEPD (or YPD, Yeast Extract Peptone Dextrose), defined, complete medium such as SC (Synthetic Complete), or defined, drop-out medium such as SD (Synthetic Dextrose) lacking one or more elements such as an amino acid or an inducer.

Titre

Herein are disclosed methods to produce (Z)-11-hexadecenal with a titre of at least 0.1 mg/L. In some embodiments, the titre of (Z)-11-hexadecenal produced by the present methods is at least 0.2 mg/L, such as at least 0.25 mg/L, such as at least 0.3 mg/L, such as at least 0.4 mg/L, such as at least 0.5 mg/L, such as at least 0.75 mg/L, such as at least 1 mg/L, such as at least 1.5 mg/L, such as at least 2.5 mg/L, such as at least 5.0 mg/L, such as at least 10 mg/L, such as at least 15 mg/L, such as at least 20 mg/L, such as 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L or more.

Methods for determining the titer are known in the art.

Nucleic Acids Encoding Δ11-Desaturase, FAR', FAA, AcT

In some embodiments of the present method for production of (Z)-11-hexadecenal, each of the nucleic acids encoding each of the present activities, i.e. Δ11-desaturase, FAA or aldehyde-forming FAR, may be comprised within the genome of the yeast cell or within a vector comprised within yeast cell.

In some embodiments, each of the nucleic acids encoding each of the present activities may be integrated in the genome of said yeast cell, either because the nucleic acid encodes a native protein, or because it has been integrated therein by genome engineering or genome editing or by crossing yeast cells of different mating types. Methods for integrating a nucleic acid are well known in the art. Thus in some embodiments the activity of interest is encoded by introduction of a heterologous nucleic acid in the yeast cell. The heterologous nucleic acid encoding said activity may be codon-optimised, or may comprise features that can help improve the activity. For example, the heterologous nucleic acid may be modified so as to encode a modified FAA. Such modifications include, but are not limited to, the introduction of localisation signals, gain-of-function or loss-of-function mutations, fusion of the protein to a marker or a tag such as fluorescent tag, insertion of an inducible promoter, introduction of modifications conferring increased stability and/or half-life.

The introduction of the heterologous nucleic acid encoding the activity of interest can be performed by methods known in the art. The skilled person will recognise that such methods include, but are not limited to: cloning and homologous recombination-based methods. Cloning methods may involve the design and construction of a plasmid in an organism such as *Escherichia coli*. The plasmid may be an integrative or a non-integrative vector. Cloning-free methods comprise homologous recombination-based methods such as adaptamer-mediated PCR or gap repair. Such methods often result in integration of the heterologous nucleic acid in the genome of the yeast cell.

The nucleic acids encoding the activities of interest may be present in high copy number.

In some embodiments, the Δ11-desaturase activity is encoded by a nucleic acid sequence identical to or having at least 80% homology to SEQ ID NO: 1, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1. Preferably, the Δ11-desaturase activity is encoded by a nucleic acid sequence identical to or having at least 90% homology to SEQ ID NO: 1.

In other embodiments, the Δ11-desaturase activity is encoded by a nucleic acid sequence identical to or having at least 80% homology to SEQ ID NO: 40, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 40. Preferably, the Δ11-desaturase activity is encoded by a nucleic acid sequence identical to or having at least 90% homology to SEQ ID NO: 40.

In other embodiments, the Δ11-desaturase activity is encoded by a nucleic acid sequence identical to or having at least 80% homology to SEQ ID NO: 42, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 42. Preferably, the Δ11-desaturase activity is encoded by a nucleic acid sequence identical to or having at least 90% homology to SEQ ID NO: 42.

In other embodiments, the Δ11-desaturase activity is encoded by a nucleic acid sequence identical to or having at least 80% homology to SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 44. Preferably, the Δ11-desaturase activity is encoded by a nucleic acid sequence identical to or having at least 90% homology to SEQ ID NO: 44.

In some embodiments, the FAA activity is encoded by a nucleic acid sequence identical to or having at least 65% homology to SEQ ID NO: 34 or at least 65% homology to SEQ ID NO: 36, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34 or SEQ ID NO: 36.

In some embodiments, the FAA activity is encoded by a nucleic acid sequence identical to or having at least 65% homology to SEQ ID NO: 46, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 46.

It follows that herein is disclosed a method for producing (Z)-11-hexadecenal in a yeast cell as described above, wherein:
The Δ11-desaturase is encoded by a nucleic acid sequence identical to or having at least 80% homology to SEQ ID NO: 1, SEQ ID NO: 40, SEQ ID NO: 42 or SEQ ID NO: 44; and
FAR' is selected from the group consisting of FARs which are able to catalyse a one-step reduction of a fatty acyl-CoA to a fatty aldehyde; and
FAA is encoded by a native nucleic acid sequence.

Also disclosed herein is a method for producing (Z)-11-hexadecen-1-ol in a yeast cell as described above, wherein:
The Δ11-desaturase is encoded by a nucleic acid sequence identical to or having at least 80% homology to SEQ ID NO: 1, SEQ ID NO: 40, SEQ ID NO: 42 or SEQ ID NO: 44; and
FAR' is selected from the group consisting of FARs which are able to catalyse reduction of a fatty acyl-CoA to a fatty aldehyde, and the further reduction of the fatty aldehyde to a fatty alcohol;
FAA is encoded by a nucleic acid sequence identical to or having at least 65% homology to SEQ ID NO: 34 or SEQ ID NO: 36.

In some embodiments, the FAR' is an enzyme with an EC number 1.2.1.50.

Recovery

It may be desirable to recover the products obtained by the methods disclosed herein. Thus the present methods may comprise a further step of recovering (Z)-11-hexadecenol, (Z)-11-hexadecenal and/or (Z)-11-hexadecen-1-yl-acetate.

Methods for recovering the products obtained by the present invention are known in the art and may comprise an extraction with a hydrophobic solvent such as decane, hexane or a vegetable oil.

Nucleic Acid Constructs

The present disclosure also relates to a nucleic acid construct comprising one or more of:
a nucleic acid sequence identical to or having at least 80% homology to SEQ ID NO: 1, SEQ ID NO: 40, SEQ ID NO: 42 or SEQ ID NO: 44; and/or
a nucleic acid sequence identical to or having at least 90% homology to SEQ ID NO: 7, SEQ ID NO: 11 or SEQ ID NO: 15; and/or
a nucleic acid sequence identical to or having at least 65% homology to SEQ ID NO: 34 or at least 65% homology to SEQ ID NO: 36; and/or
a nucleic acid sequence identical to or having at least 65% homology to SEQ ID NO: 38.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 1, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1. In preferred embodiments, the nucleic acid sequence has at least 90% homology to SEQ ID NO: 1.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 40, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 40. In preferred embodiments, the nucleic acid sequence has at least 90% homology to SEQ ID NO: 40.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 42, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 42. In preferred embodiments, the nucleic acid sequence has at least 90% homology to SEQ ID NO: 42.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 44, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 44. In preferred embodiments, the nucleic acid sequence has at least 90% homology to SEQ ID NO: 44.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 7, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 7. In preferred embodiments, the nucleic acid sequence identical to or having at least 90% homology to SEQ ID NO: 7 has at least 97% homology to SEQ ID NO: 7.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 11, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 11. In preferred embodiments, the nucleic acid sequence identical to or having at least 90% homology to SEQ ID NO: 11 has at least 96% homology to SEQ ID NO: 11.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 15, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 15. In preferred embodiments, the nucleic acid sequence identical to or having at least 90% homology to SEQ ID NO: 15 has at least 97% homology to SEQ ID NO: 15.

In some embodiments, the nucleic acid sequence identical to or having at least 65% homology to SEQ ID NO: 34 or SEQ ID NO: 36 has at least 70% homology to SEQ ID NO: 34, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34. In preferred embodiments, the nucleic acid sequence has at least 90% homology to SEQ ID NO: 34.

In some embodiments, the nucleic acid sequence identical to or having at least 65% homology to SEQ ID NO: 34 or SEQ ID NO: 36 has at least 70% homology to SEQ ID NO: 36, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36. In preferred embodiments, the nucleic acid sequence has at least 90% homology to SEQ ID NO: 36.

In some embodiments, the nucleic acid sequence identical to or having at least 65% homology to SEQ ID NO: 38 has at least 70% homology to SEQ ID NO: 38, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 38. In preferred embodiments, the nucleic acid sequence has at least 90% homology to SEQ ID NO: 38.

In some embodiments, the nucleic acid construct comprises:
  a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44; and
  a nucleic acid sequence identical to or having at least 90% homology to SEQ ID NO: 7, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 7.

In some embodiments, the nucleic acid construct comprises:
  a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44; and
  a nucleic acid sequence identical to or having at least 90% homology to SEQ ID NO: 11, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 11.

In some embodiments, the nucleic acid construct comprises:
  a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44; and a nucleic acid sequence identical to or having at least 90% homology to SEQ ID NO: 15, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 15.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44; and a nucleic acid sequence identical to or having at least 90% homology to SEQ ID NO: 7, SEQ ID NO: 11 or SEQ ID NO: 15; and a nucleic acid sequence identical to or having at least 65% homology to SEQ ID NO: 34 or at least 65% homology to SEQ ID NO: 36.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 7, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 7; and a nucleic acid sequence identical to or having at least 65% homology to SEQ ID NO: 34, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 7, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 7; and a nucleic acid sequence identical to or having at least 65% homology to SEQ ID NO: 36, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 11, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 11; and a nucleic acid sequence identical to or having at least 65% homology to SEQ ID NO: 34, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 11, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 11; and a nucleic acid sequence identical to or having at least 65% homology to SEQ ID NO: 36, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 15, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 15; and a nucleic acid sequence identical to or having at least 65% homology to SEQ ID NO: 34, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 15, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 15; and a nucleic acid sequence identical to or having at least 65% homology to SEQ ID NO: 36, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36.

In some embodiments, the nucleic acid construct further comprises a nucleic acid sequence identical to or having at least 65% homology to SEQ ID NO: 38, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 38.

At least one of the one or more nucleic acid sequences may be under the control of an inducible promoter.

In some embodiments, the nucleic acid construct is a vector such as an integrative vector or a replicative vector. In one embodiment, the vector is a high copy replicative vector.

Each of the nucleic acid sequences comprised within the present nucleic acid constructs may be present in multiple copies. In some embodiments, at least one of the nucleic acid sequences is present in at least 2 copies, such as at least 3 copies, such as at least 4 copies, such as at least 5 copies, such as at least 10 copies, such as at least 20 copies, such as at least 30 copies, such as at least 40 copies, such as at least 50 copies, such as at least 60 copies, such as at least 70 copies, such as at least 80 copies, such as at least 90 copies, such as at least 100 copies, such as at least 125 copies, such as at least 150 copies, such as at least 175 copies, such as at least 200 copies. In some embodiments, all of the nucleic acid sequences are present in at least 2 copies, such as at least 3 copies, such as at least 4 copies, such as at least 5 copies, such as at least 10 copies, such as at least 20 copies, such as at least 30 copies, such as at least 40 copies, such as at least 50 copies, such as at least 60 copies, such as at least 70 copies, such as at least 80 copies, such as at least 90 copies, such as at least 100 copies, such as at least 125 copies, such as at least 150 copies, such as at least 175 copies, such as at least 200 copies.

The nucleic acid constructs may also be a PCR product or a synthetic DNA molecule.

Yeast Cell

Also provided herein is a yeast cell that can be used for any of the methods disclosed herein. The yeast cell comprises one or more of:
- a nucleic acid sequence identical to or having at least 80% homology to SEQ ID NO: 1, SEQ ID NO: 40, SEQ ID NO: 42 or SEQ ID NO: 44; and/or
- a nucleic acid sequence identical to or having at least 90% homology to SEQ ID NO: 7, SEQ ID NO: 11 or SEQ ID NO: 15; and/or
- a nucleic acid sequence identical to or having at least 65% homology to SEQ ID NO: 34 or at least 65% homology to SEQ ID NO: 36; and/or
- a nucleic acid sequence identical to or having at least 65% homology to SEQ ID NO: 38.

In some embodiments, the yeast cell comprises:
- a nucleic acid sequence identical to or having at least 80% homology to SEQ ID NO: 1, SEQ ID NO: 40, SEQ ID NO: 42 or SEQ ID NO: 44; and
- a nucleic acid sequence identical to or having at least 90% homology to SEQ ID NO: 7, SEQ ID NO: 11 or SEQ ID NO: 15.

In some embodiments, the yeast cell comprises:
- a nucleic acid sequence identical to or having at least 80% homology to SEQ ID NO: 1, SEQ ID NO: 40, SEQ ID NO: 42 or SEQ ID NO: 44; and
- a nucleic acid sequence identical to or having at least 90% homology to SEQ ID NO: 7, SEQ ID NO: 11 or SEQ ID NO: 15; and
- a nucleic acid sequence identical to or having at least 65% homology to SEQ ID NO: 34, or SEQ ID NO: 36.

In some embodiments, the yeast cell comprises:
- a nucleic acid sequence identical to or having at least 80% homology to SEQ ID NO: 1, SEQ ID NO: 40, SEQ ID NO: 42 or SEQ ID NO: 44; and
- a nucleic acid sequence identical to or having at least 90% homology to SEQ ID NO: 7, SEQ ID NO: 11 or SEQ ID NO: 15; and
- a nucleic acid sequence identical to or having at least 65% homology to SEQ ID NO: 34, or SEQ ID NO: 36; and
- a nucleic acid sequence identical to or having at least 65% homology to SEQ ID NO: 38.

As detailed above, the one or more nucleic acid sequence may be comprised within the genome of said yeast cell or within a nucleic acid construct comprised within said yeast cell. In some embodiments, the yeast cell comprises at least one nucleic acid construct as described above.

Preferably, the yeast cell is capable of synthesising hexadecanoyl-CoA and can be used for producing (Z)-11-hexadecen-1-ol and/or (Z)-11-hexadecenal and/or (Z)-11-hexadecen-1-yl acetate as described herein.

In some embodiments, the genus of said yeast is selected from *Saccharomyces*, *Pichia*, *Yarrowia*, *Kluyveromyces*, *Candida*, *Rhodotorula*, *Rhodosporidium*, *Cryptococcus*, *Trichosporon* and *Lipomyces*. In some embodiments, the genus of said yeast is *Saccharomyces* or *Yarrowia*.

The yeast cell may be selected from the group consisting of *Saccharomyces cerevisiae*, *Pichia pastoris*, *Kluyveromyces marxianus*, *Cryptococcus albidus*, *Lipomyces lipofera*, *Lipomyces starkeyi*, *Rhodosporidium toruloides*, *Rhodotorula glutinis*, *Trichosporon pullulan* and *Yarrowia lipolytica*. In preferred embodiments, the yeast cell is a *Saccharomyces cerevisiae* cell or a *Yarrowia lipolytica* cell.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 1, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1. In preferred embodiments, the nucleic acid sequence has at least 90% homology to SEQ ID NO: 1.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 40, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 40. In preferred embodiments, the nucleic acid sequence has at least 90% homology to SEQ ID NO: 40.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 42, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 42. In preferred embodiments, the nucleic acid sequence has at least 90% homology to SEQ ID NO: 42.

In some embodiments, the nucleic acid sequence identical to or having at least 80% homology to SEQ ID NO: 1, SEQ ID NO: 40, SEQ ID NO: 42 or SEQ ID NO: 44 has at least 81% homology to SEQ ID NO: 44, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 44. In preferred embodiments, the nucleic acid sequence has at least 90% homology to SEQ ID NO: 44.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 7, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 7. In preferred embodiments, the nucleic acid sequence identical to or having at least 90% homology to SEQ ID NO: 7 has at least 97% homology to SEQ ID NO: 7.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 11, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 11. In preferred embodiments, the nucleic acid sequence identical to or having at least 90% homology to SEQ ID NO: 11 has at least 96% homology to SEQ ID NO: 11.

In some embodiments, the nucleic acid sequence identical to or having at least 90% homology to SEQ ID NO: 7, SEQ ID NO: 11 or SEQ ID NO: 15 is a nucleic acid sequence identical to or having at least 90% homology to SEQ ID NO: 15, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 15. In preferred embodiments, the nucleic acid sequence identical to or having at least 90% homology to SEQ ID NO: 15 has at least 97% homology to SEQ ID NO: 15.

In some embodiments, the nucleic acid sequence identical to or having at least 65% homology to SEQ ID NO: 34 or SEQ ID NO: 36 has at least 70% homology to SEQ ID NO: 34, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34. In preferred embodiments, the nucleic acid sequence has at least 90% homology to SEQ ID NO: 34.

In some embodiments, the nucleic acid sequence identical to or having at least 65% homology to SEQ ID NO: 34 or SEQ ID NO: 36 has at least 70% homology to SEQ ID NO: 36, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36. In preferred embodiments, the nucleic acid sequence has at least 90% homology to SEQ ID NO: 36.

In some embodiments, the nucleic acid sequence identical to or having at least 65% homology to SEQ ID NO: 38 has at least 70% homology to SEQ ID NO: 34, such as at least 75%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 38. In preferred embodiments, the nucleic acid sequence has at least 90% homology to SEQ ID NO: 38.

In some embodiments, the nucleic acid construct comprises:
  a nucleic acid sequence identical to or having at least 80% homology to SEQ ID NO: 1, SEQ ID NO: 40, SEQ ID NO: 42 or SEQ ID NO: 44; and
  a nucleic acid sequence identical to or having at least 90% homology to SEQ ID NO: 7, SEQ ID NO: 11 or SEQ ID NO: 15; and
  a nucleic acid sequence identical to or having at least 65% homology to SEQ ID NO: 34 or SEQ ID NO: 36.

In some embodiments, the nucleic acid construct comprises:
  a nucleic acid sequence identical to or having at least 80% homology to SEQ ID NO: 1, SEQ ID NO: 40, SEQ ID NO: 42 or SEQ ID NO: 44 has at least 90% homology to SEQ ID NO: 1, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;
  a nucleic acid sequence identical to or having at least 90% homology to SEQ ID NO: 7, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 7; and
  a nucleic acid sequence identical to or having at least 65% homology to SEQ ID NO: 34, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34.

In some embodiments, the nucleic acid construct comprises:
  a nucleic acid sequence identical to or having at least 80% homology to SEQ ID NO: 1, SEQ ID NO: 40, SEQ ID NO: 42 or SEQ ID NO: 44 has at least 90% homology to SEQ ID NO: 1, SEQ ID NO: 40, SEQ ID NO: 42 or SEQ ID NO: 44 such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 7, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 7; and a nucleic acid sequence identical to or having at least 65% homology to SEQ ID NO: 36, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44 has at least 90% homology to SEQ ID NO: 1, SEQ ID NO: 40, SEQ ID NO: 42 or SEQ ID NO: 44 such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 11, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 11; and a nucleic acid sequence identical to or having at least 65% homology to SEQ ID NO: 34, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44 has at least 90% homology to SEQ ID NO: 1, SEQ ID NO: 40, SEQ ID NO: 42 or SEQ ID NO: 44, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 11, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 11; and a nucleic acid sequence identical to or having at least 65% homology to SEQ ID NO: 36, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44 has at least 90% homology to SEQ ID NO: 1, SEQ ID NO: 40, SEQ ID NO: 42 or SEQ ID NO: 44, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 15, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 15; and a nucleic acid sequence identical to or having at least 65% homology to SEQ ID NO: 34, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 34.

In some embodiments, the nucleic acid construct comprises:

a nucleic acid sequence identical to or having at least 80% homology to SEQ ID NO: 1, SEQ ID NO: 40, SEQ ID NO: 42 or SEQ ID NO: 44 has at least 90% homology to SEQ ID NO: 1, SEQ ID NO: 40, SEQ ID NO: 42 or SEQ ID NO: 44, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 1, SEQ ID NO: 40, SEQ ID NO: 42 or SEQ ID NO: 44;

a nucleic acid sequence identical to or having at least 90% homology to SEQ ID NO: 15, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 15; and a nucleic acid sequence identical to or having at least 65% homology to SEQ ID NO: 36, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 36.

In some embodiments, the nucleic acid construct further comprises a nucleic acid sequence identical to or having at least 65% homology to SEQ ID NO: 38, such as at least 70%, such as at least 71%, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 38.

Pheromone Composition

Also provided herein is a pheromone composition comprising (Z)-11-hexadecenol, (Z)-11-hexadecenal or (Z)-11-hexadecen-1-yl acetate. At least one of the (Z)-11-hexadecenol, (Z)-11-hexadecenal or (Z)-11-hexadecen-1-yl acetate is preferably obtainable by the methods disclosed herein above.

In some embodiments, the pheromone composition comprises (Z)-11-hexadecenol, (Z)-11-hexadecenal and (Z)-11-hexadecen-1-yl acetate, where at least one of the (Z)-11-hexadecenol, (Z)-11-hexadecenal or (Z)-11-hexadecen-1-yl acetate is obtainable by the methods disclosed herein above.

Accordingly, the present methods may further comprise the step of formulating the recovered (Z)-11-hexadecenol, (Z)-11-hexadecenal or (Z)-11-hexadecen-1-yl acetate into a pheromone composition. The present pheromone compositions may be used as integrated pest management products, which can be used in a method of monitoring the presence of pest or in a method of disrupting the mating of pest.

Pheromone compositions as disclosed herein may be used as biopesticides. Such compositions can be sprayed or dispensed on a culture, in a field or in an orchard. They can also, as is known in the art, be soaked e.g. onto a rubber septa, or mixed with other components. This can result in mating disruption, thereby preventing pest reproduction, or it can be used in combination with a trapping device to entrap the pests. Non-limiting examples of pests against which the present pheromone compositions can be used are: cotton bollworm (*Helicoverpa armigera*), striped stemborer (*Chilo suppressalis*), diamond back moth (*Plutella xylostella*), cabbage moth (*Mamestra brassicae*), large cabbage-heart caterpillar (*Crocidolomia binotalis*), European corn stalk borer (*Sesamia nonagrioides*), currant clearwing (*Synanthedon tipuliformis*) and artichoke plume moth (*Platyptilia carduidactylal*). Accordingly, use of the present compositions on a culture can lead to increased crop yield, with substantially no environmental impact.

The relative amounts of the (Z)-11-hexadecenol, (Z)-11-hexadecenal and (Z)-11-hexadecen-1-yl acetate in the present pheromone compositions may vary depending on the nature of the crop and/or of the pest to be controlled; geographical variations may also exist. Determining the optimal relative amounts may thus require routine optimisation.

Examples of compositions used as repellents can be found in Kehat & Dunkelblum, 1993, for *H. armigera*, in Alfaro et al., 2009, for *C. suppressalis*, in Eizaguirre et al., 2002, for *S. nonagrioides*; in Wu et al., 2012, for *P. xylostella*; in Bari et al., 2003, for *P. carduidactyla*

The pheromone composition may thus comprise between 1 and 100% (Z)-11-hexadecenol, between 1 and 100% (Z)-11-hexadecenal and between 1 and 100% (Z)-11-hexadecen-1-yl acetate.

In some embodiments, the pheromone composition may further comprise one or more additional compounds such as a liquid or solid carrier or substrate. For example, suitable carriers or substrate include vegetable oils, refined mineral oils or fractions thereof, rubbers, plastics, silica, diatomaceous earth, wax matrix and cellulose powder.

The pheromone composition may be formulated as is known in the art. For example, it may be under the form of a solution, a gel, a powder. The pheromone composition may be formulated so that it can be easily dispensed, as is known in the art.

Kit of Parts

Also provided herein is a kit of parts comprising a yeast cell, and/or a nucleic acid construct as described herein, and instructions for use.

In some embodiments, the kit comprises a yeast cell that can be used in the methods described herein. In other embodiments, the kit comprises a nucleic acid construct that can be used to engineer a yeast cell useful for the methods described herein. In some embodiments, the kit comprises a yeast cell and a nucleic acid construct as described herein.

EXAMPLES

Example 1: Construction of Plasmids and Strains

Four genes encoding Δ11-desaturases from *A. transitella* (SEQ ID NO: 1), *A. segetum* (SEQ ID NO: 42), *S. littoralis* (SEQ ID NO: 40), and *T. ni* (SEQ ID NO: 44) were synthesized by GeneArt (Life Technologies) in codon-optimized versions for *S. cerevisiae*. Four genes encoding fatty acyl reductases from *A. segetum* (SEQ ID NO: 3), *H. armigera* (SEQ ID NO: 7), *H. assulta* (SEQ ID NO: 11), and *H. subflexa* (SEQ ID NO: 15) were also synthesized by GeneArt (Life Technologies) in codon-optimized versions for *S. cerevisiae*. Additionally several fatty acyl reductases were expressed with altered ER retention signals at their C-termini. Fatty acyl reductase from *H. armigera* was modified so that its putative native KKSYE signal was replaced with HDEL signal from *S. cerevisiae* (SEQ ID NO: 9). Fatty acyl reductase from *H. subflexa* was modified so that its putative native EKKT signal was replaced with HDEL (from *S. cerevisiae*) (SEQ ID NO: 17). Fatty acyl reductase from *H. assulta* was modified so that its putative native KKTTNK signal was replaced with HDEL (from *S. cerevisiae*) (SEQ ID NO: 13). The gene encoding *S. cerevisiae* alcohol acetyltransferase (AcT) ATF1 was amplified from genomic DNA preparation of *S. cerevisiae* strain CEN.PK 102-5B. DNA fragments were amplified by PCR using primers with EasyClone-compatible overhangs as described in (Jensen et al, 2014). The primers are listed in Table 1 and the DNA fragments are listed in Table 2. The PCR mix contained 32 μl water, 10 μl high fidelity Phusion® polymerase buffer (5×), 1 μl dNTPs (10 mM), 1 μl Pfu7x polymerase, 2.5 μl forward primer (10 μM), 2.5 μl reverse primer (10 μM) and 1 μl DNA template and the following PCR program was used: 94° C. for 2 min, 30 cycles of [94° C. for 15 sec, 63° C. for 20 sec, 68° C. for 1 min 30 sec], 68° C. for 2 min, pause at 10° C. The PCR products were separated on a 1%-agarose gel containing Safe-Red® (iN-tRON Biotechnology). PCR products of the correct size were excised of the gel and purified using the Nucleospin® Gel and PCR Clean-up kit (Macherey-Nagel).

TABLE 1

Primers.

| Primer name | Primer sequence, 5'->3' | SEQ ID NO: |
|---|---|---|
| PR-8330 (Ase_FAR_U1_fw) | agtgcagguaaaacaatgccagtcttgacttctagag | 19 |
| PR-8331 (Ase_FAR_U1_rev) | cgtgcgauttacttcttcttttcta | 20 |
| PR-8332 (Har_FAR_U1_fw) | agtgcagguaaaacaatggttgtcttgacctccaaag | 21 |
| PR-8336 (Hs_FAR_U1_fw) | agtgcagguaaaacaatggttgtcttgacctc | 22 |
| PR-8337 (Hs_FAR_U1_rev) | cgtgcgauttaagtcttttttttcca | 23 |
| PR-8340 (Has_FAR_U1_fw) | agtgcagguaaaacaatggttgtcttgacctc | 24 |
| PR-8341 (Has_FAR_U1_rev) | cgtgcgauttacttgttggtagtct | 25 |
| PR-8350 (Atrd11_U1_fw) | agtgcagguaaaacaatggttccaaacaagggttcc | 26 |
| PR-8351 (Atrd11_U1_rev) | cgtgcgautcatctctttctaccccc | 27 |
| PR-10350 (atf1_U1_fw) | agtgcagguaaaacaatgaatgaaatcgatgag | 28 |
| PR-10351 (atf1_U1_rev) | cgtgcgauctaagggcctaaaaggagagctttg | 29 |
| PR-10738 (Har_FAR_KKSYE_U1_rev) | cgtgcgaUttattcgtagcttttttttccaagaaatgtctaacac | 30 |
| PR-10739 (Har_FAR_HDEL_U1_rev) | cgtgcgaUttacaattcatcatgttccaagaaatgtctaacac | 31 |
| PR-10740 (Hs_FAR_HDEL_U1_rev) | cgtgcgaUttacaattcatcatgcaagaaatgtctaacaccc | 32 |
| PR-10741 (Has_FAR_HDEL_U1_rev) | cgtgcgaUttacaattcatcatgttccaagaagtgtctaacac | 33 |
| PR-14126 (Ased11_U1_fw) | gtgcaggUaaaacaatggctcaag | 48 |
| PR-14127 (Ased11_U1_rev) | cgtgcgaUttagttgtccttcc | 49 |
| PR-14128 (Sld11_U1_fw) | agtgcaggUaaaacaatggctcaat | 50 |
| PR-14129 (Sld11_U1_rev) | cgtgcgaUtcattcacccctta | 51 |
| PR-14130 (Tnd11_U1_fw) | agtgcaggUaaaacaatggctgttatg | 52 |
| PR-14131 (Tnd11_U1_rev) | cgtgcgaUtcattctttcttagcgtagaaa | 53 |

TABLE 2

DNA fragments obtained by PCR using the indicated template and primers.

| Gene fragment name | Gene | Fw_primer | Rv_primer | Template DNA |
|---|---|---|---|---|
| BB0684 (Ase_FAR<–) | Fatty acyl-CoA reductase from *Agrotis segetum* | PR-8330 (Ase_FAR_U1_fw) | PR-8331 (Ase_FAR_U1_rev) | SEQ ID NO: 3 |
| BB0687 (Hs_FAR<–) | Fatty acyl-CoA reductase from *Heliothis subflexa* | PR-8336 (Hs_FAR_U1_fw) | PR-8337 (Hs_FAR_U1_rev) | SEQ ID NO: 15 |
| BB0689 (Has_FAR<–) | Fatty acyl-CoA reductase from *Helicoverpa assulta* | PR-8340 (Has_FAR_U1_fw) | PR-8341 (Has_FAR_U1_rev) | SEQ ID NO: 11 |
| BB0694 (Atrd11<–) | Δ11-desaturase from *Amyelois transitella* | PR-8350 (Atrd11_U1_fw) | PR-8351 (Atrd11_U1_rev) | SEQ ID NO: 1 |
| BB1143 (ScATF1<–) | Alcohol acetyltransferase from *S. cerevisiae* | PR-10350 (atf1_U1_fw) | PR-10351 (atf1_U1_rev) | Genomic DNA from *S. cerevisiae* CEN.PK102-5B |
| BB0914 (Har_FAR<–) | Fatty acyl-CoA reductase from *Helicoverpa armigera* | PR-8332 (Har_FAR_U1_fw) | PR-10738 (Har_FAR_KKSYE_U1_rev) | SEQ ID NO: 7 |
| BB0915 (Har_FAR_H DEL<–) | Fatty acyl-CoA reductase from *Helicoverpa armigera* with modified C-terminus | PR-8332 (Har_FAR_U1_fw) | PR-10739 (Har_FAR_HDEL_U1_rev) | SEQ ID NO: 9 |
| BB0916 (Hs_FAR_H DEL<–) | Fatty acyl-CoA reductase from *Heliothis subflexa* with modified C-terminus | PR-8336 (Hs_FAR_U1_fw) | PR-10740 (Hs_FAR_HDEL_U1_rev) | SEQ ID NO: 17 |
| BB0917 (Has_FAR_H DEL<–) | Fatty acyl-CoA reductase from *Helicoverpa assulta* with modified C-terminus | PR-8340 (Has_FAR_U1_fw) | PR-10741 (Has_FAR_HDEL_U1_rev) | SEQ ID NO: 13 |
| BB0410 (PTDH3<–) | PTDH3 promoter from *S. cerevisiae* | PR-1852 (PTDH3_fw) | PR-1853 (PTDH3_rv) | Genomic DNA from *S. cerevisiae* CEN.PK102-5B |
| BB1354 (Ased11<–) | Δ11-desaturase from *A. segetum* | PR-14126 (Ased11_U1_fw) | PR-14127 (Ased11_U1_rev) | SEQ ID NO: 42 |
| BB1355 (Sld11<–) | Δ11-desaturase from *Spodoptera littoralis* | PR-14128 (Sld11_U1_fw) | PR-14129 (Sld11_U1_rev) | SEQ ID NO: 40 |
| BB1356 (Tnd11<–) | Δ11-desaturase from *Trichoplusia ni* | PR-14130 (Tnd11_U1_fw) | PR-14131 (Tnd11_U1_rev) | SEQ ID NO: 44 |

The basic integrative vectors EasyClone 2.0 pCfB2190 (XI-2-loxP-KlLEU2syn), pCfB2228 (XII-4-loxP-SpHIS5syn), and pCfB2190 (XI-2-loxP-KlLEU2syn), are described in (Stovicek et al, 2015). Vector for multiple integrations EasyCloneMulti pCfB2047 (pTY2-KlURA3-TAG) is described in (Maury et al, 2016). Additionally we constructed integrative vector pCfB2912 (XI-5-loxP-NatMXsyn). Plasmid pCfB2912 was constructed by USER fusion as described in Stovicek et al. 2015 using BB0593 and BB0598, the original vector backbone and the nourseothricin resistance cassette, respectively.

All basic integrative vectors were linearized with FastDigest® AsiSI (Fermentas) for 2 hours at 37° C. and then nicked with Nb.BsmI (New England Biolabs) for 1 hour at 65° C. The resulting vectors containing sticky ends were separated by gel electrophoresis, excised and gel-purified using the Nucleospin® Gel and PCR Clean-up kit (Macherey-Nagel). The DNA fragments were cloned into the so prepared vectors by USER-cloning via the following protocol: 1 μl of linearized plasmid, 1 μl of promoter fragment, 1.5 μl of gene fragment, 1 μl high fidelity Phusion® polymerase buffer (5×), and 0.5 μl USER enzyme (New England Biolabs) were mixed and incubated at 37° C. for 25 min and at 25° C. for 25 min. The reaction was transformed into chemically competent *E. coli* DHalpha cells and the cells were plated on Lysogeny Broth (LB) agar plates with 100 mg/L ampicillin. The plates were incubated overnight at 37° C. and the resulting colonies were screened by colony PCR. The plasmids were purified from overnight *E. coli* cultures and the correct cloning was confirmed by sequencing. The constructed integrative vectors are listed in Table 3.

TABLE 3

Integrative expression vectors.

| Integrative expression vector name | Selection marker | Parent vector | DNA fragments cloned into parent vector |
|---|---|---|---|
| pCfB2501 (pXI-2-loxP-KILEU2syn-Ase_FAR-PTDH3<-) | KILEU2 | pCfB2190 | BB0410 (PTDH3<-), BB0684 (Ase_FAR<-) |
| pCfB3412 (pXI-2-loxP-KILEU2syn-Har_FAR-PTDH3<-) | KILEU2 | pCfB2190 | BB0410 (PTDH3<-), BB0914 (Har_FAR<-) |
| pCfB2504 (pXI-2-loxP-KILEU2syn-Hs_FAR-PTDH3<-) | KILEU2 | pCfB2190 | BB0410 (PTDH3<-), BB0687 (Hs_FAR<-) |
| pCfB2506 (pXI-2-loxP-KILEU2syn-Has_FAR-PTDH3<-) | KILEU2 | pCfB2190 | BB0410 (PTDH3<-), BB0689 (Has_FAR<-) |
| pCfB2537 (pXII-4-loxP-SpHIS5syn-Atrd11-PTDH3<-) | SpHIS5syn | pCfB2228 | BB0410 (PTDH3<-), BB0694 (Atrd11<-) |
| pCfB3630 (pXI-5-loxP-NatMXsyn-ScATF1-PTDH3<-) | NatMXsyn | pCfB2912 | BB0410 (PTDH3<-), BB1143 (ScATF1<-) |
| pCfB3413 (pXI-2-loxP-KILEU2syn-Har_FAR_HDEL-PTDH3<-) | KILEU2 | pCfB2190 | BB0410 (PTDH3<-), BB0915 (Har_FAR_HDEL<-) |
| pCfB3414 (pXI-2-loxP-KILEU2syn-Hs_FAR_HDEL-PTDH3<-) | KILEU2 | pCfB2190 | BB0410 (PTDH3<-), BB0916 (Hs_FAR_HDEL<-) |
| pCfB3415 (pXI-2-loxP-KILEU2syn-Has_FAR_HDEL-PTDH3<-) | KILEU2 | pCfB2190 | BB0410 (PTDH3<-), BB0917 (Has_FAR_HDEL<-) |
| pCfB4369 (pXII-4-loxP-SpHIS5syn-Ased11-PTDH3<-) | SpHIS5syn | pCfB2228 | BB0410 (PTDH3<-), BB1354 (Ased11<-) |
| pCfB4370 (pXII-4-loxP-SpHIS5syn-Sld11-PTDH3<-) | SpHIS5syn | pCfB2228 | BB0410 (PTDH3<-), BB1355 (Sld11<-) |
| pCfB4371 (pXII-4-loxP-SpHIS5syn-Tnd11-PTDH3<-) | SpHIS5syn | pCfB2228 | BB0410 (PTDH3<-), BB1356 (Tnd11<-) |
| pCfB3699 | KIURA3 | pCfB2047 | BB0410 (PTDH3<-), BB0914 (Har_FAR<-) |

The integrative expression vectors were linearized with FastDigest® NotI (Fermentas) and transformed into *S. cerevisiae* using lithium-acetate protocol (Gietz & Schiestl, 2007). Positive transformants were selected on yeast synthetic drop-out plates (Sigma-Aldrich). Correct integration of the expression constructs into the genome of *S. cerevisiae* was confirmed by colony PCR.

Example 2: Production of (Z)-11-hexadecenol in *S. cerevisiae* Upon Overexpression of Δ11-Desaturase from *Amyelois transitella* and Four Variants of Fatty Acyl-CoA Reductase We constructed *S. cerevisiae* strains that overexpress Δ11-desaturase from *A. transitella* and variants of fatty acyl-CoA reductases with native or HDEL C-terminus (Table 4). Three individual isolates of each strain were examined for acquired ability to produce (Z)-11-hexadecen-1-ol. Individual colonies were inoculated in 3 ml yeast synthetic drop-out liquid medium lacking histidine and leucine in 24-deep well microtiter plates with air-penetrable lids (EnzyScreen) and incubated overnight at 30° C. with shaking at 250 rpm. The control parental strain CEN.PK102-5B was cultivated in synthetic complete medium. The next day 60 µl of pre-culture was transferred into 540 µl mineral medium in a 96-deep well microtiter plates with air-penetrable lids (EnzyScreen). The mineral medium had the composition as described in (Jensen et al, 2014). For the control strain the medium was supplemented with 240 mg/L leucine, 76 mg/L histidine and 20 mg/L uracil and the medium for the other strains was supplemented with 20 mg/L uracil. The microtiter plates were incubated at 30° C. with shaking at 250 rpm for 48 hours. After taking a sample for OD, to the remaining 495 ul of culture an equal volume of decane was added. The plate was covered with a lid made of Viton from EnzyScreen (to avoid absorption of the organic solvent into the lid) and the plate was shaken for 10 min at 250 rpm. The resulting emulsion was transferred to a 4 mL-glass vial, closed with a lid, vortexed for 20 sec and centrifuged for 35 sec at 4000×g. The bottom (water) phase was removed and 0.1 g $Na_2SO_4$ was added to the remaining decane phase. The mix was vortexed for 10 sec and the clear organic phase was transferred to a glass vial for GC-MS analysis. GC-MS analyses were performed on a Hewlett Packard 6890 GC coupled to a mass selective detector HP 5973. The GC was equipped with an INNOWax column (30 m×0.25 mm×0.25 µm), and helium was used as carrier gas (average velocity: 33 cm/s). The MS was operated in electron impact mode (70 eV), scanning between m/z 30 and 400, and the injector was configured in splitless mode at 220° C. The oven temperature was set to 80° C. for 1 min, then increased at a rate of 10° C./min to 210° C., followed by a hold at 210° C. for 15 min, and then increased at a rate of 10 C/min to 230° C. followed by a hold at 230° C. for 20 min. Compounds were identified by comparison of retention times and mass spectra with those of reference compounds available in laboratory collection.

Compounds were quantified by the Total Ion Current (TIC) recorded. Data were analysed by the Agilent ChemStation software and iWork Numbers. The concentration of (Z)-11-hexadecen-1-ol was calculated based on calibration curve ranging from 0 mg/L to 15 mg/L of (Z)-11-hexadecen-1-ol standard. The standards was purchased from Pherobank (Wageningen, Netherlands).

Introduction of Δ11-desaturase from *A. transitella* and of a fatty acyl-CoA reductase from *H. armigera* or *H. subflexa* or *H. assulta* enabled *S. cerevisiae* to synthesize (Z)-11-hexadecen-1-ol at 1-3.9 mg/L titer (Table 4). Previous studies have previously reported that production of (Z)-11-hexadecen-1-ol was obtained when expressing Ase_Δ11 and Ase_FAR in *S. cerevisiae* (Hagström et al., 2013). However, our results show that Ase_FAR has a very low activity and is much less suitable for production of (Z)-11-hexadecen-1-ol than Har_FAR, Hs_FAR or Has_FAR.

TABLE 4

*S. cerevisiae* strains engineered for production of (Z)-11-hexadecen-1-ol with different variants of fatty acyl-CoA reductase.

| Strain name | Overexpressed heterologous genes | Parent strain and (integrated vectors) | (Z)-11-hexadecen-1-ol titer [mg/L] |
|---|---|---|---|
| ST3328 | AtrΔ11, Ase_FAR | CEN.PK102-5B (pCfB2537, pCfB2501) | 0 ± 0 |
| ST3705 | AtrΔ11, Har_FAR | CEN.PK102-5B (pCfB2537, pCfB3412) | 1.57 ± 0.27 |
| ST3330 | AtrΔ11, Hs_FAR | CEN.PK102-5B (pCfB2537, pCfB2504) | 1.26 ± 0.32 |
| ST3339 | AtrΔ11, Has_FAR | CEN.PK102-5B (pCfB2537, pCfB2506) | 3.28 ± 1.23 |
| ST3706 | AtrΔ11, Har_FAR_HDEL (SEQ ID NO: 10) | CEN.PK102-5B (pCfB2537, pCfB3413) | 3.85 ± 1.63 |
| ST3707 | AtrΔ11, Hs_FAR_HDEL (SEQ ID NO: 18) | CEN.PK102-5B (pCfB2537, pCfB3414) | 2.49 ± 0.96 |
| ST3708 | AtrΔ11, Has_FAR_HDEL (SEQ ID NO: 14) | CEN.PK102-5B (pCfB2537, pCfB3415) | 1.02 ± 0.79 |
| ST10 | None | CEN.PK102-5B (none) | 0 ± 0 |

Example 3: Production of (Z)-11-hexadecenol in *S. cerevisiae* Upon Overexpression of Fatty Acyl-CoA Reductase from *H. armigera* and Four Variants of Δ11-Desaturase We constructed *S. cerevisiae* strains that overexpress fatty acyl-CoA reductase from *H. armigera* with modified C-terminus and four variants of Δ11-desaturase in order to identify the one with the highest activity (Table 5). Two individual isolates of each strain were examined for acquired ability to produce (Z)-11-hexadecen-1-ol.

Individual colonies were inoculated in 5 ml of Yeast extract-Peptone-Dextrose (YPD) medium with 8% glucose (10 g/L yeast extract, 20 g/L peptone, 80 g/L dextrose) in 12-ml glass tubes (Duran, Wertheim, Germany) with metal labocap lids (Lüdiswiss, Flawil, Switzerland) and incubated overnight at 30° C. with shaking at 250 rpm. The following day the overnight culture was centrifuged, the supernatant was discarded and the pellet was resuspended in 2 mL feed-in-time (FIT) medium supplemented with 20 mg/L uracil. The feed-in-time medium was purchased from m2p-labs GmbH (Baesweiler, Germany). It was supplemented with 0.5% enzyme solution and 1% vitamin solution immediately prior to use. The tubes were incubated at 30° C. with shaking at 250 rpm for 40 hours. For extraction, 1 mL of culture was transferred into a 4-mL glass vial and 10 μL of internal standard stock (1 μg/μL (Z)-10-heptan-1-yl methyl ester in 100% ethanol) was added. The vials were covered with small pieces of aluminum foil and we used a needle to pierce small holes in the foil covers. The samples were vortexed and placed at −80° C. for storage until analysis. The samples were freeze-dried in a freeze dry system (Freezone6 and Stoppening tray dryer, Labconco, Kansas City, USA) at −40° C., then 1 mL chloroform:methanol 2:1 was added to disrupt the cells. The mix was vortexed for 45 s and left at room temperature for 4 hours. The organic solvents were evaporated slowly under a nitrogen stream. 1 ml of hexane was added, the samples were vortexed for 10 s, centrifuged and 200 μl were transferred to a new glass vial. GC-MS analysis was performed as described in Example 2. The concentration of (Z)-11-hexadecen-1-ol was calculated based on internal standard and calibration curve.

The product (Z)-11-hexadecen-1-ol was produced by all the four tested strains, but Δ11-desaturase from *A. transitella* was clearly superior to others, resulting in a titer of ca. 7 mg/L. The titer of strain ST3706 was higher than in example 2 due to improved cultivation and extraction protocol.

TABLE 5

*S. cerevisiae* strains engineered for production of (Z)-11-hexadecen-1-ol with different variants of Δ11-desaturase.

| CfB strain name | Overexpressed heterologous genes | Parent strain and (integrated vectors) | (Z)-11-hexadecen-1-ol liter [mg/L] |
|---|---|---|---|
| ST3706 | AtrΔ11, Har_FAR_HDEL | CEN.PK102-5B (pCfB2537, pCfB3413) | 7.1 ± 0.53 |
| ST4487 | AseΔ11, Har_FAR_HDEL | CEN.PK102-5B (pCfB4369, pCfB3413) | 1.8 ± 0.26 |
| ST4488 | SlΔ11, Har_FAR_HDEL | CEN.PK102-5B (pCfB4370, pCfB3413) | 3.2 ± 0.35 |
| ST4489 | TniΔ11, Har_FAR_HDEL | CEN.PK102-5B (pCfB4371, pCfB3413) | 3.5 ± 0.42 |

Example 4: Improved Production of (Z)-11-hexadecen-1-ol by Integration of Multiple Copies of Fatty Acyl-CoA Reductase We constructed *S. cerevisiae* strains that overexpress Δ11-desaturase from *A. transitella* and fatty acyl-CoA reductase from *H. armigera* Har_FAR. The Har_FAR gene was integrated in either a single (ST3705) or multiple copies into the genome (ST5262). ST3705 was inoculated into 5 ml of YPD medium with 8% glucose (10 g/L yeast extract, 20 g/L peptone, 80 g/L dextrose) and ST5262 was inoculated into 5 ml synthetic complete medium lacking uracil. Both strains were cultivated in 12-ml glass tubes (Duran, Wertheim, Germany) with metal labocap lids (Lüdiswiss, Flawil, Switzerland) and incubated overnight at 30° C. with shaking at 250 rpm. The following day the overnight culture was centrifuged, the supernatant was discarded and the pellet was resuspended in 2 mL feed-in-time (FIT) medium. For strain ST3705 the medium was supplemented with 20 mg/L uracil. The feed-in-time medium was purchased from m2p-labs GmbH (Baesweiler, Germany). It was supplemented with 0.5% enzyme solution and 1% vitamin solution immediately prior to use. The tubes were incubated at 30° C. with shaking at 250 rpm for 40 hours. The sample extraction was performed as in described in Example 3. Integration of multiple Har_FAR gene copies increased production eight fold (Table 6).

TABLE 6

*S. cerevisiae* strains engineered for production of (Z)-11-hexadecen-1-ol with different gene copy numbers of fatty acyl reductase.

| CfB strain name | Overexpressed heterologous genes | Parent strain and (integrated vectors) | (Z)-11-hexadecen-1-ol titer [mg/L] |
|---|---|---|---|
| ST3705 | AtrΔ11, Har_FAR | CEN.PK102-5B (pCfB2537, pCfB3412) | 11.0 ± 1.4 |
| ST5262 | AtrΔ11, Har_FAR (multiple copies integrated) | CEN.PK102-5B (pCfB2537, pCfB3412, pCfB3699) | 85.4 ± 0.8 |

Example 5: Production of (Z)-11-hexadecen-1-ol in Fed-Batch Fermentation

Strain ST3705 was tested for production of (Z)-11-hexadecen-1-ol in fed-batch fermentation. About 1 ml of cryo culture of strain ST3705 was inoculated into 150 ml of synthetic complete medium without leucine and histidine (SC leu-his-) in 500-ml-baffled shake flask and incubated shaking at 250 rpm for 24 hours at 30° C. The inoculum was up-concentrated by centrifuging the culture, removing 100 ml of supernatant and resuspending the cells in the remaining 50 ml of liquid. This cell suspension was used to inoculate 500 mL fermentation medium (6 g/L KH2PO4, 4 g/L (NH4)2SO4, 1 g/L MgSO4*7H2O, 1 ml/L antifoam 204, 4 ml/L trace metals (Jensen, 2013), 2 ml/L vitamins (Jensen, 2013), and 32 mg/L uracil) in a 1 L Sartorius bioreactor. The reactor operating conditions were 30° C., aeration at 1 L/min, and agitation at 800 rpm. The pH was kept at 5 with 2M KOH. The feed solution was composed of 500 ml 200 g/L glucose. 100 ml of feed solution was added to the reactor to start the fermentation. 24 hours later, constant feed rate of 5 g/h was applied and maintained throughout the fermentation.

Strain ST5262 was tested for production of (Z)-11-hexadecen-1-ol in fed-batch fermentation. Strain ST5262 was inoculated into 100 mL double concentrated synthetic complete medium without uracil (2×SC ura-) in 2 L-baffled flask and incubated shaking at 250 rpm for 24 h at 28° C. Additional 400 mL of 2×SC ura- were added and the incubation continued under the same conditions for additional 48 hours. To prepare a concentrated inoculum for the fermentation, the cells were centrifuged and resuspended in 50 mL of the remaining supernatant. This cell suspension was used to inoculate 500 mL fermentation medium (6 g/L KH$_2$PO$_4$, 6 g/L (NH$_4$)$_2$SO$_4$, 1 g/L MgSO$_4$*7H$_2$O, 1 ml/L antifoam 204, 4 ml/L trace metals (Jensen, 2013), 2 ml/L vitamins (Jensen, 2013)) in a 1 L Sartorius bioreactor. The reactor operating conditions were 30° C., aeration at 1.5 L/min, and agitation at 800 rpm. Dissolved oxygen was controlled at above 20% by automatic blending of oxygen into the air. The pH was kept at 5 with 10% KOH. The feed solution was composed of 500 ml 330 g/L dextrose supplemented with 0.5 ml antifoam 204. Ca. 20 ml of feed solution was added to the reactor to start the fermentation. The feed rate was set to 5 g/h. The feed rate was increased to 7.5 g/h at 17 hours from the start of fermentation and further to 10 g/h at 34 hours from the start of fermentation. The feed rate was decreased to 3 g/h at 60 hours until the culture was harvested at 100 hours, by which time all the feed was consumed.

Figure 2:
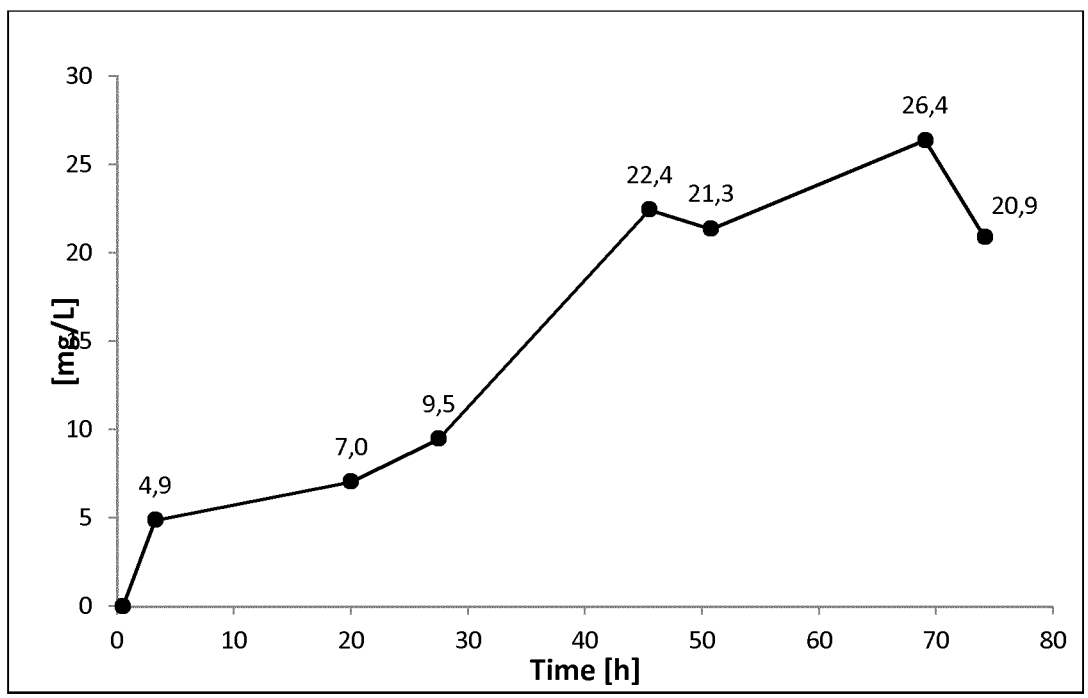
FIG. 2. (Z)-11-hexadecen-1-ol production during fed-batch fermentation. X-axis shows (Z)-11-hexadecen-1-ol titre in mg/L, Y-axis shows fermentation time in hours. (A) Titres obtained with integration of a single gene copy (strain ST3705). (B) Titres obtained with integration of multiple gene copies (strain ST5262).
Figure 2:
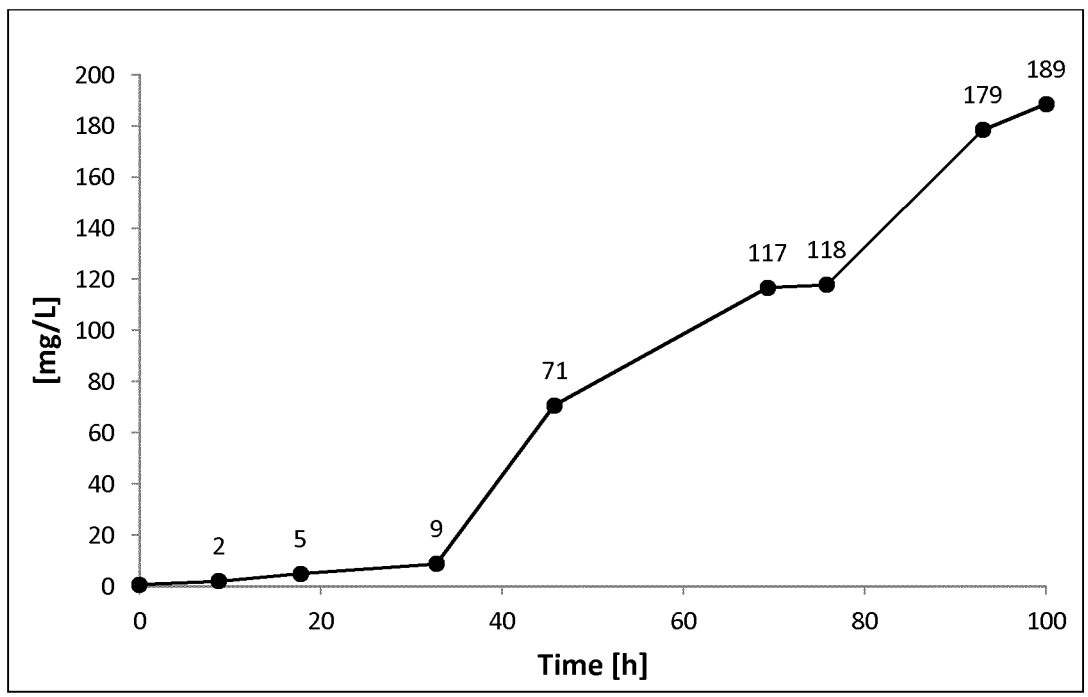

Sampling was performed by withdrawing a few mL broth with a syringe from an outlet in the reactor, transferring the sample to a plastic tube, kept at −20° C. until (Z)-11-hexadecen-1-ol extraction. Extraction and GC-MS analysis were performed as described in Example 3. The final production titre for strain ST3705 was 20 mg/L (FIG. 2A) and for strain ST5262 it was 189 mg/L (FIG. 2B).

Example 6: Production of (Z)-11-hexadecen-1-ol in *Yarrowia lipolytica*

Figure 3:
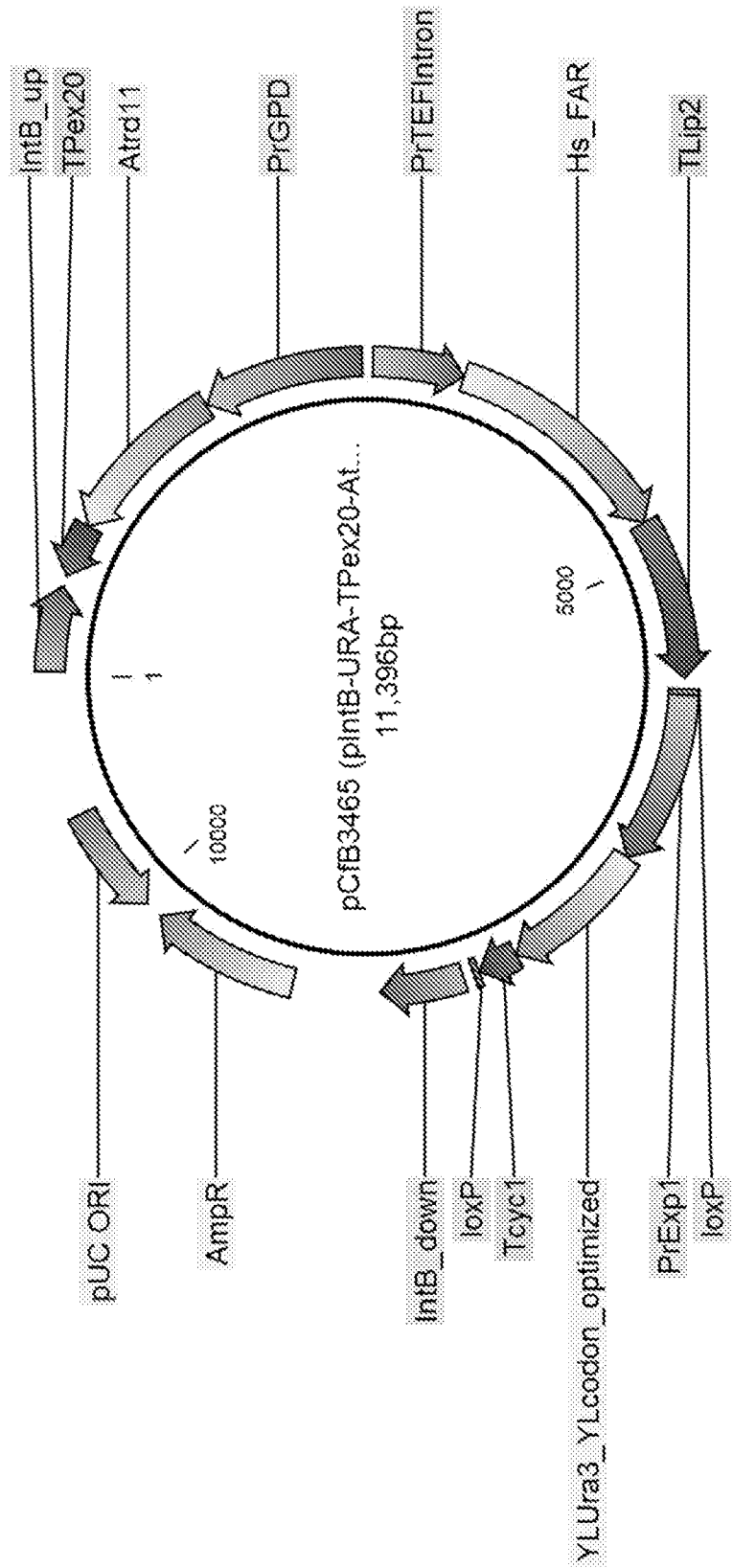
FIG. 3. Vector map of plasmid pCfB3465. The vector encodes expressions cassettes for the Atrd11, Hs_FAR, and URA3 gene. The expression is driven from *Y. lipolytica* native promoters (Pr). The expression cassettes are flanked by genomic DNA sequences (IntB_up and IntB_down) of 500 bp allowing site-specific integration into the *Y. lipolytica* genome.

We tested production of (Z)-11-hexadecen-1-ol in *Y. lipolytica* expressing Δ11-desaturase from *A. transitella* and fatty acyl-CoA reductase from *H. subflexa*. Genes encoding an *A. transitella* Δ11-desaturase (SEQ ID NO: 2) and a *H. subflexa* fatty acyl-CoA reductase (SEQ ID NO: 16) were cloned into a *Y. lipolytica* expression vector resulting in plasmid pCfB3465 (FIG. 3). Prior to transformation into *Y. lipolytica* the expression plasmid was linearized with NotI. The linearized plasmid was transformed into strain *Y. lipolytica* GB20 (Angerer, 2014) using a lithium-acetate-based protocol (Chen, 1997). Positive transformants were selected on synthetic complete (SC) medium lacking uracil. The integration of the expression construct into the *Y. lipolytica* genome was confirmed by colony PCR.

One individual clone of each strain was inoculated into 5 ml YPD medium with 8% glucose (10 g/L yeast extract, 20 g/L peptone, 80 g/L dextrose) in 12-ml glass tubes (Duran, Wertheim, Germany) with metal labocap lids (Lüdiswiss, Flawil, Switzerland) and incubated overnight at 30° C. with shaking at 250 rpm. The following day the overnight culture was centrifuged, the supernatant was discarded and the pellet was resuspended in 2 ml nitrogen-limited medium (2.9 g/L (NH$_4$)$_2$SO$_4$, 1.7 g/L YNB (without amino acids and ammonium sulfate, 240 mg/L leucine, 76 mg/L lysine) and 61 g/L glycerol). For strain ST3683 the medium was supplemented with 20 mg/L uracil. The cultures were incubated for 48 hours at 30° C. and shaken at 250 rpm. Extraction and GC-MS analysis were performed as described in Example 3. The *Y. lipolytica* strain ST3844 expressing *A. transitella* Δ11-desaturase and *H. subflexa* fatty acyl-CoA reductase produced 1.7 mg/L of (Z)-11-hexadecen-1-ol (Table 7).

TABLE 7

Strains and (Z)-11-hexadecen-1-ol titres

| CfB strain name | Parent strain | Integrated vector | (Z)-11-hexadecen-1-ol titers [mg/L] |
|---|---|---|---|
| ST3683 | — | — | 0.20 ± 0.03 |
| ST3844 | ST3683 | pCfB3465 | 1.71 ± 0.14 |

Example 7: Production of (Z)-11-hexadecen-1-yl acetate

We constructed strain ST3581, expressing Δ11-desaturase from *A. transitella*, fatty acyl-CoA reductase from *H. subflexa* and a *S. cerevisiae* alcohol acetyltransferase AcT for production of (Z)-11-hexadecen-1-yl acetate.

Individual colonies of ST3581 and the control strain, ST3330, which does not overexpress the alcohol acetyltransferase, were inoculated in 5 ml of YPD medium with 8% glucose (10 g/L yeast extract, 20 g/L peptone, 80 g/L dextrose) in 12-ml glass tubes (Duran, Wertheim, Germany) with metal labocap lids (Lüdiswiss, Flawil, Switzerland) and incubated overnight at 30° C. with shaking at 250 rpm. The following day the overnight culture was centrifuged, the supernatant was discarded and the pellet was resuspended in 2 ml nitrogen-limited mineral medium (1.25 g/L (NH$_4$)$_2$SO$_4$, 14.4 g/L KH$_2$PO$_4$, 0.5 g/L MgSO$_4$*7H$_2$O, 2 mL/L trace metal solution (Jensen, 2013), 1 mL/L vitamin solution (Jensen, 2013)) with 20 g/L glucose. The cultures were incubated for 48 hours at 30° C. and shaken at 250 rpm. Extraction and GC-MS analysis was performed as described in Example 3. ST3581 produced 1.68 mg/L (Z)-11-hexadecen-1-yl acetate, while no (Z)-11-hexadecen-1-yl acetate production could be observed in the control strain ST3330 (Table 8).

TABLE 8

Strains and (Z)-11-hexadecen-1-yl acetate titers.

| CfB strain name | Parent Strain | Over-expressed genes | Integrated plasmids | (Z)-11-hexadecen-1-yl acetate (mg/L) |
|---|---|---|---|---|
| ST3581 | CEN.PK102-5B | AtrΔ11, Hs_FAR, ScATF1 | pCfB2537, pCfB2504, pCfB3630 | 1.68 ± 0.17 |
| ST3330 | CEN.PK102-5B | AtrΔ11, Hs_FAR | pCfB2537, pCfB2504 | 0.00 ± 0.00 |

Sequences

SEQ ID NO: 1 - *S. cerevisiae*-codon-optimized nucleotide sequence of *A. transitella* Δ11-desaturase; mRNA-coding sequence.
Atggttccaaacaagggttcctctgatgtttgtctgaacattctgaaccacaattcaccaagttgattgctccacaagctggt ccaagaaagtacaaaatcgtttacagaaacttgttgaccttcggttactggcatttgtctgctgtttatggtttgtacttgtgtttca cttgtgctaagtgggctactattttgttcgctttcttcttgtacgttatcgccgaaattggtattactggtggtgctcatagattatgg gctcatagaacttacaaagccaagttgccattggaaatcttgttgttgatcatgaactccattgccttccaagatactgttttta cttgggctagagatcatagattgcatcacaagtactctgatactgatgctgatccacataatgctactagaggtttcttctact ctcatgttggttggttgttggttaagaaacacccagaagttaaggctagaggtaagtacttgtctttggatgacttgaagaac aacccttgttgaagttccaaaagaagtacgccattttggtcattggtactttgtgcttttgatgccaactttcgttccagtttactt ttggggtgaaggtatttctactgcctggaacattaacttgttaagatacgtcatgaacttgaacatgaccttttttggttaactccg ctgctcatattttggtaacaagccatacgataagtctatcgcctctgttcaaaacatctctgtttctttggctactttcggtgaag gtttccataactaccatcatacttatccatgggattacagagctgctgaattgggtaacaatagattgaatatgaccaccgc cttcattgatttcttgcttggattggttgggcctacgatttgaaatctgttccacaagaagctattgctaagagatgtgctaaaa ctggtgatggtactgatatgtggggtagaaagagatga SEQ ID NO: 2 - Amino acid sequence of *A. transitella* delta-11-desaturase (translation)
MVPNKGSSDVLSEHSEPQFTKLIAPQAGPRKYKIVYRNLLTFGYWHLSAVYGLYLCFT

CAKWATILFAFFLYVIAEIGITGGAHRLWAHRTYKAKLPLEILLLIMNSIAFQDTAFTWAR

DHRLHHKYSDTDADPHNATRGFFYSHVGWLLVKKHPEVKARGKYLSLDDLKNNPLLK

FQKKYAILVIGTLCFLMPTFVPVYFWGEGISTAWNINLLRYVMNLNMTFLVNSAAHIFG

NKPYDKSIASVQNISVSLATFGEGFHNYHHTYPWDYRAAELGNNRLNMTTAFIDFFAW

IGWAYDLKSVPQEAIAKRCAKTGDGTDMWGRKR

SEQ ID NO: 3 - *S. cerevisiae*-codon-optimized nucleotide sequence of *A. segetum* fatty acyl reductase; mRNA-coding sequence.
atgccagtcttgacttctagagaagacgaaaaattgtccgtcccagaattttacgctggtaagtctattttgttaccggtggta ctggtttcttgggtaaggttttatcgaaaagttgttgtactgctgcccagatatcgataagatctacatgttgatcagagaaaa aaagaacttgtccatcgacgaaagaatgtccaagttttggatgaccctttgttctccagattgaaagaagaaagaccagg tgacttggaaaagatcgttttgattccaggtgatattaccgctcctaattgggtttgtctgctgaaaacgaaagaatcttgttg gaaaaggtcagtgtcattattaactctgctgctaccgttaagttcaacgaaccattgccaattgcttggaagattaacgttga aggtactagaatgttgttggccttgtctagaagaatgaagagaatcgaagttttcatccatatctccaccgcttactctaatgc ttcttctgatagaattgtcgttgacgaaatcttgtatccagctccagctgatatggatcaagtttatcaattggttaaggacggt -continued

```
gtcactgaagaagaaaccgaaagattattgaacggtttgccaaacacttacactttcactaaggctttgaccgaacatttg gttgctgaacatcaaacttacgttccaaccattatcatcagaccatctgttgttgcctccattaaggatgaacctattagaggtt ggttgtgtaattggtttggtgctactggtatttctgttttcactgctaagggtttgaacagagttttgttgggtaaagcctctaacat cgttgatgttatcccagttgattacgttgccaacttggttatagttgctggtgctaaatctggtggtcaaaagtctgatgaattga aaatctacaactgctgctcctctgactgtaatccagttactttgaagaagatcatcaaagaattcaccgaagataccatcaa gaacaagtcccatattatgccattgccaggttggttcgttttactaagtacaaatggttgttgactttgttgaccatcatcttcca aatgttgccaatgtatttggccgatgtttacagagtcttgaccggtaaaattccaagatatatgaagttgcaccacttggtcatt caaaccagattgggtattgatttcttcacctctcattcttgggttatgaagaccgatagagtcagagaattattcggttctttgtc cttggccgaaaaacacatgtttccatgtgatccatcttccattgattggaccgattacttgcaatcttactgctatggtgtcaga agattcttagaaaagaagaagtaa
```

SEQ ID NO: 4 - Amino acid sequence of A. segetum fatty acyl reductase
MPVLTSREDEKLSVPEFYAGKSIFVTGGTGFLGKVFIEKLLYCCPDIDKIYMLIREKKNL

SIDERMSKFLDDPLFSRLKEERPGDLEKIVLIPGDITAPNLGLSAENERILLEKVSVIINSA

ATVKFNEPLPIAWKINVEGTRMLLALSRRMKRIEVFIHISTAYSNASSDRIVVDEILYPAP

ADMDQVYQLVKDGVTEEETERLLNGLPNTYTFTKALTEHLVAEHQTYVPTIIIRPSVVA

SIKDEPIRGWLCNWFGATGISVFTAKGLNRVLLGKASNIVDVIPVDYVANLVIVAGAKS

GGQKSDELKIYNCCSSDCNPVTLKKIIKEFTEDTIKNKSHIMPLPGWFVFTKYKWLLTLL

TIIFQMLPMYLADVYRVLTGKIPRYMKLHHLVIQTRLGIDFFTSHSWVMKTDRVRELFG

SLSLAEKHMFPCDPSSIDWTDYLQSYCYGVRRFLEKKK

SEQ ID NO: 5 - *S. cerevisiae*-codon-optimized nucleotide sequence of *H. armigera* fatty acyl reductase with signal peptide changed to KKYR; mRNA-coding sequence.
atggttgtcttgacctccaaagaaactaagccatctgttgctgaattttacgctggtaagtctgttttcattactggtggtactggt ttcttgggtaaggttttcattgaaaagttgttgtactcctgcccagatatcggtaatatctacatgttgatcagagaaaagaag ggtttgtccgtttccgaaagaatcaagcactttttggatgatcctttgttcaccagattgaaagaaaaaagaccagccgactt ggaaaagatcgttttgattccaggtgatattactgctccagatttgggtattacctccgaaaacgaaaagatgttgatcgaa aaggtcagtgtcattattcattctgctgctaccgttaagttcaacgaaccattgccaactgcttggaagattaacgttgaaggt actagaatgatgttggccttgtctagaagaatgaagagaatcgaagttttcatccatatctctaccgcttacactaacacca acagagaagttgttgacgaaatcttgtatccagctccagctgatattgatcaagttcacagatatgttaaggacggtatctct gaagaagaaactgaaaaaatcttgaacggtagaccaaacacttacactttcactaaggctttgaccgaacatttggttgct gaaaatcaagcttacgttccaaccattatcgttagaccatcagttgttgctgccattaaggatgaacctattaagggttggttg ggtaattggtatggtgctacaggtttgactgtttttactgctaagggtttgaacagagttatctacggtcactcttctaacatcgtt gatttgatcccagttgattacgttgccaacttggttattgctgctggtgctaaatcttctaagtctactgaattgaaggtctacaa ctgctgttcttctgcttgtaacccaattactatcggtaagttgatgtccatgtttgctgaagatgctatcaagcaaaagtcttacg ctatgccattgccaggttggtacatttttactaagtacaagtggttggtcttgttgttgaccattttgttccaagttattccagccta cattaccgacttgtacagacatttgattggtaagaacccaagatatatcaagttgcaatccttggtcaatcaaaccagatcc tccattgatttcttcacctctcattcttgggttatgaaggctgatagagtcagagaattattcgcttctttgtctccagcagataag tacttgtttccatgtgatccaaccgatattaactggacccattacattcaagattactgctggggtgttagacatttcttggaaa aaaagtacagataa SEQ ID NO: 6 - Amino acid sequence of *H. armigera* fatty acyl reductase with signal peptide changed to KKYR
MVVLTSKETKPSVAEFYAGKSVFITGGTGFLGKVFIEKLLYSCPDIGNIYMLIREKKGLS

VSERIKHFLDDPLFTRLKEKRPADLEKIVLIPGDITAPDLGITSENEKMLIEKVSVIIHSAA

TVKFNEPLPTAWKINVEGTRMMLALSRRMKRIEVFIHISTAYTNTNREVVDEILYPAPA

-continued

DIDQVHRYVKDGISEEETEKILNGRPNTYTFTKALTEHLVAENQAYVPTIIVRPSVVAAI

KDEPIKGWLGNWYGATGLTVFTAKGLNRVIYGHSSNIVDLIPVDYVANLVIAAGAKSSK

STELKVYNCCSSACNPITIGKLMSMFAEDAIKQKSYAMPLPGWYIFTKYKWLVLLLTILF

QVIPAYITDLYRHLIGKNPRYIKLQSLVNQTRSSIDFFTSHSWVMKADRVRELFASLSPA

DKYLFPCDPTDINWTHYIQDYCWGVRHFLEKKYR

SEQ ID NO: 7 - *S. cerevisiae*-codon-optimized nucleotide sequence of *H. armigera*
fatty acyl reductase; mRNA-coding sequence.
atggttgtcttgacctccaaagaaactaagccatctgttgctgaattttacgctggtaagtctgttttcattactggtggtactggt ttcttgggtaaggttttcattgaaaagttgttgtactcctgcccagatatcggtaatatctacatgttgatcagagaaaagaag ggtttgtccgtttccgaaagaatcaagcactttttggatgatcctttgttcaccagattgaaagaaaaaagaccagccgactt ggaaaagatcgttttgattccaggtgatattactgctccagatttgggtattacctccgaaaacgaaaagatgttgatcgaa aaggtcagtgtcattattcattctgctgctaccgttaagttcaacgaaccattgccaactgcttggaagattaacgttgaaggt actagaatgatgttggccttgtctagaagaatgaagagaatcgaagttttcatccatatctctaccgcttacactaacacca acagagaagttgttgacgaaatcttgtatccagctccagctgatattgatcaagttcacagatatgttaaggacggtatctct gaagaagaaactgaaaaaatcttgaacggtagaccaaacacttacactttcactaaggctttgaccgaacatttggttgct gaaaatcaagcttacgttccaaccattatcgttagaccatcagttgttgctgccattaaggatgaacctattaagggttggttg ggtaattggtatggtgctacaggtttgactgtttttactgctaagggtttgaacagagttatctacggtcactcttctaacatcgtt gatttgatcccagttgattacgttgccaacttggttattgctgctggtgctaaatcttctaagtctactgaattgaaggtctacaa ctgctgttcttctgcttgtaacccaattactatcggtaagttgatgtccatgtttgctgaagatgctatcaagcaaaagtcttacg ctatgccattgccaggttggtacatttttactaagtacaagtggttggtcttgttgttgaccattttgttccaagttattccagccta cattaccgacttgtacagacatttgattggtaagaacccaagatatatcaagttgcaatccttggtcaatcaaaccagatcc tccattgatttcttcacctctcattcttgggttatgaaggctgatagagtcagagaattattcgcttctttgtctccagcagataag tacttgtttccatgtgatccaaccgatattaactggacccattacattcaagattactgctggggtgttagacatttcttggaaa aaaaaagctacgaataa SEQ ID NO: 8 - *H.* armigera fatty acyl reductase
MVVLTSKETKPSVAEFYAGKSVFITGGTGFLGKVFIEKLLYSCPDIGNIYMLIREKKGLS

VSERIKHFLDDPLFTRLKEKRPADLEKIVLIPGDITAPDLGITSENEKMLIEKVSVIIHSAA

TVKFNEPLPTAWKINVEGTRMMLALSRRMKRIEVFIHISTAYTNTNREVVDEILYPAPA

DIDQVHRYVKDGISEEETEKILNGRPNTYTFTKALTEHLVAENQAYVPTIIVRPSVVAA

IKDEPIKGWLGNWYGATGLTVFTAKGLNRVIYGHSSNIVDLIPVDYVANLVIAAGAKSS

KSTELKVYNCCSSACNPITIGKLMSMFAEDAIKQKSYAMPLPGWYIFTKYKWLVLLLTIL

FQVIPAYITDLYRHLIGKNPRYIKLQSLVNQTRSSIDFFTSHSWVMKADRVRELFASLSP

ADKYLFPCDPTDINWTHYIQDYCWGVRHFLEKKSYE

SEQ ID NO: 9 - *S. cerevisiae*-codon-optimized nucleotide sequence of *H. armigera* fatty acyl reductase with signal peptide changed to HDEL; mRNA-coding sequence.
atggttgtcttgacctccaaagaaactaagccatctgttgctgaattttacgctggtaagtctgttttcattactggtggtactggt ttcttgggtaaggttttcattgaaaagttgttgtactcctgcccagatatcggtaatatctacatgttgatcagagaaaagaag ggtttgtccgtttccgaaagaatcaagcactttttggatgatcctttgttcaccagattgaaagaaaaaagaccagccgactt ggaaaagatcgttttgattccaggtgatattactgctccagatttgggtattacctccgaaaacgaaaagatgttgatcgaa aaggtcagtgtcattattcattctgctgctaccgttaagttcaacgaaccattgccaactgcttggaagattaacgttgaaggt actagaatgatgttggccttgtctagaagaatgaagagaatcgaagttttcatccatatctctaccgcttacactaacacca acagagaagttgttgacgaaatcttgtatccagctccagctgatattgatcaagttcacagatatgttaaggacggtatctct gaagaagaaactgaaaaaatcttgaacggtagaccaaacacttacactttcactaaggctttgaccgaacatttggttgct -continued gaaaatcaagcttacgttccaaccattatcgttagaccatcagttgttgctgccattaaggatgaacctattaagggttggttg ggtaattggtatggtgctacaggtttgactgttttactgctaagggtttgaacagagttatctacggtcactcttctaacatcgtt gatttgatcccagttgattacgttgccaacttggttattgctgctggtgctaaatcttctaagtctactgaattgaaggtctacaa ctgctgttcttctgcttgtaacccaattactatcggtaagttgatgtccatgtttgctgaagatgctatcaagcaaaagtcttacg ctatgccattgccaggttggtacattttactaagtacaagtggttggtcttgttgttgaccattttgttccaagttattccagccta cattaccgacttgtacagacatttgattggtaagaacccaagatatatcaagttgcaatccttggtcaatcaaaccagatcc tccattgatttcttcacctctcattcttgggttatgaaggctgatagagtcagagaattattcgcttctttgtctccagcagataag tacttgtttccatgtgatccaaccgatattaactggacccattacattcaagattactgctggggtgttagacatttcttggaac atgatgaattgtaa SEQ ID NO: 10 - *H. armigera* fatty acyl reductase with signal peptide changed to HDEL
MVVLTSKETKPSVAEFYAGKSVFITGGTGFLGKVFIEKLLYSCPD

STELKVYNCCSSACNPITIGKLMSMFAEDAIKQKSYAMPLPGWYVFTKYKWLVLLLTIL

FQVIPAYITDLYRHLIGKNPRYIKLQSLVNQTRSSIDFFTSHSWVMKADRVRELFASLSP

ADKYLFPCDPTDINWTHYIQDYCWGVRHFLEKKTTNK

SEQ ID NO: 13 - *S. cerevisiae*-codon-optimized nucleotide sequence of *H. assulta* fatty acyl reductase with signal peptide changed to HDEL; mRNA-coding sequence.
atggttgtcttgacctccaaagaaactaagccatctgttgctgaattttacgctggtaagtctgttttcattactggtggtactggt ttcttgggtaagatcttcattgaaagttgttgtactcctgcccagatatcggtaatatctacatgttgatcagagaaaagaag ggtttgtccgtttccgaaagaatcaagcaattttggatgacccttgttcaccagattgaaagaaaaaagaccagccgact tggaaaagatcgttttgattccaggtgatattactgctccagatttgggtattacctccgaaaacgaaaagatgttgatcgaa aaggtcagtgtcattattcattctgctgctaccgttaagttcaacgaaccattgccaactgcttggaagattaacgttgaaggt actgaatgatgttggccttgtctagaagaatgaagagaatcgaagttttcatccatatctctaccgcttacactaacaca acagagaagttgttgacgaaatcttgtatccagctccagctgatattgatcaagttcaccaatatgttaaggacggtatctct gaagaagaaactgaaaaaatcttgaacggtagaccaaacacttacactttcactaaggctttgaccgaacatttggttgct gaaaatcaagcttacgttccaaccattatcgttagaccatcagttgttgctgccattaaggatgaacctattaagggttggttg ggtaattggtatggtgctacaggtttgactgttttttactgctaagggtttgaacagagttatctacggtcattcctcttacatcgtt gatttgatcccagttgattacgttgccaacttggttattgctgctggtgctaaatcttctaagtctactgaattgaaggtctacaa ctgctgttcttctgcttgtaacccaattactatcggtaagttgatgtccatgtttgctgaagatgctatcaagcaaagtcttacg ctatgccattgccaggttggtatgttttacaaagtacaagtggttggtcttgttgttgaccattttgttccaagttattccagccta cattaccgacttgtacagacatttgattggtaagaacccaagatatatcaagttgcaatccttggtcaatcaaaccagatcc tccattgatttcttcacctctcattcttgggttatgaaggctgatagagtcagagaattattcgcttctttgtctccagcagataag tacttgtttccatgtgatccaaccgatattaactggacccattacattcaagattactgctggggtgttagacacttcttggaac atgatgaattgtaa SEQ ID NO: 14 - amino acid sequence of *H. assulta* fatty ac -continued

```
gatttgatcccagttgattacgttgccaacttggttattgctgctggtgctaaatcttctaagtctactgaattgaaggtctacaa ctgctgttcttctgcttgtaacccaattactatcggtaagttgatgtccatgtttgctgaagatgctatcaagcaaaagtcttacg ctatgccattgccaggttggtacattttactaagtacaagtggttggtcttgttgttgaccattttgttccaagttattccagccta cattaccgacttgtacagacatttgattggtaagaacccaagatatatcaagttgcaatccttggtcaatcaaaccagatcc tccattgatttcttcaccaaccattcttgggttatgaaggctgatagagtcagagaattattcgcttctttgtctccagcagataa gtacttgtttccatgtgatccagtcaacatcaattggagacaatatatccaagattactgctggggtgttagacatttcttggaa aaaaagacttaa
```

SEQ ID NO: 16 - Amino acid of H. subflexa fatty acyl reductase
MVVLTSKETKPSVAEFYAGKSVFITGGTGFLGKVFIEKLLYSCPDIGNIYMLIREKKGLS

VSERIKHFLDDPLFTRLKEKRPADLEKIVLIPGDITAPDLGITSENEKMLIEKVSVIIHSAA

TVKFNEPLPTAWKINVEGTRMMLALSRRMKRIEVFIHISTAYTNTNREVVDEILYPAPA

DIDQVHQYVKDGISEEETEKILNGRPNTYTFTKALTEHLVAENQAYVPTIIVRPSVVAA

IKDEPIKGWLGNWYGATGLTVFTAKGLNRVIYGHSSNIVDLIPVDYVANLVIAAGAKSS

KSTELKVYNCCSSACNPITIGKLMSMFAEDAIKQKSYAMPLPGWYIFTKYKWLVLLLTIL

FQVIPAYITDLYRHLIGKNPRYIKLQSLVNQTRSSIDFFTNHSWVMKADRVRELFASLSP

ADKYLFPCDPVNINWRQYIQDYCWGVRHFLEKKT

SEQ ID NO: 17 - S. cerevisiae-codon-optimized nucleotide sequence of H. subflexa
fatty acyl reductase with signal peptide changed to HDEL; mRNA-coding sequence.
```
atggttgtcttgacctccaaagaaactaagccatctgttgctgaattttacgctggtaagtctgttttcattactggtggtactggt ttcttgggtaaggttttcattgaaaagttgttgtactcctgcccagatatcggtaatatctacatgttgatcagagaaaagaag ggtttgtccgtttccgaaagaatcaagcacttttttggatgatcctttgttcaccagattgaaagaaaaaagaccagccgactt ggaaaagatcgttttgattccaggtgatattactgctccagatttgggtattacctccgaaaacgaaaagatgttgatcgaa aaggtcagtgtcattattcattctgctgctaccgttaagttcaacgaaccattgccaactgcttggaagattaacgttgaaggt actagaatgatgttggccttgtctagaagaatgaagagaatcgaagttttcatccatatctctaccgcttacactaacacca acagagaagttgttgacgaaatcttgtatccagctccagctgatattgatcaagttcaccaatatgttaaggacggtatctct gaagaagaaactgaaaaaatcttgaacggtagaccaaacacttacacttttcactaaggctttgaccgaacatttggttgct gaaaatcaagcttacgttccaaccattatcgttagaccatcagttgttgctgccattaaggatgaacctattaagggttggttg ggtaattggtatggtgctacaggtttgactgttttttactgctaagggtttgaacagagttatctacggtcactcttctaacatcgtt gatttgatcccagttgattacgttgccaacttggttattgctgctggtgctaaatcttctaagtctactgaattgaaggtctacaa ctgctgttcttctgcttgtaacccaattactatcggtaagttgatgtccatgtttgctgaagatgctatcaagcaaaagtcttacg ctatgccattgccaggttggtacattttactaagtacaagtggttggtcttgttgttgaccattttgttccaagttattccagccta cattaccgacttgtacagacatttgattggtaagaacccaagatatatcaagttgcaatccttggtcaatcaaaccagatcc tccattgatttcttcaccaaccattcttgggttatgaaggctgatagagtcagagaattattcgcttctttgtctccagcagataa gtacttgtttccatgtgatccagtcaacatcaattggagacaatatatccaagattactgctggggtgttagacatttcttgcat gatgaattgtaa
```

SEQ ID NO: 18 - amino acid sequence of H. subflexa fatty
acyl reductase with signal peptide changed to HDEL
MVVLTSKETKPSVAEFYAGKSVFITGGTGFLGKVFIEKLLYSCPDIGNIYMLIREKKGLS

VSERIKHFLDDPLFTRLKEKRPADLEKIVLIPGDITAPDLGITSENEKMLIEKVSVIIHSAA

TVKFNEPLPTAWKINVEGTRMMLALSRRMKRIEVFIHISTAYTNTNREVVDEILYPAPA

DIDQVHQYVKDGISEEETEKILNGRPNTYTFTKALTEHLVAENQAYVPTIIVRPSVVAA

IKDEPIKGWLGNWYGATGLTVFTAKGLNRVIYGHSSNIVDLIPVDYVANLVIAAGAKSS

KSTELKVYNCCSSACNPITIGKLMSMFAEDAIKQKSYAMPLPGWYIFTKYKWLVLLLTIL

FQVIPAYITDLYRHLIGKNPRYIKLQSLVNQTRSSIDFFTNHSWVMKADRVRELFASLSP

ADKYLFPCDPVNINWRQYIQDYCWGVRHFLHDEL

SEQ ID NO: 34 - Sc_FAA1 DNA sequence; mRNA-coding sequence.
ATGGTTGCTCAATATACCGTTCCAGTTGGGAAAGCCGCCAATGAGCATGAAACTG

CTCCAAGAAGAAATTATCAATGCCGCGAGAAGCCGCTCGTCAGACCGCCTAACAC

AAAGTGTTCCACTGTTTATGAGTTTGTTCTAGAGTGCTTTCAGAAGAACAAAAATTC

AAATGCTATGGGTTGGAGGGATGTTAAGGAAATTCATGAAGAATCCAAATCGGTTA

TGAAAAAAGTTGATGGCAAGGAGACTTCAGTGGAAAAGAAATGGATGTATTATGAA

CTATCGCATTATCATTATAATTCATTTGACCAATTGACCGATATCATGCATGAAATT

GGTCGTGGGTTGGTGAAAATAGGATTAAAGCCTAATGATGATGACAAATTACATCT

TTACGCAGCCACTTCTCACAAGTGGATGAAGATGTTCTTAGGAGCGCAGTCTCAA

GGTATTCCTGTCGTCACTGCCTACGATACTTTGGGAGAGAAAGGGCTAATTCATTC

TTTGGTGCAAACGGGGTCTAAGGCCATTTTTACCGATAACTCTTTATTACCATCCT

TGATCAAACCAGTGCAAGCCGCTCAAGACGTAAAATACATAATTCATTTCGATTCC

ATCAGTTCTGAGGACAGGAGGCAAAGTGGTAAGATCTATCAATCTGCTCATGATG

CCATCAACAGAATTAAAGAAGTTAGACCTGATATCAAGACCTTTAGCTTTGACGAC

ATCTTGAAGCTAGGTAAAGAATCCTGTAACGAAATCGATGTTCATCCACCTGGC

AAGGATGATCTTTGTTGCATCATGTATACGTCTGGTTCTACAGGTGAGCCAAAGG

GTGTTGTCTTGAAACATTCAAATGTTGTCGCAGGTGTTGGTGGTGCAAGTTTGAAT

GTTTTGAAGTTTGTGGGCAATACCGACCGTGTTATCTGTTTTTTGCCACTAGCTCA

TATTTTTGAATTGGTTTTCGAACTATTGTCCTTTTATTGGGGGCCTGCATTGGTTA

TGCCACCGTAAAAACTTTAACTAGCAGCTCTGTGAGAAATTGTCAAGGTGATTTGC

AAGAATTCAAGCCCACAATCATGGTTGGTGTCGCCGCTGTTTGGGAAACAGTGAG

AAAAGGGATCTTAAACCAAATTGATAATTTGCCCTTCCTCACCAAGAAAATCTTCTG

GACCGCGTATAATACCAAGTTGAACATGCAACGTCTCCACATCCCTGGTGGCGGC

GCCTTAGGAAACTTGGTTTTCAAAAAAATCAGAACTGCCACAGGTGGCCAATTAAG

ATATTTGTTAAACGGTGGTTCTCCAATCAGTCGGGATGCTCAGGAATTCATCACAA

ATTTAATCTGCCCTATGCTTATTGGTTACGGTTTAACCGAGACATGCGCTAGTACC

ACCATCTTGGATCCTGCTAATTTTGAACTCGGCGTCGCTGGTGACCTAACAGGTT

GTGTTACCGTCAAACTAGTTGATGTTGAAGAATTAGGTTATTTTGCTAAAAACAACC

AAGGTGAAGTTTGGATCACAGGTGCCAATGTCACGCCTGAATATTATAAGAATGA

GGAAGAAACTTCTCAAGCTTTAACAAGCGATGGTTGGTTCAAGACCGGTGACATC

GGTGAATGGGAAGCAAATGGCCATTTGAAAATAATTGACAGGAAGAAAAACTTGG

TCAAAACAATGAACGGTGAATATATCGCACTCGAGAAATTAGAGTCCGTTTACAGA

TCTAACGAATATGTTGCTAACATTTGTGTTTATGCCGACCAATCTAAGACTAAGCC

AGTTGGTATTATTGTACCAAATCATGCTCCATTAACGAAGCTTGCTAAAAAGTTGG

GAATTATGGAACAAAAAGACAGTTCAATTAATATCGAAAATTATTTGGAGGATGCA

AAATTGATTAAAGCTGTTTATTCTGATCTTTTGAAGACAGGTAAAGACCAAGGTTTG

GTTGGCATTGAATTACTAGCAGGCATAGTGTTCTTTGACGGCGAATGGACTCCAC

AAAACGGTTTTGTTACGTCCGCTCAGAAATTGAAAAGAAAAGACATTTTGAATGCT

GTCAAAGATAAAGTTGACGCCGTTTATAGTTCGTCTTAA

SEQ ID NO: 35 - Sc_FAA1 amino acid sequence
MVAQYTVPVGKAANEHETAPRRNYQCREKPLVRPPNTKCSTVYEFVLECFQKNKNS

NAMGWRDVKEIHEESKSVMKKVDGKETSVEKKWMYYELSHYHYNSFDQLTDIMHEI

GRGLVKIGLKPNDDDKLHLYAATSHKWMKMFLGAQSQGIPVVTAYDTLGEKGLIHSLV

QTGSKAIFTDNSLLPSLIKPVQAAQDVKYIIHFDSISSEDRRQSGKIYQSAHDAINRIKEV

RPDIKTFSFDDILKLGKESCNEIDVHPPGKDDLCCIMYTSGSTGEPKGVVLKHSNVVA

GVGGASLNVLKFVGNTDRVICFLPLAHIFELVFELLSFYWGACIGYATVKTLTSSSVRN

CQGDLQEFKPTIMVGVAAVWETVRKGILNQIDNLPFLTKKIFWTAYNTKLNMQRLHIPG

GGALGNLVFKKIRTATGGQLRYLLNGGSPISRDAQEFITNLICPMLIGYGLTETCASTTI

LDPANFELGVAGDLTGCVTVKLVDVEELGYFAKNNQGEVWITGANVTPEYYKNEEET

SQALTSDGWFKTGDIGEWEANGHLKIIDRKKNLVKTMNGEYIALEKLESVYRSNEYVA

NICVYADQSKTKPVGIIVPNHAPLTKLAKKLGIMEQKDSSINIENYLEDAKLIKAVYSDLL

KTGKDQGLVGIELLAGIVFFDGEWTPQNGFVTSAQKLKRKDILNAVKDKVDAVYSSS

SEQ ID NO: 36 - YI_FAA DNA sequence; mRNA-coding sequence.
```
        atggtcggat acacaatttc ctcaaagccc gtgtcggtgg aggtcggccc cgccaagcct
  61 ggcgagactg ccccccgacg aaacgtcatt gccaaggacg ccctgtcgt cttccccgac
 121 aacgactcgt ccctgaccac cgtctacaag ctgttcaaaa agtacgccga atcaacagc
 181 gagcgaaagg ccatgggatg gcgagacacc atcgacatcc acgtggagac caaacaggtg
 241 accaaggtcg tggacggagt ggagaagaag gtgcccaagg aatggaagta ctttgagatg
 301 ggcccttaca agtggctctc atacaaggag gcccttaagc tggtccatga ttatggagct
 361 ggtcttcgac acctcggaat caagcccaag gagaagatgc acatttacgc ccagacctcc
 421 caccgatgga tgctctctgg cctggcttct ctgtctcagg gtattcccat tgtcactgcc
 481 tacgacactc ttggagagga gggtctcact cgatctctcc aggagaccaa ctcggtcatc
 541 atgtttaccg acaaggctct gctgagctct ctcaaggtct ctctcaagaa gggcaccgat
 601 ctgcgaatca tcatctacgg aggtgatctg accccgacg acaagaaggc cggaaacacg
 661 gagattgacg ccatcaagga gattgttcca gatatgaaga tctacaccat ggacgaggtt
 721 gtcgctctcg gccgagaaca cccccacccc gtggaggagg tcgactatga ggacctggcc
 781 ttcatcatgt acacctctgg ttctaccggt gtccccaagg gtgtggttct gcagcacaag
 841 cagatcctcg cctctgtggc cggtgtcacc aagatcattg accgatctat catcggcaac
 901 acagaccggc ttctcaactt cctgcccctc gcacacattt cgagtttgt gttcgagatg
 961 gtcaccttct ggtggggtgc ttctctgggt acggaaccg tcaagaccat tccgatctg
1021 tccatgaaga actgtaaggg agacattcga gagctcaagc ccaccatcat ggtcggcgtt
1081 cccgctgtct gggaacctat gcgaaagggt attcttggca agatcaagga gctgtctcct
1141 ctgatgcagc gggtcttctg ggcctcattt gccgccaagc agcgtctcga cgagaacgga
1201 ctccctggtg gatctatcct cgactcgctc attttcaaga aggtcaagga cgccactgga
1261 ggctgtctcc gatacgtgtg taacggaggt gctccagtat ctgtcgacac ccagaagttc
1321 atcaccactc tcatctgtcc catgctgatt ggatgcggtc tgaccgagac tacagccaac
1381 accaccatca tgtcgcctaa atcgtacgcc tttggcacca ttggtgagcc caccgccgcc
1441 gtgaccctca agctcattga cgtgcctgaa gccggctact cgccgagaa caaccaggga
1501 gagctgtgca tcaagggcaa cgtcgtgatg aaggagtact acaagaacga ggaggagacc
1561 aagaaggcgt tctccgacga tggctatttc ctcaccggtg atattgccga gtggaccgcc
```

```
1621 aatggccagc tcagaatcat tgaccgacga aagaacctcg tcaagaccca gaacggagag 1681 tacattgctc tggagaagct cgagacacag taccgatcgt cgtcgtacgt ggccaacctg 1741 tgtgtgtacg ccgaccagaa ccgagtcaag cccattgctc tggtcattcc taacgagggc 1801 cccaccaaga agcttgccca gagcttgggc gtcgattctg acgactggga cgccgtctgt 1861 tccaacaaaa aggtggtcaa ggctgtgctc aaggacatgc tcgataccgg ccgatctctg 1921 ggtctgtccg gcattgagct gctgcaaggc attgtgttgc tgcctggcga gtggactcct 1981 cagaacagct acctgactgc tgcccagaag ctcaaccgaa agaagattgt ggatgataac 2041 aagaaggaaa ttgatgagtg ctacgagcag tcttag
```

SEQ ID NO: 37 - YI_FAA amino acid sequence
MVGYTISSKPVSVEVGPAKPGETAPRRNVIAKDAPVVFPDNDSSLTTVYKLFKKYAEIN

SERKAMGWRDTIDIHVETKQVTKVVDGVEKKVPKEWKYFEMGPYKWLSYKEALKLV

HDYGAGLRHLGIKPKEKMHIYAQTSHRWMLSGLASLSQGIPIVTAYDTLGEEGLTRSL

QETNSVIMFTDKALLSSLKVSLKKGTDLRIIIYGGDLTPDDKKAGNTEIDAIKEIVPDMKI

YTMDEVVALGREHPHPVEEVDYEDLAFIMYTSGSTGVPKGVVLQHKQILASVAGVTKII

DRSIIGNTDRLLNFLPLAHIFEFVFEMVTFWWGASLGYGTVKTISDLSMKNCKGDIREL

KPTIMVGVPAVWEPMRKGILGKIKELSPLMQRVFWASFAAKQRLDENGLPGGSILDSL

IFKKVKDATGGCLRYVCNGGAPVSVDTQKFITTLICPMLIGCGLTETTANTTIMSPKSYA

FGTIGEPTAAVTLKLIDVPEAGYFAENNQGELCIKGNVVMKEYYKNEEETKKAFSDDG

YFLTGDIAEWTANGQLRIIDRRKNLVKTQNGEYIALEKLETQYRSSSYVANLCVYADQN

RVKPIALVIPNEGPTKKLQSLGVDSDDWDAVCSNKKVVKAVLKDMLDTGRSLGLSGIE

LLQGIVLLPGEWTPQNSYLTAAQKLNRKKIVDDNKKEIDECYEQS

SEQ ID NO: 38: *Saccharomyces cerevisiae* ATF1 DNA
sequence; mRNA-coding sequence.
```
ATGAATGAAA TCGATGAGAA AAATCAGGCC CCCGTGCAAC AAGAATGCCT

GAAAGAGATG ATTCAGAATG GCATGCTCG GCGTATGGGA TCTGTTGAAG

ATCTGTATGT TGCTCTCAAC AGACAAAACT TATATCGAAA CTTCTGCACA

TATGGAGAAT TGAGTGATTA CTGTACTAGG GATCAGCTCA CATTAGCTTT

GAGGGAAATC TGCCTGAAAA ATCCAACTCT TTTACATATT GTTCTACCAA

CAAGATGGCC AAATCATGAA AATTATTATC GCAGTTCCGA ATACTATTCA

CGGCCACATC CAGTGCATGA TTATATTTCA GTATTACAAG AATTGAAACT

GAGTGGTGTG GTTCTCAATG AACAACCTGA GTACAGTGCA GTAATGAAGC

AAATATTAGA GAATTCAAA ATAGTAAGG GTTCCTATAC TGCAAAAATT

TTTAAACTTA CTACCACTTT GACTATTCCT TACTTTGGAC CAACAGGACC

GAGTTGGCGG CTAATTTGTC TTCCAGAAGA GCACACAGAA AAGTGGAAAA

AATTTATCTT TGTATCTAAT CATTGCATGT CTGATGGTCG GTCTTCGATC

CACTTTTTC ATGATTTAAG AGACGAATTA ATAATATTA AAACTCCACC

AAAAAAATTA GATTACATTT TCAAGTACGA GGAGGATTAC CAATTATTGA

GGAAACTTCC AGAACCGATC GAAAAGGTGA TAGACTTTAG ACCACCGTAC

TTGTTTATTC CGAAGTCACT TCTTTCGGGT TTCATCTACA ATCATTTGAG

ATTTTCTTCA AAAGGTGTCT GTATGAGAAT GGATGATGTG GAAAAAACCG

ATGATGTTGT CACCGAGATC ATCAATATTT CACCAACAGA ATTTCAAGCG

ATTAAAGCAA ATATTAAATC AAATATCCAA GGTAAGTGTA CTATCACTCC
```

-continued

```
GTTTTTACAT GTTTGTTGGT TTGTATCTCT TCATAAATGG GGTAAATTTT

TCAAACCATT GAACTTCGAA TGGCTTACGG ATATTTTTAT CCCCGCAGAT

TGCCGCTCAC AACTACCAGA TGATGATGAA ATGAGACAGA TGTACAGATA

TGGCGCTAAC GTTGGATTTA TTGACTTCAC CCCCTGGATA AGCGAATTTG

ACATGAATGA TAACAAAGAA AATTTTTGGC CACTTATTGA GCACTACCAT

GAAGTAATTT CGGAAGCTTT AAGAAATAAA AAGCATCTCC ATGGCTTAGG

GTTCAATATA CAAGGCTTCG TTCAAAAATA TGTGAACATT GACAAGGTAA

TGTGCGATCG TGCCATCGGG AAAAGACGCG GAGGTACATT GTTAAGCAAT

GTAGGTCTGT TTAATCAGTT AGAGGAGCCC GATGCCAAAT ATTCTATATG

CGATTTGGCA TTTGGCCAAT TTCAAGGATC CTGGCACCAA GCATTTTCCT

TGGGTGTTTG TTCGACTAAT GTAAAGGGGA TGAATATTGT TGTTGCTTCA

ACAAAGAATG TTGTTGGTAG TCAAGAATCT CTCGAAGAGC TTTGCTCCAT

TTACAAAGCT CTCCTTTTAG GCCCTTAG
```

SEQ ID NO: 39: *Saccharomyces cerevisiae* Atf1 amino acid sequence
```
MNEIDEKNQAPVQQECLKEMIQNGHARRMGSVEDLYVALNRQNLYRNFCTYGELSD

YCTRDQLTLALREICLKNPTLLHIVLPTRWPNHENYYRSSEYYSRPHPVHDYISVLQEL

KLSGVVLNEQPEYSAVMKQILEEFKNSKGSYTAKIFKLTTTLTIPYFGPTGPSWRLICLP

EEHTEKWKKFIFVSNHCMSDGRSSIHFFHDLRDELNNIKTPPKKLDYIFKYEEDYQLLR

KLPEPIEKVIDFRPPYLFIPKSLLSGFIYNHLRFSSKGVCMRMDDVEKTDDVVTEIINISP

TEFQAIKANIKSNIQGKCTITPFLHVCWFVSLHKWGKFFKPLNFEWLTDIFIPADCRSQL

PDDDEMRQMYRYGANVGFIDFTPWISEFDMNDNKENFWPLIEHYHEVISEALRNKKH

LHGLGFNIQGFVQKYVNIDKVMCDRAIGKRRGGTLLSNVGLFNQLEEPDAKYSICDLA

FGQFQGSWHQAFSLGVCSTNVKGMNIVVASTKNVVGSQESLEELCSIYKALLLGP
```

SEQ ID NO: 40: Sl_Δ11-desaturase DNA sequence; mRNA-coding sequence.
```
GGACACTGACATGGACTGAAGGAGTAGAGAATCGGCCCGTGGAGTTGGCCTTCA

TTTTCAGTCTTATCTCTCGGTGTTATGGTAGTCACTTATATCGGTATTAAAATAAGT

GAATAAGGCTTGTAAAAATGGCGCAATGTGTACAAACAACAACGATTTTGGAACAA

AAAGAAGAGAAAACAGTAACTTTGCTGGTACCTCAAGCGGGAAAGAGGAAGTTTG

AAATTGTGTATTTTAATATCATCACCTTCGCTTACTGGCATATAGCTGGACTATATG

GCCTTTATTTGTGCTTCACTTCAACAAAATGGGCGACAGTTTTATTCTCATTCTTTC

TATTCGTCGTAGCAGAAGTAGGGGTCACGGCTGGCTCCCACAGACTTTGGTCGCA

TAAAACTTACAAAGCAAAACTACCTTTACAAATTCTGCTAATGGTGATGAATTCCCT

TGCATTTCAAAACACAGTCATTGATTGGGTGAGAGACCATCGACTCCATCATAAGT

ATAGCGACACTGATGCCGATCCCCATAATGCCTCCCGAGGATTTTTCTATTCGCAC

GTCGGTTGGCTGCTTGTGAGAAAACACCCTGATGTCAAGAAACGAGGAAAGGAAA

TTGATATATCTGATATTTACAACAATCCGGTACTGAGGTTCCAGAAGAAGTACGCA

ATTCCTTTCATCGGGGCAGTTTGTTTCGTCTTACCAACATTGATACCGGTTTACGG

TTGGGGAGAAACCTGGACTAATGCCTGGCACGTCGCCATGCTGCGGTACATTATG

AACCTTAACGTCACCTTCCTGGTCAACAGCGCTGCTCATATATATGGAAAGAGACC

TTATGACAAGAAGATCCTACCATCTCAAAACATAGCTGTGTCCATTGCAACCTTTG

GGGAAGGTTTCCATAATTATCATCATGTATTTCCATGGGATTATCGCGCAGCTGAA
```

```
CTTGGAAATAACAGTTTGAATTTCCCTACGAAATTTATTGATTTCTTTGCGTGGATC

GGATGGGCGTATGACCTAAAGACTGTTTCGAAAGAAATGATAAAACAAAGGTCAA

AAAGAACTGGTGATGGAACTAATCTATGGGGGTTAGAAGATGTGGATACCCCGGA

GGATTTAAAAAATACAAAAGGCGAATAGGCAAACCCTTAAACTCAAACAGTGAGGT

TTAATGTGATATTTAGAATTAGAATTAATTTATTTGAAATTAAATGAAGGTTTTGGAT

AACTGTTTTAATAATAAAAATAGTTTTTCGATTAAATTCCTTAGATTATTTTAAAGG

AAATGTATAAGGTACTCGCGTGGTTAGCAACCCAGCAGTCCCTGTTTATCTGTTTT

TATGAATTTATTCTATGAATGTAGATGTCGCATGAAATTTTAAAATGTTGCATTTGTA

TAATTTTACTTATGAATAAATAAATTTATTTTTAAAAAAAAAAAAAAAAAAAAAAAAA

AAAAAAAA

SEQ ID NO: 41: Sl_Δ11-desaturase amino acid sequence
MAQCVQTTTILEQKEEKTVTLLVPQAGKRKFEIVYFNIITFAYWHIAGLYGLYLCFTSTK

WATVLFSFFLFVVAEVGVTAGSHRLWSHKTYKAKLPLQILLMVMNSLAFQNTVIDWVR

DHRLHHKYSDTDADPHNASRGFFYSHVGWLLVRKHPDVKKRGKEIDISDIYNNPVLRF

QKKYAIPFIGAVCFVLPTLIPVYGWGETWTNAWHVAMLRYIMNLNVTFLVNSAAHIYGK

RPYDKKILPSQNIAVSIATFGEGFHNYHHVFPWDYRAAELGNNSLNFPTKFIDFFAWIG

WAYDLKTVSKEMIKQRSKRTGDGTNLWGLEDVDTPEDLKNTKGE

SEQ ID NO: 42: Ase_Δ11-desaturase DNA sequence;
mRNA-coding sequence.
ATGGCTCAAGGTGTCCAAACAACTACGATATTGAGGGAGGAAGAGCCGTCATTGA

CTTTCGTGGTACCTCAAGAACCGAGAAAGTATCAAATCGTGTACCCAAACCTTATC

ACATTTGGGTACTGGCATATAGCTGGTTTATACGGGCTATATTTGTGCTTTACTTC

GGCAAAATGGCAAACAATTTTATTCAGTTTCATGCTCGTTGTGTTAGCAGAGTTGG

GAATAACAGCCGGCGCTCACAGGTTATGGGCCCACAAAACATATAAAGCGAAGCT

TCCCTTACAAATTATCCTGATGATACTGAACTCCATTGCCTTCCAAAATTCCGCCAT

TGATTGGGTGAGGGACCACCGTCTCCATCATAAGTACAGTGACACTGATGCAGAC

CCTCACAATGCTACTCGTGGTTTCTTCTATTCTCATGTTGGATGGTTGCTCGTAAG

AAAACATCCAGAAGTCAAGAGACGTGGAAAGGAACTTGACATGTCTGATATTTACA

ACAATCCAGTGCTGAGATTTCAAAAGAAGTATGCTATACCCTTCATCGGGGCAATG

TGCTTCGGATTACCAACTTTTATCCCTGTTTACTTCTGGGGAGAAACCTGGAGTAA

TGCTTGGCATATCACCATGCTTCGGTACATCCTCAACCTAAACATTACTTTCCTGG

TCAACAGTGCTGCTCATATCTGGGGATACAAACCTTATGACATCAAAATATTGCCT

GCCCAAAATATAGCAGTTTCCATAGTAACCGGCGGCGAAGTTTCCATAACTACCA

CCACGTTTTTTCCTTGGGATTATCGTGCAGCAGAATTGGGGAACAATTATCTTAAT

TTGACGACTAAGTTCATAGATTTCTTCGCTTGGATCGGATGGGCTTACGATCTTAA

GACGGTGTCCAGTGATGTTATAAAAAGTAAGGCGGAAAGAACTGGTGATGGGACG

AATCTTTGGGGTTTAGAAGACAAAGGTGAAGAAGATTTTTTGAAAATCTGGAAAGA

CAATTAA

SEQ ID NO: 43: Ase_Δ11-desaturase amino acid sequence
MAQGVQTTTILREEEPSLTFVVPQEPRKYQIVYPNLITFGYWHIAGLYGLYLCFTSAKW

QTILFSFMLVVLAELGITAGAHRLWAHKTYKAKLPLQIILMILNSIAFQNSAIDWVRDHRL

HHKYSDTDADPHNATRGFFYSHVGWLLVRKHPEVKRRGKELDMSDIYNNPVLRFQK
```

KYAIPFIGAMCFGLPTFIPVYFWGETWSNAWHITMLRYILNLNITFLVNSAAHIWGYKPY

DIKILPAQNIAVSIVTGGEVSITTTTFFPWDYRAAELGNNYLNLTTKFIDFFAWIGWAYDL

KTVSSDVIKSKAERTGDGTNLWGLEDKGEEDFLKIWKDN

SEQ ID NO: 44: Tni_Δ11-desaturase DNA sequence;
mRNA-coding sequence.
ATGGCTGTGATGGCTCAAACAGTACAAGAAACGGCTACAGTGTTGGAAGAGGAAG

CTCGCACAGTGACTCTTGTGGCTCCAAAGACAACGCCAAGGAAATATAAATATATA

TACACCAACTTTCTTACATTTTCATATGCGCATTTAGCTGCATTATACGGACTTTAT

TTGTGCTTCACCTCTGCGAAATGGGAAACATTGCTATTCTCTTTCGTACTCTTCCA

CATGTCAAATATAGGCATCACCGCAGGGGCTCACCGACTCTGGACTCACAAGACT

TTCAAAGCCAAATTGCCTTTGGAAATTGTCCTCATGATATTCAACTCTTTAGCCTTT

CAAAACACGGCTATTACATGGGCTAGAGAACATCGGCTACATCACAAATACAGCG

ATACTGATGCTGATCCCCACAATGCGTCAAGAGGGTTCTTCTACTCGCATGTTGG

CTGGCTATTAGTAAAAAAACATCCCGATGTCCTGAAATATGGAAAAACTATAGACA

TGTCGGATGTATACAATAATCCTGTGTTAAAATTTCAGAAAAAGTACGCAGTACCC

TTAATTGGAACAGTTTGTTTTGCTCTTCCAACTTTGATTCCAGTCTACTGTTGGGGC

GAATCGTGGAACAACGCTTGGCACATAGCCTTATTTCGATACATATTCAATCTTAA

CGTGACTTTCCTAGTCAACAGTGCTGCGCATATCTGGGGAATAAGCCTTATGAT

AAAAGCATCTTGCCCGCTCAAAACCTGCTGGTTTCCTTCCTAGCAAGTGGAGAAG

GCTTCCATAATTACCATCACGTCTTTCCATGGGATTACCGCACAGCAGAATTAGGG

AATAACTTCCTGAATTTGACGACGCTGTTCATTGATTTTTGTGCCTGGTTTGGATG

GGCTTATGACTTGAAGTCTGTATCAGAGGATATTATAAAACAGAGAGCTAAACGAA

CAGGTGACGGTTCTTCAGGGGTCATTTGGGGATGGGACGACAAAGACATGGACC

GCGATATAAAATCTAAAGCTAACATTTTTTATGCTAAAAAGGAATGA

SEQ ID NO: 45: Tni_Δ11-desaturase amino acid sequence
MAVMAQTVQETATVLEEEARTVTLVAPKTTPRKYKYIYTNFLTFSYAHLAALYGLYLCF

TSAKWETLLFSFVLFHMSNIGITAGAHRLWTHKTFKAKLPLEIVLMIFNSLAFQNTAITW

AREHRLHHKYSDTDADPHNASRGFFYSHVGWLLVKKHPDVLKYGKTIDMSDVYNNP

VLKFQKKYAVPLIGTVCFALPTLIPVYCWGESWNNAWHIALFRYIFNLNVTFLVNSAAHI

WGNKPYDKSILPAQNLLVSFLASGEGFHNYHHVFPWDYRTAELGNNFLNLTTLFIDFC

AWFGWAYDLKSVSEDIIKQRAKRTGDSSGVIWGWDDKDMRDIKSKANIFYAKKE

SEQ ID NO: 45: Sc_FAA DNA sequence; mRNA coding sequence
atggccgctccagattatgcacttaccgatttaattgaatcggatcctcgtttcgaaagtttgaagacaagattagccggtta caccaaaggctctgatgaatatattgaagagctatactctcaattaccactgaccagctaccccaggtacaaaacattttta aagaaacaggcggttgccatttcgaatccggataatgaagctggtttagctcgatttataggagttctctttcttctgaaaatc tagtgagctgtgtggataaaaacttaagaactgcatacgatcacttcatgttttctgcaaggagatggcctcaacgtgactgt ttaggttcaaggccaattgataaagccacaggcacctgggaggaaacattccgtttcgagtcgtactccacggtatctaa aagatgtcataatatcggaagtggtatattgtctttggtaaacacgaaaaggaaacgtccttggaagcaatgattttgttgt tgctatcttatcacacaacaaccctgaatggatcctaacagatttggcctgtcaggctattctctaactaacacggctttgta cgaaacattaggtccaaacacctccgagtacatattgaatttaaccgaggcccccattctgattttttgcaaaatcaaatatgt atcatgtattgaagatggtgcctgatatgaaatttgttaatactttggtttgtatggatgaattaactcatgacgagctccgtatg ctaaatgaatcgttgctacccgttaagtgcaactctctcaatgaaaaaatcacatttttttcattggagcaggtagaacaagtt ggttgctttaacaaaattcctgcaattccacctaccccagattccttgtatactatttcgtttacttctggtactacaggtttaccta -continued

```
aaggtgtggaaatgtctcacagaaacattgcgtctgggatagcatttgcttttctaccttcagaataccgccagataaaag aaaccaacagttatatgatatgtgttttttgccattggctcatattttgaaagaatggttattgcgtatgatctagccatcgggttt ggaataggcttcttacataaaccagacccaactgtattggtagaggatttgaagattttgaaaccttacgcggttgccctggt tcctagaatattaacacggtttgaagccggtataaaaaatgctttggataaatcgactgtccagaggaacgtagcaaata ctatattggattctaaatcggccagatttaccgcaagaggtggtccagataaatcgattatgaattttctagtttatcatcgcgt attgattgataaaatcagagactctttaggtttgtccaataactcgtttataattaccggatcagctcccatatctaaagatacc ttactattttaagaagcgccttggatattggtataagacagggctacggcttaactgaaacttttgctggtgtctgtttaagcg aaccgtttgaaaaagatgtcggatcttgtggtgccataggtatttctgcagaatgtagattgaagtctgttccagaaatgggtt accatgccgacaaggatttaaaaggtgaactgcaaattcgtggcccacaggttttgaaagatattttaaaaatccgaatg aaacttcaaaagccgttgaccaagatggttggttttccacgggagatgttgcatttatcgatgcaaaaggtcgcatcagcgt cattgatcgagtcaagaacttttcaagctagcacatggtgaatatattgctccagagaaaatcgaaatatttatttatcatc atgcccctatatcacgcaaatatttgtctttggagatcctttgaagacatttttagttggcatcgttggtgttgatgttgatgcagc gcaaccgattttagctgcaaagcacccagaggtgaaaacgtggactaaggaagtgctagtagaaaacttaaatcgtaa taaaaagctaaggaaggaatttttaaacaaaattaataaatgcatcgatgggctacaaggatttgaaaaattgcacaac atcaaagtcggacttgagcctttgactctcgaggatgatgttgtgacgccaacttttaaaataaagcgtgccaaagcatca aaattcttcaaagatacattagaccaactatacgccgaaggttcactagtcaagacagaaaagctttag
```

SEQ ID NO: 47: Sc_FAA2 amino acid sequence
MAAPDYALTDLIESDPRFESLKTRLAGYTKGSDEYIEELYSQLPLTSYPRYKTFLKKQA

VAISNPDNEAGFSSIYRSSLSSENLVSCVDKNLRTAYDHFMFSARRWPQRDCLGSRPI

DKATGTWEETFRFESYSTVSKRCHNIGSGILSLVNTKRKRPLEANDFVVAILSHNNPE

WILTDLACQAYSLTNTALYETLGPNTSEYILNLTEAPILIFAKSNMYHVLKMVPDMKFVN

TLVCMDELTHDELRMLNESLLPVKCNSLNEKITFFSLEQVEQVGCFNKIPAIPPTPDSL

YTISFTSGTTGLPKGVEMSHRNIASGIAFAFSTFRIPPDKRNQQLYDMCFLPLAHIFER

MVIAYDLAIGFGIGFLHKPDPTVLVEDLKILKPYAVALVPRILTRFEAGIKNALDKSTVQR

NVANTILDSKSARFTARGGPDKSIMNFLVYHRVLIDKIRDSLGLSNNSFIITGSAPISKDT

LLFLRSALDIGIRQGYGLTETFAGVCLSEPFEKDVGSCGAIGISAECRLKSVPEMGYHA

DKDLKGELQIRGPQVFERYFKNPNETSKAVDQDGWFSTGDVAFIDAKGRISVIDRVKN

FFKLAHGEYIAPEKIENIYLSSCPYITQIFVFGDPLKTFLVGIVGVDVDAAQPILAAKHPE

VKTWTKEVLVENLNRNKKLRKEFLNKINKCIDGLQGFEKLHNIKVGLEPLTLEDDVVTP

TFKIKRAKASKFFKDTLDQLYAEGSLVKTEKL

REFERENCES

Alfaro, Navarro-Llopis, Primo, 2009. Optimization of pheromone dispenser density for managing the rice striped stem borer, *Chilo suppressalis* (Walker), by mating disruption. Crop Protection. 28:567-572.

Angerer, Radermacher, Mankowska, Steger, Zwicker, Heide, Wittig, Brandt, Zickermann, 2014. The LYR protein subunit NB4M/NDUFA6 of mitochondrial complex I anchors an acyl carrier protein and is essential for catalytic activity. PNAS. 111(14)

Bari, 2003. Development of pheromone mating disruption strategies for the suppression of the artichoke plume moth in artichokes grown on the central coast of California. ISHS Acta Horticulturae 660: V International Congress on Artichoke. doi: 10.17660/ActaHortic.2004.660.80

Chen, Beckerich, Gaillardin, 1997. One-step transformation of the dimorphic yeast *Yarrowia lipolytica*. Appl Microbiol Biotechnol. 48(2):232-5

Eizaguirre, Sans, López, Albajes. 2002. Effects of mating disruption against the Mediterranean corn borer, *Sesamia nonagrioides*, on the European corn borer *Ostrinia nubilalis*. Use of pheromones and other semiochemicals in integrated production IOBC wprs Bulletin.

Ferrell, Yao, 1972. Reductive and oxidative synthesis of saturated and unsaturated fatty aldehydes, J Lipid Res. 13(1):23-6).

Gietz R D & Schiestl R H, 2007. Quick and easy yeast transformation using the LiAc/SS carrier DNA/PEG method. Nat Protoc 2: 35-37.

Hagström, Wang, Liénard, Lassance, Johansson, Löfstedt, 2013. A moth pheromone brewery: production of (Z)-11-hexadecenol by heterologous co-expression of two biosynthetic genes from a noctuid moth in a yeast cell factory. Microbial Cell Factories 12:125

Jensen, Strucko, Kildegaard, David, Maury, Mortensen, Forster, Nielsen, Borodina, 2014. EasyClone: method for iterative chromosomal integration of multiple genes in *Saccharomyces cerevisiae*, FEMS Yeast Res. 14(2):238-48

Kehat, Dunkelblum, 1993. Sex Pheromones: achievements in monitoring and mating disruption of cotton pests in Israel, Achieves of Insect Biochemistry and Physiology. 22:425-431.

Li, Zhang, 2009. An environmentally benign TEMPO-catalyzed efficient alcohol oxidation system with a recyclable hypervalent iodine(III) reagent andilts facile preparation. Synthesis, 1163-1169a.

Maury, Germann, Baallal Jacobsen, Jensen, Kildegaard, Herrgård, Schneider, Koza, Forster, Nielsen, Borodina, 2016. EasyCloneMulti: A Set of Vectors for Simultaneous and Multiple Genomic Integrations in *Saccharomyces cerevisiae*. PLoS One. 11(3):e0150394

Meyer, Schreiber, 1994. Acceleration of the Dess-Martin oxidation by water J. Org. Chem., 59, 7549-7552;

Okada, Asawa, Sugiyama, Kirihara, Iwai, Kimura, 2014. Sodium hypochlorite pentahydrate (NaOCl.5H2O) crystals as an extraordinary oxidant for primary and secondary alcohols. Synlett, 25, 596-598.

Stovicek, Borja, Forster, Borodina, 2015. EasyClone 2.0: expanded toolkit of integrative vectors for stable gene expression in industrial *Saccharomyces cerevisiae* strains. J Ind Microbiol Biotechnol, 42, 1519-31

Tamura, Aoyama, Takido, Kodomari, 2012. Novel [4-Hydroxy-TEMPO+NaCl]/SiO2 as a reusable catalyst for aerobic oxidation of alcohols to carbonyls. Synlett, 23, 1397-1407.

Yadav, Reddy, Basak, Narsaiah, 2004. Recyclable 2nd generation ionic liquids as green solvents for the oxidation of alcohols with hypervalent iodine reagents, Tetrahedron, 60, 2131-2135.

Wu, Zhang, Yao, Xu, Wang and Zhang, 2012. Management of diamondback moth, *Plutella xylostella* (Lepidoptera: Plutellidae) by mating disruption. Insect Science 19 (6), 643-648.

The invention claimed is:

1. A method for production of a moth pheromone in a yeast cell, said method comprising the steps of:
   i) providing a yeast cell capable of synthesizing hexadecanoyl-CoA, said yeast cell expressing:
   a Δ11-desaturase selected from the group consisting of a Δ11-desaturase comprising SEQ ID NO: 2, a Δ11-desaturase comprising SEQ ID NO: 41, a Δ11-desaturase comprising SEQ ID NO: 43, and a Δ11-desaturase comprising SEQ ID NO: 45, and an alcohol-forming fatty acyl-CoA reductase (FAR) selected from the group consisting of a FAR comprising SEQ ID NO: 8, a FAR comprising SEQ ID NO: 16, and a FAR comprising SEQ ID NO: 12;

ii) expressing said Δ11-desaturase and said FAR from said yeast cell; and iii) incubating said yeast cell in a medium, whereby the Δ11-desaturase is capable of converting at least part of said hexadecanoyl-CoA to (Z)11-hexadecenoyl-CoA; and said FAR is capable of converting at least part of said (Z)11-hexadecenoyl-CoA to (Z)-11-hexadecen-1-ol, thereby obtaining a moth pheromone comprising (Z)-11-hexadecen-1-ol with a titre of at least 1 mg/L, wherein the titre is measured in a culture medium after culturing the yeast cell.

2. The method of claim 1, wherein the genus of said yeast cell is selected from the group consisting of *Saccharomyces, Pichia, Yarrowia, Kluyveromyces, Candida, Rhodotorula, Rhodosporidium, Cryptococcus, Trichosporon* and *Lipomyces*.

3. The method of claim 1, wherein the yeast is selected from the group consisting of *Saccharomyces cerevisiae, Pichia pastoris, Kluyveromyces marxianus, Cryptococcus albidus, Lipomyces lipofera, Lipomyces starkeyi, Rhodosporidium toruloides, Rhodotorula glutinis, Trichosporon pullulan* and *Yarrowia lipolytica*.

4. The method of claim 1, wherein the yeast is further capable of expressing a fatty acyl-CoA synthetase (FAA).

5. The method of claim 4, wherein the FAA is selected from the group consisting of a FAA comprising SEQ ID NO: 35, a FAA comprising SEQ ID NO: 37, and a FAA variant having at least 85% sequence identity to the polypeptide of SEQ ID NO: 35 or SEQ ID NO: 37, said variant having fatty acyl-CoA synthetase activity.

6. The method of claim 1, further comprising the step of converting at least part of the produced (Z)-11-hexadecen-1-ol into (Z)-11-hexadecen-1-yl acetate by expression of an acetyltransferase or by chemical conversion.

7. The method of claim 6, wherein the acetyltransferase is a heterologous acetyltransferase (AcT) expressed from said yeast cell or a native acetyltransferase overexpressed from said yeast cell compared to the native expression levels of said native acetyltransferase in said yeast cell, wherein said acetyltransferase is capable of converting at least part of the (Z)-11-hexadecen-1-ol into (Z)11-hexadecen-1-yl acetate, thereby further producing (Z)11-hexadecen-1-yl acetate.

8. The method of claim 6, wherein the acetyltransferase is selected from the group consisting of an acetyltransferase comprising SEQ ID NO: 39 and (ii) an acetyltransferase variant having at least 85% sequence identity to the polypeptide of SEQ ID NO: 39, said variant having acetyltransferase activity.

9. The method of claim 1, wherein:

The Δ11-desaturase is encoded by a nucleic acid sequence identical to or having at least 85% identity to SEQ ID NO: 1, SEQ ID NO: 40, SEQ ID NO: 42 or SEQ ID NO: 44; and/or The FAR is encoded by a nucleic acid sequence identical to or having at least 90% identity to SEQ ID NO: 7, at least 90% identity to SEQ ID NO: 11 or at least 90% identity to SEQ ID NO: 15 or 100% identity to SEQ ID NO: 7, SEQ ID NO: 11 or SEQ ID NO: 15.

10. The method of claim 1, further comprising the step of converting at least part of the produced (Z)-11-hexadecen-1-ol into (Z)-11-hexadecenal by a step of chemical conversion.

11. The method of claim 1, said method further comprising the step of recovering (Z)-11-hexadecen-1-ol.

12. The method of claim 11, said method further comprising the step of formulating the recovered (Z)-11-hexadecen-1-ol into a pheromone composition.

13. The method of claim 1, further comprising the step of converting at least part of the (Z)-11-hexadecen-1-ol into (Z)11-hexadecen-1-yl acetate by a step of chemical conversion.

14. The method of claim 13, said method further comprising the step of recovering (Z)11-hexadecen-1-yl acetate.

\* \* \* \* \*

SEQUENCE LISTING

```
<160> NUMBER OF SEQ ID NOS: 53

<210> SEQ ID NO 1
<211> LENGTH: 981
<212> TYPE: DNA
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(981)
<223> OTHER INFORMATION: delta-11-desaturase

<400> SEQUENCE: 1 atg gtt cca aac aag ggt tcc tct gat gtt ttg tct gaa cat tct gaa      48
Met Val Pro Asn Lys Gly Ser Ser Asp Val Leu Ser Glu His Ser Glu
1               5                   10                  15 cca caa ttc acc aag ttg att gct cca caa gct ggt cca aga aag tac      96
Pro Gln Phe Thr Lys Leu Ile Ala Pro Gln Ala Gly Pro Arg Lys Tyr
            20                  25                  30 aaa atc gtt tac aga aac ttg ttg acc ttc ggt tac tgg cat ttg tct     144
Lys Ile Val Tyr Arg Asn Leu Leu Thr Phe Gly Tyr Trp His Leu Ser
        35                  40                  45 gct gtt tat ggt ttg tac ttg tgt ttc act tgt gct aag tgg gct act     192
Ala Val Tyr Gly Leu Tyr Leu Cys Phe Thr Cys Ala Lys Trp Ala Thr
    50                  55                  60 att ttg ttc gct ttc ttc ttg tac gtt atc gcc gaa att ggt att act     240
Ile Leu Phe Ala Phe Phe Leu Tyr Val Ile Ala Glu Ile Gly Ile Thr
65                  70                  75                  80 ggt ggt gct cat aga tta tgg gct cat aga act tac aaa gcc aag ttg     288
Gly Gly Ala His Arg Leu Trp Ala His Arg Thr Tyr Lys Ala Lys Leu
                85                  90                  95 cca ttg gaa atc ttg ttg ttg atc atg aac tcc att gcc ttc caa gat     336
Pro Leu Glu Ile Leu Leu Leu Ile Met Asn Ser Ile Ala Phe Gln Asp
            100                 105                 110 act gct ttt act tgg gct aga gat cat aga ttg cat cac aag tac tct     384
Thr Ala Phe Thr Trp Ala Arg Asp His Arg Leu His His Lys Tyr Ser
        115                 120                 125 gat act gat gct gat cca cat aat gct act aga ggt ttc ttc tac tct     432
Asp Thr Asp Ala Asp Pro His Asn Ala Thr Arg Gly Phe Phe Tyr Ser
    130                 135                 140
```

```
cat gtt ggt tgg ttg ttg gtt aag aaa cac cca gaa gtt aag gct aga    480
His Val Gly Trp Leu Leu Val Lys Lys His Pro Glu Val Lys Ala Arg
145                 150                 155                 160 ggt aag tac ttg tct ttg gat gac ttg aag aac aac cct ttg ttg aag    528
Gly Lys Tyr Leu Ser Leu Asp Asp Leu Lys Asn Asn Pro Leu Leu Lys
                165                 170                 175 ttc caa aag aag tac gcc att ttg gtc att ggt act ttg tgc ttt ttg    576
Phe Gln Lys Lys Tyr Ala Ile Leu Val Ile Gly Thr Leu Cys Phe Leu
            180                 185                 190 atg cca act ttc gtt cca gtt tac ttt tgg ggt gaa ggt att tct act    624
Met Pro Thr Phe Val Pro Val Tyr Phe Trp Gly Glu Gly Ile Ser Thr
        195                 200                 205 gcc tgg aac att aac ttg tta aga tac gtc atg aac ttg aac atg acc    672
Ala Trp Asn Ile Asn Leu Leu Arg Tyr Val Met Asn Leu Asn Met Thr
    210                 215                 220 ttt ttg gtt aac tcc gct gct cat att ttt ggt aac aag cca tac gat    720
Phe Leu Val Asn Ser Ala Ala His Ile Phe Gly Asn Lys Pro Tyr Asp
225                 230                 235                 240 aag tct atc gcc tct gtt caa aac atc tct gtt tct ttg gct act ttc    768
Lys Ser Ile Ala Ser Val Gln Asn Ile Ser Val Ser Leu Ala Thr Phe
                245                 250                 255 ggt gaa ggt ttc cat aac tac cat cat act tat cca tgg gat tac aga    816
Gly Glu Gly Phe His Asn Tyr His His Thr Tyr Pro Trp Asp Tyr Arg
            260                 265                 270 gct gct gaa ttg ggt aac aat aga ttg aat atg acc acc gcc ttc att    864
Ala Ala Glu Leu Gly Asn Asn Arg Leu Asn Met Thr Thr Ala Phe Ile
        275                 280                 285 gat ttc ttt gct tgg att ggt tgg gcc tac gat ttg aaa tct gtt cca    912
Asp Phe Phe Ala Trp Ile Gly Trp Ala Tyr Asp Leu Lys Ser Val Pro
    290                 295                 300 caa gaa gct att gct aag aga tgt gct aaa act ggt gat ggt act gat    960
Gln Glu Ala Ile Ala Lys Arg Cys Ala Lys Thr Gly Asp Gly Thr Asp
305                 310                 315                 320 atg tgg ggt aga aag aga tga                                        981
Met Trp Gly Arg Lys Arg
                325

<210> SEQ ID NO 2
<211> LENGTH: 326
<212> TYPE: PRT
<213> ORGANISM: Artificial sequence
<220> FEATURE:
<223> OTHER INFORMATION: Synthetic Construct

<400> SEQUENCE: 2

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
        35                  40                  45

Ala Val Tyr Gly Leu Tyr Leu Cys Phe Thr Cys Ala Lys Trp Ala Thr
    50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Leu Ile Met Asn Ser Ile Ala Phe Gln Asp
            100                 105                 110
```

```
Thr Ala Phe Thr Trp Ala Arg Asp His Arg Leu His His Lys Tyr Ser
            115                 120                 125

Asp Thr Asp Ala Asp Pro His Asn Ala Thr Arg Gly Phe Phe Tyr Ser
130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
            180                 185                 190

Met Pro Thr Phe Val Pro Val Tyr Phe Trp Gly Glu Gly Ile Ser Thr
        195                 200                 205

Ala Trp Asn Ile Asn Leu Leu Arg Tyr Val Met Asn Leu Asn Met Thr
    210                 215                 220

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
                245                 250                 255

Gly Glu Gly Phe His Asn Tyr His His Thr Tyr Pro Trp Asp Tyr Arg
            260                 265                 270

Ala Ala Glu Leu Gly Asn Asn Arg Leu Asn Met Thr Thr Ala Phe Ile
        275                 280                 285

Asp Phe Phe Ala Trp Ile Gly Trp Ala Tyr Asp Leu Lys Ser Val Pro
    290                 295                 300

Gln Glu Ala Ile Ala Lys Arg Cys Ala Lys Thr Gly Asp Gly Thr Asp
305                 310                 315                 320

Met Trp Gly Arg Lys Arg
                325

<210> SEQ ID NO 3
<211> LENGTH: 1377
<212> TYPE: DNA
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(1377)
<223> OTHER INFORMATION: Ase_FAR

<400> SEQUENCE: 3 atg cca gtc ttg act tct aga gaa gac gaa aaa ttg tcc gtc cca gaa      48
Met Pro Val Leu Thr Ser Arg Glu Asp Glu Lys Leu Ser Val Pro Glu
1               5                   10                  15 ttt tac gct ggt aag tct att ttt gtt acc ggt ggt act ggt ttc ttg      96
Phe Tyr Ala Gly Lys Ser Ile Phe Val Thr Gly Gly Thr Gly Phe Leu
            20                  25                  30 ggt aag gtt ttt atc gaa aag ttg ttg tac tgc tgc cca gat atc gat     144
Gly Lys Val Phe Ile Glu Lys Leu Leu Tyr Cys Cys Pro Asp Ile Asp
        35                  40                  45 aag atc tac atg ttg atc aga gaa aaa aag aac ttg tcc atc gac gaa     192
Lys Ile Tyr Met Leu Ile Arg Glu Lys Lys Asn Leu Ser Ile Asp Glu
    50                  55                  60 aga atg tcc aag ttt ttg gat gac cct ttg ttc tcc aga ttg aaa gaa     240
Arg Met Ser Lys Phe Leu Asp Asp Pro Leu Phe Ser Arg Leu Lys Glu
65                  70                  75                  80 gaa aga cca ggt gac ttg gaa aag atc gtt ttg att cca ggt gat att     288
Glu Arg Pro Gly Asp Leu Glu Lys Ile Val Leu Ile Pro Gly Asp Ile
                85                  90                  95
```

-continued

| | | |
|---|---|---|
| acc gct cct aat ttg ggt ttg tct gct gaa aac gaa aga atc ttg ttg<br>Thr Ala Pro Asn Leu Gly Leu Ser Ala Glu Asn Glu Arg Ile Leu Leu<br>          100                         105                         110 | 336 |

```
acc gct cct aat ttg ggt ttg tct gct gaa aac gaa aga atc ttg ttg      336
Thr Ala Pro Asn Leu Gly Leu Ser Ala Glu Asn Glu Arg Ile Leu Leu
            100                 105                 110 gaa aag gtc agt gtc att att aac tct gct gct acc gtt aag ttc aac      384
Glu Lys Val Ser Val Ile Ile Asn Ser Ala Ala Thr Val Lys Phe Asn
        115                 120                 125 gaa cca ttg cca att gct tgg aag att aac gtt gaa ggt act aga atg      432
Glu Pro Leu Pro Ile Ala Trp Lys Ile Asn Val Glu Gly Thr Arg Met
    130                 135                 140 ttg ttg gcc ttg tct aga aga atg aag aga atc gaa gtt ttc atc cat      480
Leu Leu Ala Leu Ser Arg Arg Met Lys Arg Ile Glu Val Phe Ile His
145                 150                 155                 160 atc tcc acc gct tac tct aat gct tct tct gat aga att gtc gtt gac      528
Ile Ser Thr Ala Tyr Ser Asn Ala Ser Ser Asp Arg Ile Val Val Asp
                165                 170                 175 gaa atc ttg tat cca gct cca gct gat atg gat caa gtt tat caa ttg      576
Glu Ile Leu Tyr Pro Ala Pro Ala Asp Met Asp Gln Val Tyr Gln Leu
            180                 185                 190 gtt aag gac ggt gtc act gaa gaa gaa acc gaa aga tta ttg aac ggt      624
Val Lys Asp Gly Val Thr Glu Glu Glu Thr Glu Arg Leu Leu Asn Gly
        195                 200                 205 ttg cca aac act tac act ttc act aag gct ttg acc gaa cat ttg gtt      672
Leu Pro Asn Thr Tyr Thr Phe Thr Lys Ala Leu Thr Glu His Leu Val
    210                 215                 220 gct gaa cat caa act tac gtt cca acc att atc atc aga cca tct gtt      720
Ala Glu His Gln Thr Tyr Val Pro Thr Ile Ile Ile Arg Pro Ser Val
225                 230                 235                 240 gtt gcc tcc att aag gat gaa cct att aga ggt tgg ttg tgt aat tgg      768
Val Ala Ser Ile Lys Asp Glu Pro Ile Arg Gly Trp Leu Cys Asn Trp
                245                 250                 255 ttt ggt gct act ggt att tct gtt ttc act gct aag ggt ttg aac aga      816
Phe Gly Ala Thr Gly Ile Ser Val Phe Thr Ala Lys Gly Leu Asn Arg
            260                 265                 270 gtt ttg ttg ggt aaa gcc tct aac atc gtt gat gtt atc cca gtt gat      864
Val Leu Leu Gly Lys Ala Ser Asn Ile Val Asp Val Ile Pro Val Asp
        275                 280                 285 tac gtt gcc aac ttg gtt ata gtt gct ggt gct aaa tct ggt ggt caa      912
Tyr Val Ala Asn Leu Val Ile Val Ala Gly Ala Lys Ser Gly Gly Gln
    290                 295                 300 aag tct gat gaa ttg aaa atc tac aac tgc tgc tcc tct gac tgt aat      960
Lys Ser Asp Glu Leu Lys Ile Tyr Asn Cys Cys Ser Ser Asp Cys Asn
305                 310                 315                 320 cca gtt act ttg aag aag atc atc aaa gaa ttc acc gaa gat acc atc     1008
Pro Val Thr Leu Lys Lys Ile Ile Lys Glu Phe Thr Glu Asp Thr Ile
                325                 330                 335 aag aac aag tcc cat att atg cca ttg cca ggt tgg ttc gtt ttt act     1056
Lys Asn Lys Ser His Ile Met Pro Leu Pro Gly Trp Phe Val Phe Thr
            340                 345                 350 aag tac aaa tgg ttg ttg act ttg ttg acc atc atc ttc caa atg ttg     1104
Lys Tyr Lys Trp Leu Leu Thr Leu Leu Thr Ile Ile Phe Gln Met Leu
        355                 360                 365 cca atg tat ttg gcc gat gtt tac aga gtc ttg acc ggt aaa att cca     1152
Pro Met Tyr Leu Ala Asp Val Tyr Arg Val Leu Thr Gly Lys Ile Pro
    370                 375                 380 aga tat atg aag ttg cac cac ttg gtc att caa acc aga ttg ggt att     1200
Arg Tyr Met Lys Leu His His Leu Val Ile Gln Thr Arg Leu Gly Ile
385                 390                 395                 400 gat ttc ttc acc tct cat tct tgg gtt atg aag acc gat aga gtc aga     1248
Asp Phe Phe Thr Ser His Ser Trp Val Met Lys Thr Asp Arg Val Arg
```

```
                            405                 410                 415
gaa tta ttc ggt tct ttg tcc ttg gcc gaa aaa cac atg ttt cca tgt        1296
Glu Leu Phe Gly Ser Leu Ser Leu Ala Glu Lys His Met Phe Pro Cys
            420                 425                 430 gat cca tct tcc att gat tgg acc gat tac ttg caa tct tac tgc tat        1344
Asp Pro Ser Ser Ile Asp Trp Thr Asp Tyr Leu Gln Ser Tyr Cys Tyr
            435                 440                 445 ggt gtc aga aga ttc tta gaa aag aag aag taa                            1377
Gly Val Arg Arg Phe Leu Glu Lys Lys Lys
        450                 455

<210> SEQ ID NO 4
<211> LENGTH: 458
<212> TYPE: PRT
<213> ORGANISM: Artificial sequence
<220> FEATURE:
<223> OTHER INFORMATION: Synthetic Construct

<400> SEQUENCE: 4

Met Pro Val Leu Thr Ser Arg Glu Asp Glu Lys Leu Ser Val Pro Glu
1               5                   10                  15

Phe Tyr Ala Gly Lys Ser Ile Phe Val Thr Gly Gly Thr Gly Phe Leu
            20                  25                  30

Gly Lys Val Phe Ile Glu Lys Leu Leu Tyr Cys Cys Pro Asp Ile Asp
        35                  40                  45

Lys Ile Tyr Met Leu Ile Arg Glu Lys Lys Asn Leu Ser Ile Asp Glu
    50                  55                  60

Arg Met Ser Lys Phe Leu Asp Asp Pro Leu Phe Ser Arg Leu Lys Glu
65                  70                  75                  80

Glu Arg Pro Gly Asp Leu Glu Lys Ile Val Leu Ile Pro Gly Asp Ile
                85                  90                  95

Thr Ala Pro Asn Leu Gly Leu Ser Ala Glu Asn Glu Arg Ile Leu Leu
            100                 105                 110

Glu Lys Val Ser Val Ile Ile Asn Ser Ala Ala Thr Val Lys Phe Asn
        115                 120                 125

Glu Pro Leu Pro Ile Ala Trp Lys Ile Asn Val Glu Gly Thr Arg Met
    130                 135                 140

Leu Leu Ala Leu Ser Arg Arg Met Lys Arg Ile Glu Val Phe Ile His
145                 150                 155                 160

Ile Ser Thr Ala Tyr Ser Asn Ala Ser Ser Asp Arg Ile Val Val Asp
                165                 170                 175

Glu Ile Leu Tyr Pro Ala Pro Ala Asp Met Asp Gln Val Tyr Gln Leu
            180                 185                 190

Val Lys Asp Gly Val Thr Glu Glu Thr Glu Arg Leu Leu Asn Gly
        195                 200                 205

Leu Pro Asn Thr Tyr Thr Phe Thr Lys Ala Leu Thr Glu His Leu Val
    210                 215                 220

Ala Glu His Gln Thr Tyr Val Pro Thr Ile Ile Arg Pro Ser Val
225                 230                 235                 240

Val Ala Ser Ile Lys Asp Glu Pro Ile Arg Gly Trp Leu Cys Asn Trp
                245                 250                 255

Phe Gly Ala Thr Gly Ile Ser Val Phe Thr Ala Lys Gly Leu Asn Arg
            260                 265                 270

Val Leu Leu Gly Lys Ala Ser Asn Ile Val Asp Val Ile Pro Val Asp
        275                 280                 285

Tyr Val Ala Asn Leu Val Ile Val Ala Gly Ala Lys Ser Gly Gly Gln
```

```
                290                 295                 300
Lys Ser Asp Glu Leu Lys Ile Tyr Asn Cys Cys Ser Asp Cys Asn
305                 310                 315                 320

Pro Val Thr Leu Lys Lys Ile Ile Lys Glu Phe Thr Glu Asp Thr Ile
                325                 330                 335

Lys Asn Lys Ser His Ile Met Pro Leu Pro Gly Trp Phe Val Phe Thr
                340                 345                 350

Lys Tyr Lys Trp Leu Leu Thr Leu Leu Thr Ile Ile Phe Gln Met Leu
            355                 360                 365

Pro Met Tyr Leu Ala Asp Val Tyr Arg Val Leu Thr Gly Lys Ile Pro
    370                 375                 380

Arg Tyr Met Lys Leu His His Leu Val Ile Gln Thr Arg Leu Gly Ile
385                 390                 395                 400

Asp Phe Phe Thr Ser His Ser Trp Val Met Lys Thr Asp Arg Val Arg
                405                 410                 415

Glu Leu Phe Gly Ser Leu Ser Leu Ala Glu Lys His Met Phe Pro Cys
            420                 425                 430

Asp Pro Ser Ser Ile Asp Trp Thr Asp Tyr Leu Gln Ser Tyr Cys Tyr
        435                 440                 445

Gly Val Arg Arg Phe Leu Glu Lys Lys Lys
    450                 455

<210> SEQ ID NO 5
<211> LENGTH: 1365
<212> TYPE: DNA
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(1365)
<223> OTHER INFORMATION: Har_FAR_KKYR
<220> FEATURE:
<221> NAME/KEY: sig_peptide
<222> LOCATION: (1354)..(1365)
<223> OTHER INFORMATION: KKYR signal peptide

<400> SEQUENCE: 5 atg gtt gtc ttg acc tcc aaa gaa act aag cca tct gtt gct gaa ttt    48
Met Val Val Leu Thr Ser Lys Glu Thr Lys Pro Ser Val Ala Glu Phe
1               5                   10                  15 tac gct ggt aag tct gtt ttc att act ggt ggt act ggt ttc ttg ggt    96
Tyr Ala Gly Lys Ser Val Phe Ile Thr Gly Gly Thr Gly Phe Leu Gly
            20                  25                  30 aag gtt ttc att gaa aag ttg ttg tac tcc tgc cca gat atc ggt aat    144
Lys Val Phe Ile Glu Lys Leu Leu Tyr Ser Cys Pro Asp Ile Gly Asn
        35                  40                  45 atc tac atg ttg atc aga gaa aag aag ggt ttg tcc gtt tcc gaa aga    192
Ile Tyr Met Leu Ile Arg Glu Lys Lys Gly Leu Ser Val Ser Glu Arg
    50                  55                  60 atc aag cac ttt ttg gat gat cct ttg ttc acc aga ttg aaa gaa aaa    240
Ile Lys His Phe Leu Asp Asp Pro Leu Phe Thr Arg Leu Lys Glu Lys
65                  70                  75                  80 aga cca gcc gac ttg gaa aag atc gtt ttg att cca ggt gat att act    288
Arg Pro Ala Asp Leu Glu Lys Ile Val Leu Ile Pro Gly Asp Ile Thr
                85                  90                  95 gct cca gat ttg ggt att acc tcc gaa aac gaa aag atg ttg atc gaa    336
Ala Pro Asp Leu Gly Ile Thr Ser Glu Asn Glu Lys Met Leu Ile Glu
            100                 105                 110 aag gtc agt gtc att att cat tct gct gct acc gtt aag ttc aac gaa    384
```

```
Lys Val Ser Val Ile Ile His Ser Ala Ala Thr Val Lys Phe Asn Glu
            115                 120                 125 cca ttg cca act gct tgg aag att aac gtt gaa ggt act aga atg atg       432
Pro Leu Pro Thr Ala Trp Lys Ile Asn Val Glu Gly Thr Arg Met Met
130                 135                 140 ttg gcc ttg tct aga aga atg aag aga atc gaa gtt ttc atc cat atc       480
Leu Ala Leu Ser Arg Arg Met Lys Arg Ile Glu Val Phe Ile His Ile
145                 150                 155                 160 tct acc gct tac act aac acc aac aga gaa gtt gtt gac gaa atc ttg       528
Ser Thr Ala Tyr Thr Asn Thr Asn Arg Glu Val Val Asp Glu Ile Leu
                165                 170                 175 tat cca gct cca gct gat att gat caa gtt cac aga tat gtt aag gac       576
Tyr Pro Ala Pro Ala Asp Ile Asp Gln Val His Arg Tyr Val Lys Asp
            180                 185                 190 ggt atc tct gaa gaa gaa act gaa aaa atc ttg aac ggt aga cca aac       624
Gly Ile Ser Glu Glu Glu Thr Glu Lys Ile Leu Asn Gly Arg Pro Asn
        195                 200                 205 act tac act ttc act aag gct ttg acc gaa cat ttg gtt gct gaa aat       672
Thr Tyr Thr Phe Thr Lys Ala Leu Thr Glu His Leu Val Ala Glu Asn
210                 215                 220 caa gct tac gtt cca acc att atc gtt aga cca tca gtt gtt gct gcc       720
Gln Ala Tyr Val Pro Thr Ile Ile Val Arg Pro Ser Val Val Ala Ala
225                 230                 235                 240 att aag gat gaa cct att aag ggt tgg ttg ggt aat tgg tat ggt gct       768
Ile Lys Asp Glu Pro Ile Lys Gly Trp Leu Gly Asn Trp Tyr Gly Ala
                245                 250                 255 aca ggt ttg act gtt ttt act gct aag ggt ttg aac aga gtt atc tac       816
Thr Gly Leu Thr Val Phe Thr Ala Lys Gly Leu Asn Arg Val Ile Tyr
            260                 265                 270 ggt cac tct tct aac atc gtt gat ttg atc cca gtt gat tac gtt gcc       864
Gly His Ser Ser Asn Ile Val Asp Leu Ile Pro Val Asp Tyr Val Ala
        275                 280                 285 aac ttg gtt att gct gct ggt gct aaa tct tct aag tct act gaa ttg       912
Asn Leu Val Ile Ala Ala Gly Ala Lys Ser Ser Lys Ser Thr Glu Leu
290                 295                 300 aag gtc tac aac tgc tgt tct tct gct tgt aac cca att act atc ggt       960
Lys Val Tyr Asn Cys Cys Ser Ser Ala Cys Asn Pro Ile Thr Ile Gly
305                 310                 315                 320 aag ttg atg tcc atg ttt gct gaa gat gct atc aag caa aag tct tac      1008
Lys Leu Met Ser Met Phe Ala Glu Asp Ala Ile Lys Gln Lys Ser Tyr
                325                 330                 335 gct atg cca ttg cca ggt tgg tac att ttt act aag tac aag tgg ttg      1056
Ala Met Pro Leu Pro Gly Trp Tyr Ile Phe Thr Lys Tyr Lys Trp Leu
            340                 345                 350 gtc ttg ttg ttg acc att ttg ttc caa gtt att cca gcc tac att acc      1104
Val Leu Leu Leu Thr Ile Leu Phe Gln Val Ile Pro Ala Tyr Ile Thr
        355                 360                 365 gac ttg tac aga cat ttg att ggt aag aac cca aga tat atc aag ttg      1152
Asp Leu Tyr Arg His Leu Ile Gly Lys Asn Pro Arg Tyr Ile Lys Leu
370                 375                 380 caa tcc ttg gtc aat caa acc aga tcc tcc att gat ttc ttc acc tct      1200
Gln Ser Leu Val Asn Gln Thr Arg Ser Ser Ile Asp Phe Phe Thr Ser
385                 390                 395                 400 cat tct tgg gtt atg aag gct gat aga gtc aga gaa tta ttc gct tct      1248
His Ser Trp Val Met Lys Ala Asp Arg Val Arg Glu Leu Phe Ala Ser
                405                 410                 415 ttg tct cca gca gat aag tac ttg ttt cca tgt gat cca acc gat att      1296
Leu Ser Pro Ala Asp Lys Tyr Leu Phe Pro Cys Asp Pro Thr Asp Ile
            420                 425                 430
```

```
aac tgg acc cat tac att caa gat tac tgc tgg ggt gtt aga cat ttc   1344
Asn Trp Thr His Tyr Ile Gln Asp Tyr Cys Trp Gly Val Arg His Phe
        435                 440                 445 ttg gaa aaa aag tac aga taa                                       1365
Leu Glu Lys Lys Tyr Arg
    450
```

<210> SEQ ID NO 6
<211> LENGTH: 454
<212> TYPE: PRT
<213> ORGANISM: Artificial sequence
<220> FEATURE:
<223> OTHER INFORMATION: Synthetic Construct

<400> SEQUENCE: 6

```
Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Arg Tyr Val Lys Asp
            180                 185                 190

Gly Ile Ser Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
        275                 280                 285

Asn Leu Val Ile Ala Ala Gly Ala Lys Ser Ser Lys Ser Thr Glu Leu
            290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
```

```
                    325                 330                 335
Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
            355                 360                 365

Asp Leu Tyr Arg His Leu Ile Gly Lys Asn Pro Arg Tyr Ile Lys Leu
        370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
        435                 440                 445

Leu Glu Lys Lys Tyr Arg
    450
```

<210> SEQ ID NO 7
<211> LENGTH: 1368
<212> TYPE: DNA
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(1368)
<223> OTHER INFORMATION: Har_FAR

<400> SEQUENCE: 7

```
atg gtt gtc ttg acc tcc aaa gaa act aag cca tct gtt gct gaa ttt    48
Met Val Val Leu Thr Ser Lys Glu Thr Lys Pro Ser Val Ala Glu Phe
1               5                   10                  15 tac gct ggt aag tct gtt ttc att act ggt ggt act ggt ttc ttg ggt    96
Tyr Ala Gly Lys Ser Val Phe Ile Thr Gly Gly Thr Gly Phe Leu Gly
            20                  25                  30 aag gtt ttc att gaa aag ttg ttg tac tcc tgc cca gat atc ggt aat   144
Lys Val Phe Ile Glu Lys Leu Leu Tyr Ser Cys Pro Asp Ile Gly Asn
        35                  40                  45 atc tac atg ttg atc aga gaa aag aag ggt ttg tcc gtt tcc gaa aga   192
Ile Tyr Met Leu Ile Arg Glu Lys Lys Gly Leu Ser Val Ser Glu Arg
    50                  55                  60 atc aag cac ttt ttg gat gat cct ttg ttc acc aga ttg aaa gaa aaa   240
Ile Lys His Phe Leu Asp Asp Pro Leu Phe Thr Arg Leu Lys Glu Lys
65                  70                  75                  80 aga cca gcc gac ttg gaa aag atc gtt ttg att cca ggt gat att act   288
Arg Pro Ala Asp Leu Glu Lys Ile Val Leu Ile Pro Gly Asp Ile Thr
                85                  90                  95 gct cca gat ttg ggt att acc tcc gaa aac gaa aag atg ttg atc gaa   336
Ala Pro Asp Leu Gly Ile Thr Ser Glu Asn Glu Lys Met Leu Ile Glu
            100                 105                 110 aag gtc agt gtc att att cat tct gct gct acc gtt aag ttc aac gaa   384
Lys Val Ser Val Ile Ile His Ser Ala Ala Thr Val Lys Phe Asn Glu
        115                 120                 125 cca ttg cca act gct tgg aag att aac gtt gaa ggt act aga atg atg   432
Pro Leu Pro Thr Ala Trp Lys Ile Asn Val Glu Gly Thr Arg Met Met
    130                 135                 140 ttg gcc ttg tct aga aga atg aag aga atc gaa gtt ttc atc cat atc   480
Leu Ala Leu Ser Arg Arg Met Lys Arg Ile Glu Val Phe Ile His Ile
145                 150                 155                 160
```

```
tct acc gct tac act aac acc aac aga gaa gtt gtt gac gaa atc ttg      528
Ser Thr Ala Tyr Thr Asn Thr Asn Arg Glu Val Val Asp Glu Ile Leu
                165                 170                 175 tat cca gct cca gct gat att gat caa gtt cac aga tat gtt aag gac      576
Tyr Pro Ala Pro Ala Asp Ile Asp Gln Val His Arg Tyr Val Lys Asp
            180                 185                 190 ggt atc tct gaa gaa gaa act gaa aaa atc ttg aac ggt aga cca aac      624
Gly Ile Ser Glu Glu Glu Thr Glu Lys Ile Leu Asn Gly Arg Pro Asn
        195                 200                 205 act tac act ttc act aag gct ttg acc gaa cat ttg gtt gct gaa aat      672
Thr Tyr Thr Phe Thr Lys Ala Leu Thr Glu His Leu Val Ala Glu Asn
    210                 215                 220 caa gct tac gtt cca acc att atc gtt aga cca tca gtt gtt gct gcc      720
Gln Ala Tyr Val Pro Thr Ile Ile Val Arg Pro Ser Val Val Ala Ala
225                 230                 235                 240 att aag gat gaa cct att aag ggt tgg ttg ggt aat tgg tat ggt gct      768
Ile Lys Asp Glu Pro Ile Lys Gly Trp Leu Gly Asn Trp Tyr Gly Ala
                245                 250                 255 aca ggt ttg act gtt ttt act gct aag ggt ttg aac aga gtt atc tac      816
Thr Gly Leu Thr Val Phe Thr Ala Lys Gly Leu Asn Arg Val Ile Tyr
            260                 265                 270 ggt cac tct tct aac atc gtt gat ttg atc cca gtt gat tac gtt gcc      864
Gly His Ser Ser Asn Ile Val Asp Leu Ile Pro Val Asp Tyr Val Ala
        275                 280                 285 aac ttg gtt att gct gct ggt gct aaa tct tct aag tct act gaa ttg      912
Asn Leu Val Ile Ala Ala Gly Ala Lys Ser Ser Lys Ser Thr Glu Leu
    290                 295                 300 aag gtc tac aac tgc tgt tct tct gct tgt aac cca att act atc ggt      960
Lys Val Tyr Asn Cys Cys Ser Ser Ala Cys Asn Pro Ile Thr Ile Gly
305                 310                 315                 320 aag ttg atg tcc atg ttt gct gaa gat gct atc aag caa aag tct tac     1008
Lys Leu Met Ser Met Phe Ala Glu Asp Ala Ile Lys Gln Lys Ser Tyr
                325                 330                 335 gct atg cca ttg cca ggt tgg tac att ttt act aag tac aag tgg ttg     1056
Ala Met Pro Leu Pro Gly Trp Tyr Ile Phe Thr Lys Tyr Lys Trp Leu
            340                 345                 350 gtc ttg ttg ttg acc att ttg ttc caa gtt att cca gcc tac att acc     1104
Val Leu Leu Leu Thr Ile Leu Phe Gln Val Ile Pro Ala Tyr Ile Thr
        355                 360                 365 gac ttg tac aga cat ttg att ggt aag aac cca aga tat atc aag ttg     1152
Asp Leu Tyr Arg His Leu Ile Gly Lys Asn Pro Arg Tyr Ile Lys Leu
    370                 375                 380 caa tcc ttg gtc aat caa acc aga tcc tcc att gat ttc ttc acc tct     1200
Gln Ser Leu Val Asn Gln Thr Arg Ser Ser Ile Asp Phe Phe Thr Ser
385                 390                 395                 400 cat tct tgg gtt atg aag gct gat aga gtc aga gaa tta ttc gct tct     1248
His Ser Trp Val Met Lys Ala Asp Arg Val Arg Glu Leu Phe Ala Ser
                405                 410                 415 ttg tct cca gca gat aag tac ttg ttt cca tgt gat cca acc gat att     1296
Leu Ser Pro Ala Asp Lys Tyr Leu Phe Pro Cys Asp Pro Thr Asp Ile
            420                 425                 430 aac tgg acc cat tac att caa gat tac tgc tgg ggt gtt aga cat ttc     1344
Asn Trp Thr His Tyr Ile Gln Asp Tyr Cys Trp Gly Val Arg His Phe
        435                 440                 445 ttg gaa aaa aaa agc tac gaa taa                                     1368
Leu Glu Lys Lys Ser Tyr Glu
    450                 455

<210> SEQ ID NO 8
```

<211> LENGTH: 455
<212> TYPE: PRT
<213> ORGANISM: Artificial sequence
<220> FEATURE:
<223> OTHER INFORMATION: Synthetic Construct

<400> SEQUENCE: 8

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Arg Tyr Val Lys Asp
            180                 185                 190

Gly Ile Ser Glu Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
        275                 280                 285

Asn Leu Val Ile Ala Ala Gly Ala Lys Ser Ser Lys Ser Thr Glu Leu
290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
370                 375                 380

```
Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
        435                 440                 445

Leu Glu Lys Lys Ser Tyr Glu
    450                 455

<210> SEQ ID NO 9
<211> LENGTH: 1365
<212> TYPE: DNA
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(1365)
<223> OTHER INFORMATION: Har_FAR_HDEL

<400> SEQUENCE: 9 atg gtt gtc ttg acc tcc aaa gaa act aag cca tct gtt gct gaa ttt      48
Met Val Val Leu Thr Ser Lys Glu Thr Lys Pro Ser Val Ala Glu Phe
1               5                   10                  15 tac gct ggt aag tct gtt ttc att act ggt ggt act ggt ttc ttg ggt      96
Tyr Ala Gly Lys Ser Val Phe Ile Thr Gly Gly Thr Gly Phe Leu Gly
                20                  25                  30 aag gtt ttc att gaa aag ttg ttg tac tcc tgc cca gat atc ggt aat     144
Lys Val Phe Ile Glu Lys Leu Leu Tyr Ser Cys Pro Asp Ile Gly Asn
            35                  40                  45 atc tac atg ttg atc aga gaa aag aag ggt ttg tcc gtt tcc gaa aga     192
Ile Tyr Met Leu Ile Arg Glu Lys Lys Gly Leu Ser Val Ser Glu Arg
        50                  55                  60 atc aag cac ttt ttg gat gat cct ttg ttc acc aga ttg aaa gaa aaa     240
Ile Lys His Phe Leu Asp Asp Pro Leu Phe Thr Arg Leu Lys Glu Lys
65                  70                  75                  80 aga cca gcc gac ttg gaa aag atc gtt ttg att cca ggt gat att act     288
Arg Pro Ala Asp Leu Glu Lys Ile Val Leu Ile Pro Gly Asp Ile Thr
                85                  90                  95 gct cca gat ttg ggt att acc tcc gaa aac gaa aag atg ttg atc gaa     336
Ala Pro Asp Leu Gly Ile Thr Ser Glu Asn Glu Lys Met Leu Ile Glu
            100                 105                 110 aag gtc agt gtc att att cat tct gct gct acc gtt aag ttc aac gaa     384
Lys Val Ser Val Ile Ile His Ser Ala Ala Thr Val Lys Phe Asn Glu
        115                 120                 125 cca ttg cca act gct tgg aag att aac gtt gaa ggt act aga atg atg     432
Pro Leu Pro Thr Ala Trp Lys Ile Asn Val Glu Gly Thr Arg Met Met
    130                 135                 140 ttg gcc ttg tct aga aga atg aag aga atc gaa gtt ttc atc cat atc     480
Leu Ala Leu Ser Arg Arg Met Lys Arg Ile Glu Val Phe Ile His Ile
145                 150                 155                 160 tct acc gct tac act aac acc aac aga gaa gtt gtt gac gaa atc ttg     528
Ser Thr Ala Tyr Thr Asn Thr Asn Arg Glu Val Val Asp Glu Ile Leu
                165                 170                 175 tat cca gct cca gct gat att gat caa gtt cac aga tat gtt aag gac     576
Tyr Pro Ala Pro Ala Asp Ile Asp Gln Val His Arg Tyr Val Lys Asp
            180                 185                 190 ggt atc tct gaa gaa gaa act gaa aaa atc ttg aac ggt aga cca aac     624
```

```
                Gly Ile Ser Glu Glu Thr Glu Lys Ile Leu Asn Gly Arg Pro Asn
                            195                 200                 205 act tac act ttc act aag gct ttg acc gaa cat ttg gtt gct gaa aat       672
Thr Tyr Thr Phe Thr Lys Ala Leu Thr Glu His Leu Val Ala Glu Asn
    210                 215                 220 caa gct tac gtt cca acc att atc gtt aga cca tca gtt gtt gct gcc       720
Gln Ala Tyr Val Pro Thr Ile Ile Val Arg Pro Ser Val Val Ala Ala
225                 230                 235                 240 att aag gat gaa cct att aag ggt tgg ttg ggt aat tgg tat ggt gct       768
Ile Lys Asp Glu Pro Ile Lys Gly Trp Leu Gly Asn Trp Tyr Gly Ala
                245                 250                 255 aca ggt ttg act gtt ttt act gct aag ggt ttg aac aga gtt atc tac       816
Thr Gly Leu Thr Val Phe Thr Ala Lys Gly Leu Asn Arg Val Ile Tyr
            260                 265                 270 ggt cac tct tct aac atc gtt gat ttg atc cca gtt gat tac gtt gcc       864
Gly His Ser Ser Asn Ile Val Asp Leu Ile Pro Val Asp Tyr Val Ala
        275                 280                 285 aac ttg gtt att gct gct ggt gct aaa tct tct aag tct act gaa ttg       912
Asn Leu Val Ile Ala Ala Gly Ala Lys Ser Ser Lys Ser Thr Glu Leu
    290                 295                 300 aag gtc tac aac tgc tgt tct tct gct tgt aac cca att act atc ggt       960
Lys Val Tyr Asn Cys Cys Ser Ser Ala Cys Asn Pro Ile Thr Ile Gly
305                 310                 315                 320 aag ttg atg tcc atg ttt gct gaa gat gct atc aag caa aag tct tac      1008
Lys Leu Met Ser Met Phe Ala Glu Asp Ala Ile Lys Gln Lys Ser Tyr
                325                 330                 335 gct atg cca ttg cca ggt tgg tac att ttt act aag tac aag tgg ttg      1056
Ala Met Pro Leu Pro Gly Trp Tyr Ile Phe Thr Lys Tyr Lys Trp Leu
            340                 345                 350 gtc ttg ttg ttg acc att ttg ttc caa gtt att cca gcc tac att acc      1104
Val Leu Leu Leu Thr Ile Leu Phe Gln Val Ile Pro Ala Tyr Ile Thr
        355                 360                 365 gac ttg tac aga cat ttg att ggt aag aac cca aga tat atc aag ttg      1152
Asp Leu Tyr Arg His Leu Ile Gly Lys Asn Pro Arg Tyr Ile Lys Leu
    370                 375                 380 caa tcc ttg gtc aat caa acc aga tcc tcc att gat ttc ttc acc tct      1200
Gln Ser Leu Val Asn Gln Thr Arg Ser Ser Ile Asp Phe Phe Thr Ser
385                 390                 395                 400 cat tct tgg gtt atg aag gct gat aga gtc aga gaa tta ttc gct tct      1248
His Ser Trp Val Met Lys Ala Asp Arg Val Arg Glu Leu Phe Ala Ser
                405                 410                 415 ttg tct cca gca gat aag tac ttg ttt cca tgt gat cca acc gat att      1296
Leu Ser Pro Ala Asp Lys Tyr Leu Phe Pro Cys Asp Pro Thr Asp Ile
            420                 425                 430 aac tgg acc cat tac att caa gat tac tgc tgg ggt gtt aga cat ttc      1344
Asn Trp Thr His Tyr Ile Gln Asp Tyr Cys Trp Gly Val Arg His Phe
        435                 440                 445 ttg gaa cat gat gaa ttg taa                                          1365
Leu Glu His Asp Glu Leu
        450

<210> SEQ ID NO 10
<211> LENGTH: 454
<212> TYPE: PRT
<213> ORGANISM: Artificial sequence
<220> FEATURE:
<223> OTHER INFORMATION: Synthetic Construct

<400> SEQUENCE: 10

Met Val Val Leu Thr Ser Lys Glu Thr Lys Pro Ser Val Ala Glu Phe
1               5                   10                  15
```

```
Tyr Ala Gly Lys Ser Val Phe Ile Thr Gly Gly Thr Gly Phe Leu Gly
             20                  25                  30

Lys Val Phe Ile Glu Lys Leu Leu Tyr Ser Cys Pro Asp Ile Gly Asn
         35                  40                  45

Ile Tyr Met Leu Ile Arg Glu Lys Lys Gly Leu Ser Val Ser Glu Arg
 50                  55                  60

Ile Lys His Phe Leu Asp Asp Pro Leu Phe Thr Arg Leu Lys Glu Lys
 65                  70                  75                  80

Arg Pro Ala Asp Leu Glu Lys Ile Val Leu Ile Pro Gly Asp Ile Thr
                 85                  90                  95

Ala Pro Asp Leu Gly Ile Thr Ser Glu Asn Lys Met Leu Ile Glu
                100                 105                 110

Lys Val Ser Val Ile Ile His Ser Ala Ala Thr Val Lys Phe Asn Glu
         115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Arg Tyr Val Lys Asp
                180                 185                 190

Gly Ile Ser Glu Glu Glu Thr Glu Lys Ile Leu Asn Gly Arg Pro Asn
            195                 200                 205

Thr Tyr Thr Phe Thr Lys Ala Leu Thr Glu His Leu Val Ala Glu Asn
210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430
```

```
Asn Trp Thr His Tyr Ile Gln Asp Tyr Cys Trp Gly Val Arg His Phe
        435                 440                 445

Leu Glu His Asp Glu Leu
    450

<210> SEQ ID NO 11
<211> LENGTH: 1371
<212> TYPE: DNA
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(1371)
<223> OTHER INFORMATION: Has_FAR

<400> SEQUENCE: 11 atg gtt gtc ttg acc tcc aaa gaa act aag cca tct gtt gct gaa ttt      48
Met Val Val Leu Thr Ser Lys Glu Thr Lys Pro Ser Val Ala Glu Phe
1               5                  10                  15 tac gct ggt aag tct gtt ttc att act ggt ggt act ggt ttc ttg ggt      96
Tyr Ala Gly Lys Ser Val Phe Ile Thr Gly Gly Thr Gly Phe Leu Gly
            20                  25                  30 aag atc ttc att gaa aag ttg ttg tac tcc tgc cca gat atc ggt aat     144
Lys Ile Phe Ile Glu Lys Leu Leu Tyr Ser Cys Pro Asp Ile Gly Asn
        35                  40                  45 atc tac atg ttg atc aga gaa aag aag ggt ttg tcc gtt tcc gaa aga     192
Ile Tyr Met Leu Ile Arg Glu Lys Lys Gly Leu Ser Val Ser Glu Arg
    50                  55                  60 atc aag caa ttt ttg gat gac cct ttg ttc acc aga ttg aaa gaa aaa     240
Ile Lys Gln Phe Leu Asp Asp Pro Leu Phe Thr Arg Leu Lys Glu Lys
65                  70                  75                  80 aga cca gcc gac ttg gaa aag atc gtt ttg att cca ggt gat att act     288
Arg Pro Ala Asp Leu Glu Lys Ile Val Leu Ile Pro Gly Asp Ile Thr
                85                  90                  95 gct cca gat ttg ggt att acc tcc gaa aac gaa aag atg ttg atc gaa     336
Ala Pro Asp Leu Gly Ile Thr Ser Glu Asn Glu Lys Met Leu Ile Glu
            100                 105                 110 aag gtc agt gtc att att cat tct gct gct acc gtt aag ttc aac gaa     384
Lys Val Ser Val Ile Ile His Ser Ala Ala Thr Val Lys Phe Asn Glu
        115                 120                 125 cca ttg cca act gct tgg aag att aac gtt gaa ggt act aga atg atg     432
Pro Leu Pro Thr Ala Trp Lys Ile Asn Val Glu Gly Thr Arg Met Met
    130                 135                 140 ttg gcc ttg tct aga aga atg aag aga atc gaa gtt ttc atc cat atc     480
Leu Ala Leu Ser Arg Arg Met Lys Arg Ile Glu Val Phe Ile His Ile
145                 150                 155                 160 tct acc gct tac act aac acc aac aga gaa gtt gtt gac gaa atc ttg     528
Ser Thr Ala Tyr Thr Asn Thr Asn Arg Glu Val Val Asp Glu Ile Leu
                165                 170                 175 tat cca gct cca gct gat att gat caa gtt cac caa tat gtt aag gac     576
Tyr Pro Ala Pro Ala Asp Ile Asp Gln Val His Gln Tyr Val Lys Asp
            180                 185                 190 ggt atc tct gaa gaa gaa act gaa aaa atc ttg aac ggt aga cca aac     624
Gly Ile Ser Glu Glu Glu Thr Glu Lys Ile Leu Asn Gly Arg Pro Asn
        195                 200                 205 act tac act ttc act aag gct ttg acc gaa cat ttg gtt gct gaa aat     672
Thr Tyr Thr Phe Thr Lys Ala Leu Thr Glu His Leu Val Ala Glu Asn
    210                 215                 220 caa gct tac gtt cca acc att atc gtt aga cca tca gtt gtt gct gcc     720
Gln Ala Tyr Val Pro Thr Ile Ile Val Arg Pro Ser Val Val Ala Ala
225                 230                 235                 240
```

```
att aag gat gaa cct att aag ggt tgg ttg ggt aat tgg tat ggt gct      768
Ile Lys Asp Glu Pro Ile Lys Gly Trp Leu Gly Asn Trp Tyr Gly Ala
            245                 250                 255 aca ggt ttg act gtt ttt act gct aag ggt ttg aac aga gtt atc tac      816
Thr Gly Leu Thr Val Phe Thr Ala Lys Gly Leu Asn Arg Val Ile Tyr
        260                 265                 270 ggt cat tcc tct tac atc gtt gat ttg atc cca gtt gat tac gtt gcc      864
Gly His Ser Ser Tyr Ile Val Asp Leu Ile Pro Val Asp Tyr Val Ala
    275                 280                 285 aac ttg gtt att gct gct ggt gct aaa tct tct aag tct act gaa ttg      912
Asn Leu Val Ile Ala Ala Gly Ala Lys Ser Ser Lys Ser Thr Glu Leu
290                 295                 300 aag gtc tac aac tgc tgt tct tct gct tgt aac cca att act atc ggt      960
Lys Val Tyr Asn Cys Cys Ser Ser Ala Cys Asn Pro Ile Thr Ile Gly
305                 310                 315                 320 aag ttg atg tcc atg ttt gct gaa gat gct atc aag caa aag tct tac     1008
Lys Leu Met Ser Met Phe Ala Glu Asp Ala Ile Lys Gln Lys Ser Tyr
            325                 330                 335 gct atg cca ttg cca ggt tgg tat gtt ttt aca aag tac aag tgg ttg     1056
Ala Met Pro Leu Pro Gly Trp Tyr Val Phe Thr Lys Tyr Lys Trp Leu
        340                 345                 350 gtc ttg ttg ttg acc att ttg ttc caa gtt att cca gcc tac att acc     1104
Val Leu Leu Leu Thr Ile Leu Phe Gln Val Ile Pro Ala Tyr Ile Thr
    355                 360                 365 gac ttg tac aga cat ttg att ggt aag aac cca aga tat atc aag ttg     1152
Asp Leu Tyr Arg His Leu Ile Gly Lys Asn Pro Arg Tyr Ile Lys Leu
370                 375                 380 caa tcc ttg gtc aat caa acc aga tcc tcc att gat ttc ttc acc tct     1200
Gln Ser Leu Val Asn Gln Thr Arg Ser Ser Ile Asp Phe Phe Thr Ser
385                 390                 395                 400 cat tct tgg gtt atg aag gct gat aga gtc aga gaa tta ttc gct tct     1248
His Ser Trp Val Met Lys Ala Asp Arg Val Arg Glu Leu Phe Ala Ser
            405                 410                 415 ttg tct cca gca gat aag tac ttg ttt cca tgt gat cca acc gat att     1296
Leu Ser Pro Ala Asp Lys Tyr Leu Phe Pro Cys Asp Pro Thr Asp Ile
        420                 425                 430 aac tgg acc cat tac att caa gat tac tgc tgg ggt gtt aga cac ttc     1344
Asn Trp Thr His Tyr Ile Gln Asp Tyr Cys Trp Gly Val Arg His Phe
    435                 440                 445 ttg gaa aaa aag act acc aac aag taa                                 1371
Leu Glu Lys Lys Thr Thr Asn Lys
        450                 455

<210> SEQ ID NO 12
<211> LENGTH: 456
<212> TYPE: PRT
<213> ORGANISM: Artificial sequence
<220> FEATURE:
<223> OTHER INFORMATION: Synthetic Construct

<400> SEQUENCE: 12

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Ile Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60
```

Ile Lys Gln Phe Leu Asp Asp Pro Leu Phe Thr Arg Leu Lys Glu Lys
 65                  70                  75                  80

Arg Pro Ala Asp Leu Glu Lys Ile Val Leu Ile Pro Gly Asp Ile Thr
             85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
                180                 185                 190

Gly Ile Ser Glu Glu Glu Thr Glu Lys Ile Leu Asn Gly Arg Pro Asn
            195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Val Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
        435                 440                 445

Leu Glu Lys Lys Thr Thr Asn Lys
    450                 455

<210> SEQ ID NO 13
<211> LENGTH: 1365
<212> TYPE: DNA

```
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(1365)
<223> OTHER INFORMATION: Has_FAR_HDEL
<220> FEATURE:
<221> NAME/KEY: sig_peptide
<222> LOCATION: (1354)..(1365)
<223> OTHER INFORMATION: HDEL

<400> SEQUENCE: 13
```

| | | | | | | | | | | | | | | | | |
|---|---|---|---|---|---|---|---|---|---|---|---|---|---|---|---|---|
| atg | gtt | gtc | ttg | acc | tcc | aaa | gaa | act | aag | cca | tct | gtt | gct | gaa | ttt | 48 |
| Met | Val | Val | Leu | Thr | Ser | Lys | Glu | Thr | Lys | Pro | Ser | Val | Ala | Glu | Phe | |
| 1 | | | | 5 | | | | | 10 | | | | | 15 | | |

| tac | gct | ggt | aag | tct | gtt | ttc | att | act | ggt | ggt | act | ggt | ttc | ttg | ggt | 96 |
|---|---|---|---|---|---|---|---|---|---|---|---|---|---|---|---|---|
| Tyr | Ala | Gly | Lys | Ser | Val | Phe | Ile | Thr | Gly | Gly | Thr | Gly | Phe | Leu | Gly | |
| | | | 20 | | | | | 25 | | | | | 30 | | | |

| aag | atc | ttc | att | gaa | aag | ttg | ttg | tac | tcc | tgc | cca | gat | atc | ggt | aat | 144 |
|---|---|---|---|---|---|---|---|---|---|---|---|---|---|---|---|---|
| Lys | Ile | Phe | Ile | Glu | Lys | Leu | Leu | Tyr | Ser | Cys | Pro | Asp | Ile | Gly | Asn | |
| | 35 | | | | | 40 | | | | | 45 | | | | | |

| atc | tac | atg | ttg | atc | aga | gaa | aag | aag | ggt | ttg | tcc | gtt | tcc | gaa | aga | 192 |
|---|---|---|---|---|---|---|---|---|---|---|---|---|---|---|---|---|
| Ile | Tyr | Met | Leu | Ile | Arg | Glu | Lys | Lys | Gly | Leu | Ser | Val | Ser | Glu | Arg | |
| 50 | | | | | 55 | | | | | 60 | | | | | | |

| atc | aag | caa | ttt | ttg | gat | gac | cct | ttg | ttc | acc | aga | ttg | aaa | gaa | aaa | 240 |
|---|---|---|---|---|---|---|---|---|---|---|---|---|---|---|---|---|
| Ile | Lys | Gln | Phe | Leu | Asp | Asp | Pro | Leu | Phe | Thr | Arg | Leu | Lys | Glu | Lys | |
| 65 | | | | 70 | | | | | 75 | | | | | 80 | | |

| aga | cca | gcc | gac | ttg | gaa | aag | atc | gtt | ttg | att | cca | ggt | gat | att | act | 288 |
|---|---|---|---|---|---|---|---|---|---|---|---|---|---|---|---|---|
| Arg | Pro | Ala | Asp | Leu | Glu | Lys | Ile | Val | Leu | Ile | Pro | Gly | Asp | Ile | Thr | |
| | | | | 85 | | | | | 90 | | | | | 95 | | |

| gct | cca | gat | ttg | ggt | att | acc | tcc | gaa | aac | gaa | aag | atg | ttg | atc | gaa | 336 |
|---|---|---|---|---|---|---|---|---|---|---|---|---|---|---|---|---|
| Ala | Pro | Asp | Leu | Gly | Ile | Thr | Ser | Glu | Asn | Glu | Lys | Met | Leu | Ile | Glu | |
| | | | 100 | | | | | 105 | | | | | 110 | | | |

| aag | gtc | agt | gtc | att | att | cat | tct | gct | gct | acc | gtt | aag | ttc | aac | gaa | 384 |
|---|---|---|---|---|---|---|---|---|---|---|---|---|---|---|---|---|
| Lys | Val | Ser | Val | Ile | Ile | His | Ser | Ala | Ala | Thr | Val | Lys | Phe | Asn | Glu | |
| | | 115 | | | | | 120 | | | | | 125 | | | | |

| cca | ttg | cca | act | gct | tgg | aag | att | aac | gtt | gaa | ggt | act | aga | atg | atg | 432 |
|---|---|---|---|---|---|---|---|---|---|---|---|---|---|---|---|---|
| Pro | Leu | Pro | Thr | Ala | Trp | Lys | Ile | Asn | Val | Glu | Gly | Thr | Arg | Met | Met | |
| | 130 | | | | | 135 | | | | | 140 | | | | | |

| ttg | gcc | ttg | tct | aga | aga | atg | aag | aga | atc | gaa | gtt | ttc | atc | cat | atc | 480 |
|---|---|---|---|---|---|---|---|---|---|---|---|---|---|---|---|---|
| Leu | Ala | Leu | Ser | Arg | Arg | Met | Lys | Arg | Ile | Glu | Val | Phe | Ile | His | Ile | |
| 145 | | | | | 150 | | | | | 155 | | | | | 160 | |

| tct | acc | gct | tac | act | aac | acc | aac | aga | gaa | gtt | gtt | gac | gaa | atc | ttg | 528 |
|---|---|---|---|---|---|---|---|---|---|---|---|---|---|---|---|---|
| Ser | Thr | Ala | Tyr | Thr | Asn | Thr | Asn | Arg | Glu | Val | Val | Asp | Glu | Ile | Leu | |
| | | | | 165 | | | | | 170 | | | | | 175 | | |

| tat | cca | gct | cca | gct | gat | att | gat | caa | gtt | cac | caa | tat | gtt | aag | gac | 576 |
|---|---|---|---|---|---|---|---|---|---|---|---|---|---|---|---|---|
| Tyr | Pro | Ala | Pro | Ala | Asp | Ile | Asp | Gln | Val | His | Gln | Tyr | Val | Lys | Asp | |
| | | | 180 | | | | | 185 | | | | | 190 | | | |

| ggt | atc | tct | gaa | gaa | gaa | act | gaa | aaa | atc | ttg | aac | ggt | aga | cca | aac | 624 |
|---|---|---|---|---|---|---|---|---|---|---|---|---|---|---|---|---|
| Gly | Ile | Ser | Glu | Glu | Glu | Thr | Glu | Lys | Ile | Leu | Asn | Gly | Arg | Pro | Asn | |
| | | 195 | | | | | 200 | | | | | 205 | | | | |

| act | tac | act | ttc | act | aag | gct | ttg | acc | gaa | cat | ttg | gtt | gct | gaa | aat | 672 |
|---|---|---|---|---|---|---|---|---|---|---|---|---|---|---|---|---|
| Thr | Tyr | Thr | Phe | Thr | Lys | Ala | Leu | Thr | Glu | His | Leu | Val | Ala | Glu | Asn | |
| | 210 | | | | | 215 | | | | | 220 | | | | | |

| caa | gct | tac | gtt | cca | acc | att | atc | gtt | aga | cca | tca | gtt | gtt | gct | gcc | 720 |
|---|---|---|---|---|---|---|---|---|---|---|---|---|---|---|---|---|
| Gln | Ala | Tyr | Val | Pro | Thr | Ile | Ile | Val | Arg | Pro | Ser | Val | Val | Ala | Ala | |
| 225 | | | | | 230 | | | | | 235 | | | | | 240 | |

| att | aag | gat | gaa | cct | att | aag | ggt | tgg | ttg | ggt | aat | tgg | tat | ggt | gct | 768 |
|---|---|---|---|---|---|---|---|---|---|---|---|---|---|---|---|---|
| Ile | Lys | Asp | Glu | Pro | Ile | Lys | Gly | Trp | Leu | Gly | Asn | Trp | Tyr | Gly | Ala | |
| | | | | 245 | | | | | 250 | | | | | 255 | | |

| aca | ggt | ttg | act | gtt | ttt | act | gct | aag | ggt | ttg | aac | aga | gtt | atc | tac | 816 |

```
Thr Gly Leu Thr Val Phe Thr Ala Lys Gly Leu Asn Arg Val Ile Tyr
            260                 265                 270 ggt cat tcc tct tac atc gtt gat ttg atc cca gtt gat tac gtt gcc      864
Gly His Ser Ser Tyr Ile Val Asp Leu Ile Pro Val Asp Tyr Val Ala
            275                 280                 285 aac ttg gtt att gct gct ggt gct aaa tct tct aag tct act gaa ttg      912
Asn Leu Val Ile Ala Ala Gly Ala Lys Ser Ser Lys Ser Thr Glu Leu
            290                 295                 300 aag gtc tac aac tgc tgt tct tct gct tgt aac cca att act atc ggt      960
Lys Val Tyr Asn Cys Cys Ser Ser Ala Cys Asn Pro Ile Thr Ile Gly
305                 310                 315                 320 aag ttg atg tcc atg ttt gct gaa gat gct atc aag caa aag tct tac     1008
Lys Leu Met Ser Met Phe Ala Glu Asp Ala Ile Lys Gln Lys Ser Tyr
                325                 330                 335 gct atg cca ttg cca ggt tgg tat gtt ttt aca aag tac aag tgg ttg     1056
Ala Met Pro Leu Pro Gly Trp Tyr Val Phe Thr Lys Tyr Lys Trp Leu
            340                 345                 350 gtc ttg ttg ttg acc att ttg ttc caa gtt att cca gcc tac att acc     1104
Val Leu Leu Leu Thr Ile Leu Phe Gln Val Ile Pro Ala Tyr Ile Thr
        355                 360                 365 gac ttg tac aga cat ttg att ggt aag aac cca aga tat atc aag ttg     1152
Asp Leu Tyr Arg His Leu Ile Gly Lys Asn Pro Arg Tyr Ile Lys Leu
    370                 375                 380 caa tcc ttg gtc aat caa acc aga tcc tcc att gat ttc ttc acc tct     1200
Gln Ser Leu Val Asn Gln Thr Arg Ser Ser Ile Asp Phe Phe Thr Ser
385                 390                 395                 400 cat tct tgg gtt atg aag gct gat aga gtc aga gaa tta ttc gct tct     1248
His Ser Trp Val Met Lys Ala Asp Arg Val Arg Glu Leu Phe Ala Ser
                405                 410                 415 ttg tct cca gca gat aag tac ttg ttt cca tgt gat cca acc gat att     1296
Leu Ser Pro Ala Asp Lys Tyr Leu Phe Pro Cys Asp Pro Thr Asp Ile
            420                 425                 430 aac tgg acc cat tac att caa gat tac tgc tgg ggt gtt aga cac ttc     1344
Asn Trp Thr His Tyr Ile Gln Asp Tyr Cys Trp Gly Val Arg His Phe
        435                 440                 445 ttg gaa cat gat gaa ttg taa                                          1365
Leu Glu His Asp Glu Leu
    450

<210> SEQ ID NO 14
<211> LENGTH: 454
<212> TYPE: PRT
<213> ORGANISM: Artificial sequence
<220> FEATURE:
<223> OTHER INFORMATION: Synthetic Construct

<400> SEQUENCE: 14

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Ile Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60

Ile Lys Gln Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95
```

Ala Pro Asp Leu Gly Ile Thr Ser Glu Asn Glu Lys Met Leu Ile Glu
            100                 105                 110

Lys Val Ser Val Ile Ile His Ser Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Val Arg Pro Ser Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Tyr Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Val Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
        435                 440                 445

Leu Glu His Asp Glu Leu
    450

<210> SEQ ID NO 15
<211> LENGTH: 1362
<212> TYPE: DNA
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(1362)

<223> OTHER INFORMATION: Hs_FAR

<400> SEQUENCE: 15

| | | | | | | | | | | | | | | | | |
|---|---|---|---|---|---|---|---|---|---|---|---|---|---|---|---|---|
| atg | gtt | gtc | ttg | acc | tcc | aaa | gaa | act | aag | cca | tct | gtt | gct | gaa | ttt | 48 |
| Met | Val | Val | Leu | Thr | Ser | Lys | Glu | Thr | Lys | Pro | Ser | Val | Ala | Glu | Phe | |
| 1 | | | | 5 | | | | | 10 | | | | | 15 | | |
| tac | gct | ggt | aag | tct | gtt | ttc | att | act | ggt | ggt | act | ggt | ttc | ttg | ggt | 96 |
| Tyr | Ala | Gly | Lys | Ser | Val | Phe | Ile | Thr | Gly | Gly | Thr | Gly | Phe | Leu | Gly | |
| | | | 20 | | | | | 25 | | | | | 30 | | | |
| aag | gtt | ttc | att | gaa | aag | ttg | ttg | tac | tcc | tgc | cca | gat | atc | ggt | aat | 144 |
| Lys | Val | Phe | Ile | Glu | Lys | Leu | Leu | Tyr | Ser | Cys | Pro | Asp | Ile | Gly | Asn | |
| | | 35 | | | | | 40 | | | | | 45 | | | | |
| atc | tac | atg | ttg | atc | aga | gaa | aag | aag | ggt | ttg | tcc | gtt | tcc | gaa | aga | 192 |
| Ile | Tyr | Met | Leu | Ile | Arg | Glu | Lys | Lys | Gly | Leu | Ser | Val | Ser | Glu | Arg | |
| | 50 | | | | | 55 | | | | | 60 | | | | | |
| atc | aag | cac | ttt | ttg | gat | gat | cct | ttg | ttc | acc | aga | ttg | aaa | gaa | aaa | 240 |
| Ile | Lys | His | Phe | Leu | Asp | Asp | Pro | Leu | Phe | Thr | Arg | Leu | Lys | Glu | Lys | |
| 65 | | | | | 70 | | | | | 75 | | | | | 80 | |
| aga | cca | gcc | gac | ttg | gaa | aag | atc | gtt | ttg | att | cca | ggt | gat | att | act | 288 |
| Arg | Pro | Ala | Asp | Leu | Glu | Lys | Ile | Val | Leu | Ile | Pro | Gly | Asp | Ile | Thr | |
| | | | | 85 | | | | | 90 | | | | | 95 | | |
| gct | cca | gat | ttg | ggt | att | acc | tcc | gaa | aac | gaa | aag | atg | ttg | atc | gaa | 336 |
| Ala | Pro | Asp | Leu | Gly | Ile | Thr | Ser | Glu | Asn | Glu | Lys | Met | Leu | Ile | Glu | |
| | | | 100 | | | | | 105 | | | | | 110 | | | |
| aag | gtc | agt | gtc | att | att | cat | tct | gct | gct | acc | gtt | aag | ttc | aac | gaa | 384 |
| Lys | Val | Ser | Val | Ile | Ile | His | Ser | Ala | Ala | Thr | Val | Lys | Phe | Asn | Glu | |
| | | 115 | | | | | 120 | | | | | 125 | | | | |
| cca | ttg | cca | act | gct | tgg | aag | att | aac | gtt | gaa | ggt | act | aga | atg | atg | 432 |
| Pro | Leu | Pro | Thr | Ala | Trp | Lys | Ile | Asn | Val | Glu | Gly | Thr | Arg | Met | Met | |
| | 130 | | | | | 135 | | | | | 140 | | | | | |
| ttg | gcc | ttg | tct | aga | aga | atg | aag | aga | atc | gaa | gtt | ttc | atc | cat | atc | 480 |
| Leu | Ala | Leu | Ser | Arg | Arg | Met | Lys | Arg | Ile | Glu | Val | Phe | Ile | His | Ile | |
| 145 | | | | | 150 | | | | | 155 | | | | | 160 | |
| tct | acc | gct | tac | act | aac | acc | aac | aga | gaa | gtt | gtt | gac | gaa | atc | ttg | 528 |
| Ser | Thr | Ala | Tyr | Thr | Asn | Thr | Asn | Arg | Glu | Val | Val | Asp | Glu | Ile | Leu | |
| | | | | 165 | | | | | 170 | | | | | 175 | | |
| tat | cca | gct | cca | gct | gat | att | gat | caa | gtt | cac | caa | tat | gtt | aag | gac | 576 |
| Tyr | Pro | Ala | Pro | Ala | Asp | Ile | Asp | Gln | Val | His | Gln | Tyr | Val | Lys | Asp | |
| | | | 180 | | | | | 185 | | | | | 190 | | | |
| ggt | atc | tct | gaa | gaa | gaa | act | gaa | aaa | atc | ttg | aac | ggt | aga | cca | aac | 624 |
| Gly | Ile | Ser | Glu | Glu | Glu | Thr | Glu | Lys | Ile | Leu | Asn | Gly | Arg | Pro | Asn | |
| | | 195 | | | | | 200 | | | | | 205 | | | | |
| act | tac | act | ttc | act | aag | gct | ttg | acc | gaa | cat | ttg | gtt | gct | gaa | aat | 672 |
| Thr | Tyr | Thr | Phe | Thr | Lys | Ala | Leu | Thr | Glu | His | Leu | Val | Ala | Glu | Asn | |
| | 210 | | | | | 215 | | | | | 220 | | | | | |
| caa | gct | tac | gtt | cca | acc | att | atc | gtt | aga | cca | tca | gtt | gtt | gct | gcc | 720 |
| Gln | Ala | Tyr | Val | Pro | Thr | Ile | Ile | Val | Arg | Pro | Ser | Val | Val | Ala | Ala | |
| 225 | | | | | 230 | | | | | 235 | | | | | 240 | |
| att | aag | gat | gaa | cct | att | aag | ggt | tgg | ttg | ggt | aat | tgg | tat | ggt | gct | 768 |
| Ile | Lys | Asp | Glu | Pro | Ile | Lys | Gly | Trp | Leu | Gly | Asn | Trp | Tyr | Gly | Ala | |
| | | | | 245 | | | | | 250 | | | | | 255 | | |
| aca | ggt | ttg | act | gtt | ttt | act | gct | aag | ggt | ttg | aac | aga | gtt | atc | tac | 816 |
| Thr | Gly | Leu | Thr | Val | Phe | Thr | Ala | Lys | Gly | Leu | Asn | Arg | Val | Ile | Tyr | |
| | | | 260 | | | | | 265 | | | | | 270 | | | |
| ggt | cac | tct | tct | aac | atc | gtt | gat | ttg | atc | cca | gtt | gat | tac | gtt | gcc | 864 |
| Gly | His | Ser | Ser | Asn | Ile | Val | Asp | Leu | Ile | Pro | Val | Asp | Tyr | Val | Ala | |
| | | 275 | | | | | 280 | | | | | 285 | | | | |
| aac | ttg | gtt | att | gct | gct | ggt | gct | aaa | tct | tct | aag | tct | act | gaa | ttg | 912 |
| Asn | Leu | Val | Ile | Ala | Ala | Gly | Ala | Lys | Ser | Ser | Lys | Ser | Thr | Glu | Leu | |
| | 290 | | | | | 295 | | | | | 300 | | | | | |

```
aag gtc tac aac tgc tgt tct tct gct tgt aac cca att act atc ggt      960
Lys Val Tyr Asn Cys Cys Ser Ser Ala Cys Asn Pro Ile Thr Ile Gly
305                 310                 315                 320 aag ttg atg tcc atg ttt gct gaa gat gct atc aag caa aag tct tac     1008
Lys Leu Met Ser Met Phe Ala Glu Asp Ala Ile Lys Gln Lys Ser Tyr
                325                 330                 335 gct atg cca ttg cca ggt tgg tac att ttt act aag tac aag tgg ttg     1056
Ala Met Pro Leu Pro Gly Trp Tyr Ile Phe Thr Lys Tyr Lys Trp Leu
            340                 345                 350 gtc ttg ttg ttg acc att ttg ttc caa gtt att cca gcc tac att acc     1104
Val Leu Leu Leu Thr Ile Leu Phe Gln Val Ile Pro Ala Tyr Ile Thr
        355                 360                 365 gac ttg tac aga cat ttg att ggt aag aac cca aga tat atc aag ttg     1152
Asp Leu Tyr Arg His Leu Ile Gly Lys Asn Pro Arg Tyr Ile Lys Leu
    370                 375                 380 caa tcc ttg gtc aat caa acc aga tcc tcc att gat ttc ttc acc aac     1200
Gln Ser Leu Val Asn Gln Thr Arg Ser Ser Ile Asp Phe Phe Thr Asn
385                 390                 395                 400 cat tct tgg gtt atg aag gct gat aga gtc aga gaa tta ttc gct tct     1248
His Ser Trp Val Met Lys Ala Asp Arg Val Arg Glu Leu Phe Ala Ser
                405                 410                 415 ttg tct cca gca gat aag tac ttg ttt cca tgt gat cca gtc aac atc     1296
Leu Ser Pro Ala Asp Lys Tyr Leu Phe Pro Cys Asp Pro Val Asn Ile
            420                 425                 430 aat tgg aga caa tat atc caa gat tac tgc tgg ggt gtt aga cat ttc     1344
Asn Trp Arg Gln Tyr Ile Gln Asp Tyr Cys Trp Gly Val Arg His Phe
        435                 440                 445 ttg gaa aaa aag act taa                                              1362
Leu Glu Lys Lys Thr
    450

<210> SEQ ID NO 16
<211> LENGTH: 453
<212> TYPE: PRT
<213> ORGANISM: Artificial sequence
<220> FEATURE:
<223> OTHER INFORMATION: Synthetic Construct

<400> SEQUENCE: 16

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
```

```
                145                 150                 155                 160
        Ser Thr Ala Tyr Thr Asn Thr Asn Arg Glu Val Val Asp Glu Ile Leu
                        165                 170                 175
        Tyr Pro Ala Pro Ala Asp Ile Asp Gln Val His Gln Tyr Val Lys Asp
                        180                 185                 190
        Gly Ile Ser Glu Glu Thr Glu Lys Ile Leu Asn Gly Arg Pro Asn
                        195                 200                 205
        Thr Tyr Thr Phe Thr Lys Ala Leu Thr Glu His Leu Val Ala Glu Asn
                210                 215                 220
        Gln Ala Tyr Val Pro Thr Ile Ile Val Arg Pro Ser Val Val Ala Ala
        225                 230                 235                 240
        Ile Lys Asp Glu Pro Ile Lys Gly Trp Leu Gly Asn Trp Tyr Gly Ala
                        245                 250                 255
        Thr Gly Leu Thr Val Phe Thr Ala Lys Gly Leu Asn Arg Val Ile Tyr
                        260                 265                 270
        Gly His Ser Ser Asn Ile Val Asp Leu Ile Pro Val Asp Tyr Val Ala
                        275                 280                 285
        Asn Leu Val Ile Ala Ala Gly Ala Lys Ser Ser Lys Ser Thr Glu Leu
                290                 295                 300
        Lys Val Tyr Asn Cys Cys Ser Ser Ala Cys Asn Pro Ile Thr Ile Gly
        305                 310                 315                 320
        Lys Leu Met Ser Met Phe Ala Glu Asp Ala Ile Lys Gln Lys Ser Tyr
                        325                 330                 335
        Ala Met Pro Leu Pro Gly Trp Tyr Ile Phe Thr Lys Tyr Lys Trp Leu
                        340                 345                 350
        Val Leu Leu Leu Thr Ile Leu Phe Gln Val Ile Pro Ala Tyr Ile Thr
                        355                 360                 365
        Asp Leu Tyr Arg His Leu Ile Gly Lys Asn Pro Arg Tyr Ile Lys Leu
                        370                 375                 380
        Gln Ser Leu Val Asn Gln Thr Arg Ser Ser Ile Asp Phe Phe Thr Asn
        385                 390                 395                 400
        His Ser Trp Val Met Lys Ala Asp Arg Val Arg Glu Leu Phe Ala Ser
                        405                 410                 415
        Leu Ser Pro Ala Asp Lys Tyr Leu Phe Pro Cys Asp Pro Val Asn Ile
                        420                 425                 430
        Asn Trp Arg Gln Tyr Ile Gln Asp Tyr Cys Trp Gly Val Arg His Phe
                        435                 440                 445
        Leu Glu Lys Lys Thr
                450

<210> SEQ ID NO 17
<211> LENGTH: 1362
<212> TYPE: DNA
<213> ORGANISM: Artificial sequence
<220> FEATURE:
<223> OTHER INFORMATION: Codon-optimised for Saccharomyces cerevisiae
<220> FEATURE:
<221> NAME/KEY: CDS
<222> LOCATION: (1)..(1362)
<223> OTHER INFORMATION: Hs_FAR_HDEL
<220> FEATURE:
<221> NAME/KEY: sig_peptide
<222> LOCATION: (1351)..(1362)
<223> OTHER INFORMATION: HDEL

<400> SEQUENCE: 17 atg gtt gtc ttg acc tcc aaa gaa act aag cca tct gtt gct gaa ttt       48
Met Val Val Leu Thr Ser Lys Glu Thr Lys Pro Ser Val Ala Glu Phe
```

```
1               5                    10                   15
tac gct ggt aag tct gtt ttc att act ggt ggt act ggt ttc ttg ggt      96
Tyr Ala Gly Lys Ser Val Phe Ile Thr Gly Gly Thr Gly Phe Leu Gly
             20                   25                   30 aag gtt ttc att gaa aag ttg ttg tac tcc tgc cca gat atc ggt aat     144
Lys Val Phe Ile Glu Lys Leu Leu Tyr Ser Cys Pro Asp Ile Gly Asn
         35                   40                   45 atc tac atg ttg atc aga gaa aag aag ggt ttg tcc gtt tcc gaa aga     192
Ile Tyr Met Leu Ile Arg Glu Lys Lys Gly Leu Ser Val Ser Glu Arg
     50                   55                   60 atc aag cac ttt ttg gat gat cct ttg ttc acc aga ttg aaa gaa aaa     240
Ile Lys His Phe Leu Asp Asp Pro Leu Phe Thr Arg Leu Lys Glu Lys
 65                   70                   75                   80 aga cca gcc gac ttg gaa aag atc gtt ttg att cca ggt gat att act     288
Arg Pro Ala Asp Leu Glu Lys Ile Val Leu Ile Pro Gly Asp Ile Thr
                 85                   90                   95 gct cca gat ttg ggt att acc tcc gaa aac gaa aag atg ttg atc gaa     336
Ala Pro Asp Leu Gly Ile Thr Ser Glu Asn Glu Lys Met Leu Ile Glu
             100                  105                  110 aag gtc agt gtc att att cat tct gct gct acc gtt aag ttc aac gaa     384
Lys Val Ser Val Ile Ile His Ser Ala Ala Thr Val Lys Phe Asn Glu
         115                  120                  125 cca ttg cca act gct tgg aag att aac gtt gaa ggt act aga atg atg     432
Pro Leu Pro Thr Ala Trp Lys Ile Asn Val Glu Gly Thr Arg Met Met
     130                  135                  140 ttg gcc ttg tct aga aga atg aag aga atc gaa gtt ttc atc cat atc     480
Leu Ala Leu Ser Arg Arg Met Lys Arg Ile Glu Val Phe Ile His Ile
145                  150                  155                  160 tct acc gct tac act aac acc aac aga gaa gtt gtt gac gaa atc ttg     528
Ser Thr Ala Tyr Thr Asn Thr Asn Arg Glu Val Val Asp Glu Ile Leu
                 165                  170                  175 tat cca gct cca gct gat att gat caa gtt cac caa tat gtt aag gac     576
Tyr Pro Ala Pro Ala Asp Ile Asp Gln Val His Gln Tyr Val Lys Asp
             180                  185                  190 ggt atc tct gaa gaa gaa act gaa aaa atc ttg aac ggt aga cca aac     624
Gly Ile Ser Glu Glu Glu Thr Glu Lys Ile Leu Asn Gly Arg Pro Asn
         195                  200                  205 act tac act ttc act aag gct ttg acc gaa cat ttg gtt gct gaa aat     672
Thr Tyr Thr Phe Thr Lys Ala Leu Thr Glu His Leu Val Ala Glu Asn
     210                  215                  220 caa gct tac gtt cca acc att atc gtt aga cca tca gtt gtt gct gcc     720
Gln Ala Tyr Val Pro Thr Ile Ile Val Arg Pro Ser Val Val Ala Ala
225                  230                  235                  240 att aag gat gaa cct att aag ggt tgg ttg ggt aat tgg tat ggt gct     768
Ile Lys Asp Glu Pro Ile Lys Gly Trp Leu Gly Asn Trp Tyr Gly Ala
                 245                  250                  255 aca ggt ttg act gtt ttt act gct aag ggt ttg aac aga gtt atc tac     816
Thr Gly Leu Thr Val Phe Thr Ala Lys Gly Leu Asn Arg Val Ile Tyr
             260                  265                  270 ggt cac tct tct aac atc gtt gat ttg atc cca gtt gat tac gtt gcc     864
Gly His Ser Ser Asn Ile Val Asp Leu Ile Pro Val Asp Tyr Val Ala
         275                  280                  285 aac ttg gtt att gct gct ggt gct aaa tct tct aag tct act gaa ttg     912
Asn Leu Val Ile Ala Ala Gly Ala Lys Ser Ser Lys Ser Thr Glu Leu
     290                  295                  300 aag gtc tac aac tgc tgt tct tct gct tgt aac cca att act atc ggt     960
Lys Val Tyr Asn Cys Cys Ser Ser Ala Cys Asn Pro Ile Thr Ile Gly
305                  310                  315                  320 aag ttg atg tcc atg ttt gct gaa gat gct atc aag caa aag tct tac    1008
```

-continued

```
                Lys Leu Met Ser Met Phe Ala Glu Asp Ala Ile Lys Gln Lys Ser Tyr
                                325                 330                 335 gct atg cca ttg cca ggt tgg tac att ttt act aag tac aag tgg ttg        1056
Ala Met Pro Leu Pro Gly Trp Tyr Ile Phe Thr Lys Tyr Lys Trp Leu
            340                 345                 350 gtc ttg ttg ttg acc att ttg ttc caa gtt att cca gcc tac att acc        1104
Val Leu Leu Leu Thr Ile Leu Phe Gln Val Ile Pro Ala Tyr Ile Thr
                355                 360                 365 gac ttg tac aga cat ttg att ggt aag aac cca aga tat atc aag ttg        1152
Asp Leu Tyr Arg His Leu Ile Gly Lys Asn Pro Arg Tyr Ile Lys Leu
            370                 375                 380 caa tcc ttg gtc aat caa acc aga tcc tcc att gat ttc ttc acc aac        1200
Gln Ser Leu Val Asn Gln Thr Arg Ser Ser Ile Asp Phe Phe Thr Asn
385                 390                 395                 400 cat tct tgg gtt atg aag gct gat aga gtc aga gaa tta ttc gct tct        1248
His Ser Trp Val Met Lys Ala Asp Arg Val Arg Glu Leu Phe Ala Ser
                405                 410                 415 ttg tct cca gca gat aag tac ttg ttt cca tgt gat cca gtc aac atc        1296
Leu Ser Pro Ala Asp Lys Tyr Leu Phe Pro Cys Asp Pro Val Asn Ile
            420                 425                 430 aat tgg aga caa tat atc caa gat tac tgc tgg ggt gtt aga cat ttc        1344
Asn Trp Arg Gln Tyr Ile Gln Asp Tyr Cys Trp Gly Val Arg His Phe
        435                 440                 445 ttg cat gat gaa ttg taa                                                 1362
Leu His Asp Glu Leu
            450

<210> SEQ ID NO 18
<211> LENGTH: 453
<212> TYPE: PRT
<213> ORGANISM: Artificial sequence
<220> FEATURE:
<223> OTHER INFORMATION: Synthetic Construct

<400> SEQUENCE: 18

Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
            20                  25                  30

Lys Val Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
```

```
                180             185                 190
Gly Ile Ser Glu Glu Thr Glu Lys Ile Leu Asn Gly Arg Pro Asn
            195                 200             205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
            275                 280                 285

Asn Leu Val Ile Ala Ala Gly Ala Lys Ser Ser Lys Ser Thr Glu Leu
        290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Val Asn Ile
            420                 425                 430

Asn Trp Arg Gln Tyr Ile Gln Asp Tyr Cys Trp Gly Val Arg His Phe
        435                 440                 445

Leu His Asp Glu Leu
    450

<210> SEQ ID NO 19
<211> LENGTH: 37
<212> TYPE: DNA
<213> ORGANISM: Artificial sequence
<220> FEATURE:
<223> OTHER INFORMATION: PR-8330 (Ase_FAR_U1_fw)
<220> FEATURE:
<221> NAME/KEY: primer_bind
<222> LOCATION: (1)..(37)
<223> OTHER INFORMATION: PR-8330 (Ase_FAR_U1_fw)

<400> SEQUENCE: 19
agtgcaggua aaacaatgcc agtcttgact tctagag                                37

<210> SEQ ID NO 20
<211> LENGTH: 25
<212> TYPE: DNA
<213> ORGANISM: Artificial sequence
<220> FEATURE:
<223> OTHER INFORMATION: Primer PR-8331 (Ase_FAR_U1_rev)
<220> FEATURE:
<221> NAME/KEY: primer_bind
<222> LOCATION: (1)..(25)
```

<223> OTHER INFORMATION: PR-8331 (Ase_FAR_U1_rev)

<400> SEQUENCE: 20
cgtgcgautt acttcttctt ttcta                                                25

<210> SEQ ID NO 21
<211> LENGTH: 37
<212> TYPE: DNA
<213> ORGANISM: Artificial sequence
<220> FEATURE:
<223> OTHER INFORMATION: PR-8332 (Har_FAR_U1_fw)
<220> FEATURE:
<221> NAME/KEY: primer_bind
<222> LOCATION: (1)..(37)
<223> OTHER INFORMATION: PR-8332 (Har_FAR_U1_fw)

<400> SEQUENCE: 21
agtgcaggua aaacaatggt tgtcttgacc tccaaag                                   37

<210> SEQ ID NO 22
<211> LENGTH: 32
<212> TYPE: DNA
<213> ORGANISM: Artificial sequence
<220> FEATURE:
<223> OTHER INFORMATION: PR-8336 (Hs_FAR_U1_fw)
<220> FEATURE:
<221> NAME/KEY: primer_bind
<222> LOCATION: (1)..(32)
<223> OTHER INFORMATION: PR-8336 (Hs_FAR_U1_fw)

<400> SEQUENCE: 22
agtgcaggua aaacaatggt tgtcttgacc tc                                        32

<210> SEQ ID NO 23
<211> LENGTH: 25
<212> TYPE: DNA
<213> ORGANISM: Artificial sequence
<220> FEATURE:
<223> OTHER INFORMATION: PR-8337 (Hs_FAR_U1_rev)
<220> FEATURE:
<221> NAME/KEY: primer_bind
<222> LOCATION: (1)..(25)
<223> OTHER INFORMATION: PR-8337 (Hs_FAR_U1_rev)

<400> SEQUENCE: 23
cgtgcgautt aagtcttttt ttcca                                                25

<210> SEQ ID NO 24
<211> LENGTH: 32
<212> TYPE: DNA
<213> ORGANISM: Artificial sequence
<220> FEATURE:
<223> OTHER INFORMATION: PR-8340 (Has_FAR_U1_fw)
<220> FEATURE:
<221> NAME/KEY: primer_bind
<222> LOCATION: (1)..(32)
<223> OTHER INFORMATION: PR-8340 (Has_FAR_U1_fw)

<400> SEQUENCE: 24
agtgcaggua aaacaatggt tgtcttgacc tc                                        32

<210> SEQ ID NO 25
<211> LENGTH: 25
<212> TYPE: DNA
<213> ORGANISM: Artificial sequence
<220> FEATURE:
<223> OTHER INFORMATION: PR-8341 (Has_FAR_U1_rev)
<220> FEATURE:
<221> NAME/KEY: primer_bind

```
<222> LOCATION: (1)..(25)
<223> OTHER INFORMATION: PR-8341 (Has_FAR_U1_rev)

<400> SEQUENCE: 25
cgtgcgautt acttgttggt agtct                                      25

<210> SEQ ID NO 26
<211> LENGTH: 36
<212> TYPE: DNA
<213> ORGANISM: Artificial sequence
<220> FEATURE:
<223> OTHER INFORMATION: PR-8350 (Atrd11_U1_fw)
<220> FEATURE:
<221> NAME/KEY: primer_bind
<222> LOCATION: (1)..(36)
<223> OTHER INFORMATION: PR-8350 (Atrd11_U1_fw)

<400> SEQUENCE: 26
agtgcaggua aaacaatggt tccaaacaag ggttcc                          36

<210> SEQ ID NO 27
<211> LENGTH: 25
<212> TYPE: DNA
<213> ORGANISM: Artificial sequence
<220> FEATURE:
<223> OTHER INFORMATION: PR-8351 (Atrd11_U1_rev)
<220> FEATURE:
<221> NAME/KEY: primer_bind
<222> LOCATION: (1)..(25)
<223> OTHER INFORMATION: PR-8351 (Atrd11_U1_rev)

<400> SEQUENCE: 27
cgtgcgautc atctctttct acccc                                      25

<210> SEQ ID NO 28
<211> LENGTH: 33
<212> TYPE: DNA
<213> ORGANISM: Artificial sequence
<220> FEATURE:
<223> OTHER INFORMATION: PR-10350 (atf1_U1_fw)
<220> FEATURE:
<221> NAME/KEY: primer_bind
<222> LOCATION: (1)..(33)
<223> OTHER INFORMATION: PR-10350 (atf1_U1_fw)

<400> SEQUENCE: 28
agtgcaggua aaacaatgaa tgaaatcgat gag                             33

<210> SEQ ID NO 29
<211> LENGTH: 33
<212> TYPE: DNA
<213> ORGANISM: Artificial sequence
<220> FEATURE:
<223> OTHER INFORMATION: PR-10351 (atf1_U1_rev)
<220> FEATURE:
<221> NAME/KEY: primer_bind
<222> LOCATION: (1)..(33)
<223> OTHER INFORMATION: PR-10351 (atf1_U1_rev)

<400> SEQUENCE: 29
cgtgcgauct aagggcctaa aaggagagct ttg                             33

<210> SEQ ID NO 30
<211> LENGTH: 46
<212> TYPE: DNA
<213> ORGANISM: Artificial sequence
<220> FEATURE:
<223> OTHER INFORMATION: PR-10738 (Har_FAR_KKSYE_U1_rev)
<220> FEATURE:
```

```
<221> NAME/KEY: primer_bind
<222> LOCATION: (1)..(46)
<223> OTHER INFORMATION: PR-10738 (Har_FAR_KKSYE_U1_rev)

<400> SEQUENCE: 30
cgtgcgautt attcgtagct ttttttttcc aagaaatgtc taacac        46

<210> SEQ ID NO 31
<211> LENGTH: 43
<212> TYPE: DNA
<213> ORGANISM: Artificial sequence
<220> FEATURE:
<223> OTHER INFORMATION: PR-10739 (Har_FAR_HDEL_U1_rev)
<220> FEATURE:
<221> NAME/KEY: primer_bind
<222> LOCATION: (1)..(43)
<223> OTHER INFORMATION: PR-10739 (Har_FAR_HDEL_U1_rev)

<400> SEQUENCE: 31
cgtgcgautt acaattcatc atgttccaag aaatgtctaa cac           43

<210> SEQ ID NO 32
<211> LENGTH: 43
<212> TYPE: DNA
<213> ORGANISM: Artificial sequence
<220> FEATURE:
<223> OTHER INFORMATION: PR-10740 (Hs_FAR_HDEL_U1_rev)
<220> FEATURE:
<221> NAME/KEY: primer_bind
<222> LOCATION: (1)..(43)
<223> OTHER INFORMATION: PR-10740 (Hs_FAR_HDEL_U1_rev)

<400> SEQUENCE: 32
cgtgcgautt acaattcatc atgcaagaaa tgtctaacac ccc           43

<210> SEQ ID NO 33
<211> LENGTH: 43
<212> TYPE: DNA
<213> ORGANISM: Artificial sequence
<220> FEATURE:
<223> OTHER INFORMATION: PR-10741 (Has_FAR_HDEL_U1_rev)
<220> FEATURE:
<221> NAME/KEY: primer_bind
<222> LOCATION: (1)..(43)
<223> OTHER INFORMATION: PR-10741 (Has_FAR_HDEL_U1_rev)

<400> SEQUENCE: 33
cgtgcgautt acaattcatc atgttccaag aagtgtctaa cac           43

<210> SEQ ID NO 34
<211> LENGTH: 2103
<212> TYPE: DNA
<213> ORGANISM: Saccharomyces cerevisiae
<220> FEATURE:
<221> NAME/KEY: CDS
<222> LOCATION: (1)..(2103)
<223> OTHER INFORMATION: FAA1

<400> SEQUENCE: 34 atg gtt gct caa tat acc gtt cca gtt ggg aaa gcc gcc aat gag cat      48
Met Val Ala Gln Tyr Thr Val Pro Val Gly Lys Ala Ala Asn Glu His
 1               5                  10                  15 gaa act gct cca aga aga aat tat caa tgc cgc gag aag ccg ctc gtc      96
Glu Thr Ala Pro Arg Arg Asn Tyr Gln Cys Arg Glu Lys Pro Leu Val
                20                  25                  30 aga ccg cct aac aca aag tgt tcc act gtt tat gag ttt gtt cta gag    144
Arg Pro Pro Asn Thr Lys Cys Ser Thr Val Tyr Glu Phe Val Leu Glu
            35                  40                  45
```

```
tgc ttt cag aag aac aaa aat tca aat gct atg ggt tgg agg gat gtt      192
Cys Phe Gln Lys Asn Lys Asn Ser Asn Ala Met Gly Trp Arg Asp Val
 50                  55                  60 aag gaa att cat gaa gaa tcc aaa tcg gtt atg aaa aaa gtt gat ggc      240
Lys Glu Ile His Glu Glu Ser Lys Ser Val Met Lys Lys Val Asp Gly
 65                  70                  75                  80 aag gag act tca gtg gaa aag aaa tgg atg tat tat gaa cta tcg cat      288
Lys Glu Thr Ser Val Glu Lys Lys Trp Met Tyr Tyr Glu Leu Ser His
                 85                  90                  95 tat cat tat aat tca ttt gac caa ttg acc gat atc atg cat gaa att      336
Tyr His Tyr Asn Ser Phe Asp Gln Leu Thr Asp Ile Met His Glu Ile
                     100                 105                 110 ggt cgt ggg ttg gtg aaa ata gga tta aag cct aat gat gat gac aaa      384
Gly Arg Gly Leu Val Lys Ile Gly Leu Lys Pro Asn Asp Asp Asp Lys
             115                 120                 125 tta cat ctt tac gca gcc act tct cac aag tgg atg aag atg ttc tta      432
Leu His Leu Tyr Ala Ala Thr Ser His Lys Trp Met Lys Met Phe Leu
130                 135                 140 gga gcg cag tct caa ggt att cct gtc gtc act gcc tac gat act ttg      480
Gly Ala Gln Ser Gln Gly Ile Pro Val Val Thr Ala Tyr Asp Thr Leu
145                 150                 155                 160 gga gag aaa ggg cta att cat tct ttg gtg caa acg ggg tct aag gcc      528
Gly Glu Lys Gly Leu Ile His Ser Leu Val Gln Thr Gly Ser Lys Ala
                 165                 170                 175 att ttt acc gat aac tct tta tta cca tcc ttg atc aaa cca gtg caa      576
Ile Phe Thr Asp Asn Ser Leu Leu Pro Ser Leu Ile Lys Pro Val Gln
                 180                 185                 190 gcc gct caa gac gta aaa tac ata att cat ttc gat tcc atc agt tct      624
Ala Ala Gln Asp Val Lys Tyr Ile Ile His Phe Asp Ser Ile Ser Ser
                 195                 200                 205 gag gac agg agg caa agt ggt aag atc tat caa tct gct cat gat gcc      672
Glu Asp Arg Arg Gln Ser Gly Lys Ile Tyr Gln Ser Ala His Asp Ala
         210                 215                 220 atc aac aga att aaa gaa gtt aga cct gat atc aag acc ttt agc ttt      720
Ile Asn Arg Ile Lys Glu Val Arg Pro Asp Ile Lys Thr Phe Ser Phe
225                 230                 235                 240 gac gac atc ttg aag cta ggt aaa gaa tcc tgt aac gaa atc gat gtt      768
Asp Asp Ile Leu Lys Leu Gly Lys Glu Ser Cys Asn Glu Ile Asp Val
                 245                 250                 255 cat cca cct ggc aag gat gat ctt tgt tgc atc atg tat acg tct ggt      816
His Pro Pro Gly Lys Asp Asp Leu Cys Cys Ile Met Tyr Thr Ser Gly
                 260                 265                 270 tct aca ggt gag cca aag ggt gtt gtc ttg aaa cat tca aat gtt gtc      864
Ser Thr Gly Glu Pro Lys Gly Val Val Leu Lys His Ser Asn Val Val
             275                 280                 285 gca ggt gtt ggt ggt gca agt ttg aat gtt ttg aag ttt gtg ggc aat      912
Ala Gly Val Gly Gly Ala Ser Leu Asn Val Leu Lys Phe Val Gly Asn
                 290                 295                 300 acc gac cgt gtt atc tgt ttt ttg cca cta gct cat att ttt gaa ttg      960
Thr Asp Arg Val Ile Cys Phe Leu Pro Leu Ala His Ile Phe Glu Leu
305                 310                 315                 320 gtt ttc gaa cta ttg tcc ttt tat tgg ggg gcc tgc att ggt tat gcc      1008
Val Phe Glu Leu Leu Ser Phe Tyr Trp Gly Ala Cys Ile Gly Tyr Ala
                 325                 330                 335 acc gta aaa act tta act agc agc tct gtg aga aat tgt caa ggt gat      1056
Thr Val Lys Thr Leu Thr Ser Ser Ser Val Arg Asn Cys Gln Gly Asp
                 340                 345                 350 ttg caa gaa ttc aag ccc aca atc atg gtt ggt gtc gcc gct gtt tgg      1104
Leu Gln Glu Phe Lys Pro Thr Ile Met Val Gly Val Ala Ala Val Trp
```

```
                355                 360                 365
gaa aca gtg aga aaa ggg atc tta aac caa att gat aat ttg ccc ttc    1152
Glu Thr Val Arg Lys Gly Ile Leu Asn Gln Ile Asp Asn Leu Pro Phe
    370                 375                 380 ctc acc aag aaa atc ttc tgg acc gcg tat aat acc aag ttg aac atg    1200
Leu Thr Lys Lys Ile Phe Trp Thr Ala Tyr Asn Thr Lys Leu Asn Met
385                 390                 395                 400 caa cgt ctc cac atc cct ggt ggc ggc gcc tta gga aac ttg gtt ttc    1248
Gln Arg Leu His Ile Pro Gly Gly Gly Ala Leu Gly Asn Leu Val Phe
                405                 410                 415 aaa aaa atc aga act gcc aca ggt ggc caa tta aga tat ttg tta aac    1296
Lys Lys Ile Arg Thr Ala Thr Gly Gly Gln Leu Arg Tyr Leu Leu Asn
            420                 425                 430 ggt ggt tct cca atc agt cgg gat gct cag gaa ttc atc aca aat tta    1344
Gly Gly Ser Pro Ile Ser Arg Asp Ala Gln Glu Phe Ile Thr Asn Leu
        435                 440                 445 atc tgc cct atg ctt att ggt tac ggt tta acc gag aca tgc gct agt    1392
Ile Cys Pro Met Leu Ile Gly Tyr Gly Leu Thr Glu Thr Cys Ala Ser
450                 455                 460 acc acc atc ttg gat cct gct aat ttt gaa ctc ggc gtc gct ggt gac    1440
Thr Thr Ile Leu Asp Pro Ala Asn Phe Glu Leu Gly Val Ala Gly Asp
465                 470                 475                 480 cta aca ggt tgt gtt acc gtc aaa cta gtt gat gtt gaa gaa tta ggt    1488
Leu Thr Gly Cys Val Thr Val Lys Leu Val Asp Val Glu Glu Leu Gly
                485                 490                 495 tat ttt gct aaa aac aac caa ggt gaa gtt tgg atc aca ggt gcc aat    1536
Tyr Phe Ala Lys Asn Asn Gln Gly Glu Val Trp Ile Thr Gly Ala Asn
            500                 505                 510 gtc acg cct gaa tat tat aag aat gag gaa gaa act tct caa gct tta    1584
Val Thr Pro Glu Tyr Tyr Lys Asn Glu Glu Glu Thr Ser Gln Ala Leu
        515                 520                 525 aca agc gat ggt tgg ttc aag acc ggt gac atc ggt gaa tgg gaa gca    1632
Thr Ser Asp Gly Trp Phe Lys Thr Gly Asp Ile Gly Glu Trp Glu Ala
530                 535                 540 aat ggc cat ttg aaa ata att gac agg aag aaa aac ttg gtc aaa aca    1680
Asn Gly His Leu Lys Ile Ile Asp Arg Lys Lys Asn Leu Val Lys Thr
545                 550                 555                 560 atg aac ggt gaa tat atc gca ctc gag aaa tta gag tcc gtt tac aga    1728
Met Asn Gly Glu Tyr Ile Ala Leu Glu Lys Leu Glu Ser Val Tyr Arg
                565                 570                 575 tct aac gaa tat gtt gct aac att tgt gtt tat gcc gac caa tct aag    1776
Ser Asn Glu Tyr Val Ala Asn Ile Cys Val Tyr Ala Asp Gln Ser Lys
            580                 585                 590 act aag cca gtt ggt att att gta cca aat cat gct cca tta acg aag    1824
Thr Lys Pro Val Gly Ile Ile Val Pro Asn His Ala Pro Leu Thr Lys
        595                 600                 605 ctt gct aaa aag ttg gga att atg gaa caa aaa gac agt tca att aat    1872
Leu Ala Lys Lys Leu Gly Ile Met Glu Gln Lys Asp Ser Ser Ile Asn
610                 615                 620 atc gaa aat tat ttg gag gat gca aaa ttg att aaa gct gtt tat tct    1920
Ile Glu Asn Tyr Leu Glu Asp Ala Lys Leu Ile Lys Ala Val Tyr Ser
625                 630                 635                 640 gat ctt ttg aag aca ggt aaa gac caa ggt ttg gtt ggc att gaa tta    1968
Asp Leu Leu Lys Thr Gly Lys Asp Gln Gly Leu Val Gly Ile Glu Leu
                645                 650                 655 cta gca ggc ata gtg ttc ttt gac ggc gaa tgg act cca caa aac ggt    2016
Leu Ala Gly Ile Val Phe Phe Asp Gly Glu Trp Thr Pro Gln Asn Gly
            660                 665                 670 ttt gtt acg tcc gct cag aaa ttg aaa aga aaa gac att ttg aat gct    2064
```

```
Phe Val Thr Ser Ala Gln Lys Leu Lys Arg Lys Asp Ile Leu Asn Ala
            675                 680                 685
gtc aaa gat aaa gtt gac gcc gtt tat agt tcg tct taa                     2103
Val Lys Asp Lys Val Asp Ala Val Tyr Ser Ser Ser
            690                 695                 700

<210> SEQ ID NO 35
<211> LENGTH: 700
<212> TYPE: PRT
<213> ORGANISM: Saccharomyces cerevisiae

<400> SEQUENCE: 35

Met Val Ala Gln Tyr Thr Val Pro Val Gly Lys Ala Ala Asn Glu His
1               5                   10                  15

Glu Thr Ala Pro Arg Arg Asn Tyr Gln Cys Arg Glu Lys Pro Leu Val
                20                  25                  30

Arg Pro Pro Asn Thr Lys Cys Ser Thr Val Tyr Glu Phe Val Leu Glu
            35                  40                  45

Cys Phe Gln Lys Asn Lys Asn Ser Asn Ala Met Gly Trp Arg Asp Val
        50                  55                  60

Lys Glu Ile His Glu Glu Ser Lys Ser Val Met Lys Lys Val Asp Gly
65                  70                  75                  80

Lys Glu Thr Ser Val Glu Lys Lys Trp Met Tyr Tyr Glu Leu Ser His
                85                  90                  95

Tyr His Tyr Asn Ser Phe Asp Gln Leu Thr Asp Ile Met His Glu Ile
                100                 105                 110

Gly Arg Gly Leu Val Lys Ile Gly Leu Lys Pro Asn Asp Asp Asp Lys
            115                 120                 125

Leu His Leu Tyr Ala Ala Thr Ser His Lys Trp Met Lys Met Phe Leu
        130                 135                 140

Gly Ala Gln Ser Gln Gly Ile Pro Val Val Thr Ala Tyr Asp Thr Leu
145                 150                 155                 160

Gly Glu Lys Gly Leu Ile His Ser Leu Val Gln Thr Gly Ser Lys Ala
                165                 170                 175

Ile Phe Thr Asp Asn Ser Leu Leu Pro Ser Leu Ile Lys Pro Val Gln
                180                 185                 190

Ala Ala Gln Asp Val Lys Tyr Ile Ile His Phe Asp Ser Ile Ser Ser
            195                 200                 205

Glu Asp Arg Arg Gln Ser Gly Lys Ile Tyr Gln Ser Ala His Asp Ala
        210                 215                 220

Ile Asn Arg Ile Lys Glu Val Arg Pro Asp Ile Lys Thr Phe Ser Phe
225                 230                 235                 240

Asp Asp Ile Leu Lys Leu Gly Lys Glu Ser Cys Asn Glu Ile Asp Val
                245                 250                 255

His Pro Pro Gly Lys Asp Asp Leu Cys Cys Ile Met Tyr Thr Ser Gly
                260                 265                 270

Ser Thr Gly Glu Pro Lys Gly Val Val Leu Lys His Ser Asn Val Val
            275                 280                 285

Ala Gly Val Gly Gly Ala Ser Leu Asn Val Leu Lys Phe Val Gly Asn
        290                 295                 300

Thr Asp Arg Val Ile Cys Phe Leu Pro Leu Ala His Ile Phe Glu Leu
305                 310                 315                 320

Val Phe Glu Leu Leu Ser Phe Tyr Trp Gly Ala Cys Ile Gly Tyr Ala
                325                 330                 335

Thr Val Lys Thr Leu Thr Ser Ser Ser Val Arg Asn Cys Gln Gly Asp
```

```
                  340                 345                 350
Leu Gln Glu Phe Lys Pro Thr Ile Met Val Gly Val Ala Ala Val Trp
            355                 360                 365

Glu Thr Val Arg Lys Gly Ile Leu Asn Gln Ile Asp Asn Leu Pro Phe
        370                 375                 380

Leu Thr Lys Lys Ile Phe Trp Thr Ala Tyr Asn Thr Lys Leu Asn Met
385                 390                 395                 400

Gln Arg Leu His Ile Pro Gly Gly Ala Leu Gly Asn Leu Val Phe
            405                 410                 415

Lys Lys Ile Arg Thr Ala Thr Gly Gly Gln Leu Arg Tyr Leu Leu Asn
            420                 425                 430

Gly Gly Ser Pro Ile Ser Arg Asp Ala Gln Glu Phe Ile Thr Asn Leu
            435                 440                 445

Ile Cys Pro Met Leu Ile Gly Tyr Gly Leu Thr Glu Thr Cys Ala Ser
            450                 455                 460

Thr Thr Ile Leu Asp Pro Ala Asn Phe Glu Leu Gly Val Ala Gly Asp
465                 470                 475                 480

Leu Thr Gly Cys Val Thr Val Lys Leu Val Asp Val Glu Glu Leu Gly
            485                 490                 495

Tyr Phe Ala Lys Asn Asn Gln Gly Glu Val Trp Ile Thr Gly Ala Asn
            500                 505                 510

Val Thr Pro Glu Tyr Tyr Lys Asn Glu Glu Thr Ser Gln Ala Leu
            515                 520                 525

Thr Ser Asp Gly Trp Phe Lys Thr Gly Asp Ile Gly Glu Trp Glu Ala
            530                 535                 540

Asn Gly His Leu Lys Ile Ile Asp Arg Lys Lys Asn Leu Val Lys Thr
545                 550                 555                 560

Met Asn Gly Glu Tyr Ile Ala Leu Glu Lys Leu Glu Ser Val Tyr Arg
                565                 570                 575

Ser Asn Glu Tyr Val Ala Asn Ile Cys Val Tyr Ala Asp Gln Ser Lys
            580                 585                 590

Thr Lys Pro Val Gly Ile Ile Val Pro Asn His Ala Pro Leu Thr Lys
            595                 600                 605

Leu Ala Lys Lys Leu Gly Ile Met Glu Gln Lys Asp Ser Ser Ile Asn
            610                 615                 620

Ile Glu Asn Tyr Leu Glu Asp Ala Lys Leu Ile Lys Ala Val Tyr Ser
625                 630                 635                 640

Asp Leu Leu Lys Thr Gly Lys Asp Gln Gly Leu Val Gly Ile Glu Leu
                645                 650                 655

Leu Ala Gly Ile Val Phe Phe Asp Gly Glu Trp Thr Pro Gln Asn Gly
            660                 665                 670

Phe Val Thr Ser Ala Gln Lys Leu Lys Arg Lys Asp Ile Leu Asn Ala
            675                 680                 685

Val Lys Asp Lys Val Asp Ala Val Tyr Ser Ser Ser
            690                 695                 700

<210> SEQ ID NO 36
<211> LENGTH: 2076
<212> TYPE: DNA
<213> ORGANISM: Yarrowia lipolytica
<220> FEATURE:
<221> NAME/KEY: CDS
<222> LOCATION: (1)..(2076)
<223> OTHER INFORMATION: FAA

<400> SEQUENCE: 36
```

-continued

| | |
|---|---|
| atg gtc gga tac aca att tcc tca aag ccc gtg tcg gtg gag gtc ggc<br>Met Val Gly Tyr Thr Ile Ser Ser Lys Pro Val Ser Val Glu Val Gly<br>1                        5                    10                   15 | 48 |
| ccc gcc aag cct ggc gag act gcc ccc cga cga aac gtc att gcc aag<br>Pro Ala Lys Pro Gly Glu Thr Ala Pro Arg Arg Asn Val Ile Ala Lys<br>                20                    25                   30 | 96 |
| gac gcc cct gtc gtc ttc ccc gac aac gac tcg tcc ctg acc acc gtc<br>Asp Ala Pro Val Val Phe Pro Asp Asn Asp Ser Ser Leu Thr Thr Val<br>         35                    40                   45 | 144 |
| tac aag ctg ttc aaa aag tac gcc gag atc aac agc gag cga aag gcc<br>Tyr Lys Leu Phe Lys Lys Tyr Ala Glu Ile Asn Ser Glu Arg Lys Ala<br>     50                   55                   60 | 192 |
| atg gga tgg cga gac acc atc gac atc cac gtg gag acc aaa cag gtg<br>Met Gly Trp Arg Asp Thr Ile Asp Ile His Val Glu Thr Lys Gln Val<br>65                        70                   75                   80 | 240 |
| acc aag gtc gtg gac gga gtg gag aag aag gtg ccc aag gaa tgg aag<br>Thr Lys Val Val Asp Gly Val Glu Lys Lys Val Pro Lys Glu Trp Lys<br>                85                    90                   95 | 288 |
| tac ttt gag atg ggc cct tac aag tgg ctc tca tac aag gag gcc ctt<br>Tyr Phe Glu Met Gly Pro Tyr Lys Trp Leu Ser Tyr Lys Glu Ala Leu<br>                100                 105                110 | 336 |
| aag ctg gtc cat gat tat gga gct ggt ctt cga cac ctc gga atc aag<br>Lys Leu Val His Asp Tyr Gly Ala Gly Leu Arg His Leu Gly Ile Lys<br>           115                   120                125 | 384 |
| ccc aag gag aag atg cac att tac gcc cag acc tcc cac cga tgg atg<br>Pro Lys Glu Lys Met His Ile Tyr Ala Gln Thr Ser His Arg Trp Met<br>130                    135                 140 | 432 |
| ctc tct ggc ctg gct tct ctg tct cag ggt att ccc att gtc act gcc<br>Leu Ser Gly Leu Ala Ser Leu Ser Gln Gly Ile Pro Ile Val Thr Ala<br>145                    150                 155                160 | 480 |
| tac gac act ctt gga gag gag ggt ctc act cga tct ctc cag gag acc<br>Tyr Asp Thr Leu Gly Glu Glu Gly Leu Thr Arg Ser Leu Gln Glu Thr<br>                165                 170                175 | 528 |
| aac tcg gtc atc atg ttt acc gac aag gct ctg ctg agc tct ctc aag<br>Asn Ser Val Ile Met Phe Thr Asp Lys Ala Leu Leu Ser Ser Leu Lys<br>180                    185                 190 | 576 |
| gtc tct ctc aag aag ggc acc gat ctg cga atc atc atc tac gga ggt<br>Val Ser Leu Lys Lys Gly Thr Asp Leu Arg Ile Ile Ile Tyr Gly Gly<br>           195                   200                205 | 624 |
| gat ctg acc ccc gac gac aag aag gcc gga aac acg gag att gac gcc<br>Asp Leu Thr Pro Asp Asp Lys Lys Ala Gly Asn Thr Glu Ile Asp Ala<br>210                    215                 220 | 672 |
| atc aag gag att gtt cca gat atg aag atc tac acc atg gac gag gtt<br>Ile Lys Glu Ile Val Pro Asp Met Lys Ile Tyr Thr Met Asp Glu Val<br>225                    230                 235                240 | 720 |
| gtc gct ctc ggc cga gaa cac ccc cac ccc gtg gag gag gtc gac tat<br>Val Ala Leu Gly Arg Glu His Pro His Pro Val Glu Glu Val Asp Tyr<br>                245                 250                255 | 768 |
| gag gac ctg gcc ttc atc atg tac acc tct ggt tct acc ggt gtc ccc<br>Glu Asp Leu Ala Phe Ile Met Tyr Thr Ser Gly Ser Thr Gly Val Pro<br>               260                 265                270 | 816 |
| aag ggt gtg gtt ctg cag cac aag cag atc ctc gcc tct gtg gcc ggt<br>Lys Gly Val Val Leu Gln His Lys Gln Ile Leu Ala Ser Val Ala Gly<br>           275                   280                285 | 864 |
| gtc acc aag atc att gac cga tct atc atc ggc aac aca gac cgg ctt<br>Val Thr Lys Ile Ile Asp Arg Ser Ile Ile Gly Asn Thr Asp Arg Leu<br>290                    295                 300 | 912 |
| ctc aac ttc ctg ccc ctc gca cac att ttc gag ttt gtg ttc gag atg<br>Leu Asn Phe Leu Pro Leu Ala His Ile Phe Glu Phe Val Phe Glu Met | 960 |

```
                305                 310                 315                 320
gtc acc ttc tgg tgg ggt gct tct ctg ggt tac gga acc gtc aag acc           1008
Val Thr Phe Trp Trp Gly Ala Ser Leu Gly Tyr Gly Thr Val Lys Thr
                    325                 330                 335 att tcc gat ctg tcc atg aag aac tgt aag gga gac att cga gag ctc           1056
Ile Ser Asp Leu Ser Met Lys Asn Cys Lys Gly Asp Ile Arg Glu Leu
        340                 345                 350 aag ccc acc atc atg gtc ggc gtt ccc gct gtc tgg gaa cct atg cga           1104
Lys Pro Thr Ile Met Val Gly Val Pro Ala Val Trp Glu Pro Met Arg
            355                 360                 365 aag ggt att ctt ggc aag atc aag gag ctg tct cct ctg atg cag cgg           1152
Lys Gly Ile Leu Gly Lys Ile Lys Glu Leu Ser Pro Leu Met Gln Arg
    370                 375                 380 gtc ttc tgg gcc tca ttt gcc gcc aag cag cgt ctc gac gag aac gga           1200
Val Phe Trp Ala Ser Phe Ala Ala Lys Gln Arg Leu Asp Glu Asn Gly
385                 390                 395                 400 ctc cct ggt gga tct atc ctc gac tcg ctc att ttc aag aag gtc aag           1248
Leu Pro Gly Gly Ser Ile Leu Asp Ser Leu Ile Phe Lys Lys Val Lys
                    405                 410                 415 gac gcc act gga ggc tgt ctc cga tac gtg tgt aac gga ggt gct cca           1296
Asp Ala Thr Gly Gly Cys Leu Arg Tyr Val Cys Asn Gly Gly Ala Pro
        420                 425                 430 gta tct gtc gac acc cag aag ttc atc acc act ctc atc tgt ccc atg           1344
Val Ser Val Asp Thr Gln Lys Phe Ile Thr Thr Leu Ile Cys Pro Met
            435                 440                 445 ctg att gga tgc ggt ctg acc gag act aca gcc aac acc acc atc atg           1392
Leu Ile Gly Cys Gly Leu Thr Glu Thr Thr Ala Asn Thr Thr Ile Met
    450                 455                 460 tcg cct aaa tcg tac gcc ttt ggc acc att ggt gag ccc acc gcc gcc           1440
Ser Pro Lys Ser Tyr Ala Phe Gly Thr Ile Gly Glu Pro Thr Ala Ala
465                 470                 475                 480 gtg acc ctc aag ctc att gac gtg cct gaa gcc ggc tac ttc gcc gag           1488
Val Thr Leu Lys Leu Ile Asp Val Pro Glu Ala Gly Tyr Phe Ala Glu
                    485                 490                 495 aac aac cag gga gag ctg tgc atc aag ggc aac gtc gtg atg aag gag           1536
Asn Asn Gln Gly Glu Leu Cys Ile Lys Gly Asn Val Val Met Lys Glu
        500                 505                 510 tac tac aag aac gag gag gag acc aag aag gcg ttc tcc gac gat ggc           1584
Tyr Tyr Lys Asn Glu Glu Glu Thr Lys Lys Ala Phe Ser Asp Asp Gly
            515                 520                 525 tat ttc ctc acc ggt gat att gcc gag tgg acc gcc aat ggc cag ctc           1632
Tyr Phe Leu Thr Gly Asp Ile Ala Glu Trp Thr Ala Asn Gly Gln Leu
    530                 535                 540 aga atc att gac cga cga aag aac ctc gtc aag acc cag aac gga gag           1680
Arg Ile Ile Asp Arg Arg Lys Asn Leu Val Lys Thr Gln Asn Gly Glu
545                 550                 555                 560 tac att gct ctg gag aag ctc gag aca cag tac cga tcg tcg tcg tac           1728
Tyr Ile Ala Leu Glu Lys Leu Glu Thr Gln Tyr Arg Ser Ser Ser Tyr
                    565                 570                 575 gtg gcc aac ctg tgt gta tac gcc gac cag aac cga gtc aag ccc att           1776
Val Ala Asn Leu Cys Val Tyr Ala Asp Gln Asn Arg Val Lys Pro Ile
        580                 585                 590 gct ctg gtc att cct aac gag ggc ccc acc aag aag ctt gcc cag agc           1824
Ala Leu Val Ile Pro Asn Glu Gly Pro Thr Lys Lys Leu Ala Gln Ser
            595                 600                 605 ttg ggc gtc gat tct gac gac tgg gac gcc gtc tgt tcc aac aaa aag           1872
Leu Gly Val Asp Ser Asp Asp Trp Asp Ala Val Cys Ser Asn Lys Lys
    610                 615                 620 gtg gtc aag gct gtg ctc aag gac atg ctc gat acc ggc cga tct ctg           1920
Val Val Lys Ala Val Leu Lys Asp Met Leu Asp Thr Gly Arg Ser Leu
```

```
Val Val Lys Ala Val Leu Lys Asp Met Leu Asp Thr Gly Arg Ser Leu
625                 630                 635                 640 ggt ctg tcc ggc att gag ctg ctg caa ggc att gtg ttg ctg cct ggc       1968
Gly Leu Ser Gly Ile Glu Leu Leu Gln Gly Ile Val Leu Leu Pro Gly
                645                 650                 655 gag tgg act cct cag aac agc tac ctg act gct gcc cag aag ctc aac       2016
Glu Trp Thr Pro Gln Asn Ser Tyr Leu Thr Ala Ala Gln Lys Leu Asn
                660                 665                 670 cga aag aag att gtg gat gat aac aag aag gaa att gat gag tgc tac       2064
Arg Lys Lys Ile Val Asp Asp Asn Lys Lys Glu Ile Asp Glu Cys Tyr
                675                 680                 685 gag cag tct tag                                                       2076
Glu Gln Ser
    690
```

<210> SEQ ID NO 37
<211> LENGTH: 691
<212> TYPE: PRT
<213> ORGANISM: Yarrowia lipolytica

<400> SEQUENCE: 37

```
Met Val Gly Tyr Thr Ile Ser Ser Lys Pro Val Ser Glu Val Gly
1               5                   10                  15

Pro Ala Lys Pro Gly Glu Thr Ala Pro Arg Arg Asn Val Ile Ala Lys
                20                  25                  30

Asp Ala Pro Val Phe Pro Asp Asn Asp Ser Ser Leu Thr Thr Val
            35                  40                  45

Tyr Lys Leu Phe Lys Lys Tyr Ala Glu Ile Asn Ser Glu Arg Lys Ala
50                  55                  60

Met Gly Trp Arg Asp Thr Ile Asp Ile His Val Glu Thr Lys Gln Val
65                  70                  75                  80

Thr Lys Val Val Asp Gly Val Glu Lys Lys Val Pro Lys Glu Trp Lys
                85                  90                  95

Tyr Phe Glu Met Gly Pro Tyr Lys Trp Leu Ser Tyr Lys Glu Ala Leu
                100                 105                 110

Lys Leu Val His Asp Tyr Gly Ala Gly Leu Arg His Leu Gly Ile Lys
            115                 120                 125

Pro Lys Glu Lys Met His Ile Tyr Ala Gln Thr Ser His Arg Trp Met
130                 135                 140

Leu Ser Gly Leu Ala Ser Leu Ser Gln Gly Ile Pro Ile Val Thr Ala
145                 150                 155                 160

Tyr Asp Thr Leu Gly Glu Glu Gly Leu Thr Arg Ser Leu Gln Glu Thr
                165                 170                 175

Asn Ser Val Ile Met Phe Thr Asp Lys Ala Leu Leu Ser Ser Leu Lys
            180                 185                 190

Val Ser Leu Lys Lys Gly Thr Asp Leu Arg Ile Ile Ile Tyr Gly Gly
        195                 200                 205

Asp Leu Thr Pro Asp Lys Lys Ala Gly Asn Thr Glu Ile Asp Ala
    210                 215                 220

Ile Lys Glu Ile Val Pro Asp Met Lys Ile Tyr Thr Met Asp Glu Val
225                 230                 235                 240

Val Ala Leu Gly Arg Glu His Pro His Pro Val Glu Glu Val Asp Tyr
                245                 250                 255

Glu Asp Leu Ala Phe Ile Met Tyr Thr Ser Gly Ser Thr Gly Val Pro
            260                 265                 270

Lys Gly Val Val Leu Gln His Lys Gln Ile Leu Ala Ser Val Ala Gly
```

```
            275                 280                 285
Val Thr Lys Ile Ile Asp Arg Ser Ile Ile Gly Asn Thr Asp Arg Leu
        290                 295                 300
Leu Asn Phe Leu Pro Leu Ala His Ile Phe Glu Phe Val Phe Glu Met
305                 310                 315                 320
Val Thr Phe Trp Trp Gly Ala Ser Leu Gly Tyr Gly Thr Val Lys Thr
                325                 330                 335
Ile Ser Asp Leu Ser Met Lys Asn Cys Lys Gly Asp Ile Arg Glu Leu
                340                 345                 350
Lys Pro Thr Ile Met Val Gly Val Pro Ala Val Trp Glu Pro Met Arg
                355                 360                 365
Lys Gly Ile Leu Gly Lys Ile Lys Glu Leu Ser Pro Leu Met Gln Arg
        370                 375                 380
Val Phe Trp Ala Ser Phe Ala Ala Lys Gln Arg Leu Asp Glu Asn Gly
385                 390                 395                 400
Leu Pro Gly Gly Ser Ile Leu Asp Ser Leu Ile Phe Lys Lys Val Lys
                405                 410                 415
Asp Ala Thr Gly Gly Cys Leu Arg Tyr Val Cys Asn Gly Gly Ala Pro
                420                 425                 430
Val Ser Val Asp Thr Gln Lys Phe Ile Thr Thr Leu Ile Cys Pro Met
                435                 440                 445
Leu Ile Gly Cys Gly Leu Thr Glu Thr Thr Ala Asn Thr Thr Ile Met
        450                 455                 460
Ser Pro Lys Ser Tyr Ala Phe Gly Thr Ile Gly Glu Pro Thr Ala Ala
465                 470                 475                 480
Val Thr Leu Lys Leu Ile Asp Val Pro Glu Ala Gly Tyr Phe Ala Glu
                485                 490                 495
Asn Asn Gln Gly Glu Leu Cys Ile Lys Gly Asn Val Val Met Lys Glu
                500                 505                 510
Tyr Tyr Lys Asn Glu Glu Glu Thr Lys Lys Ala Phe Ser Asp Asp Gly
                515                 520                 525
Tyr Phe Leu Thr Gly Asp Ile Ala Glu Trp Thr Ala Asn Gly Gln Leu
        530                 535                 540
Arg Ile Ile Asp Arg Arg Lys Asn Leu Val Lys Thr Gln Asn Gly Glu
545                 550                 555                 560
Tyr Ile Ala Leu Glu Lys Leu Glu Thr Gln Tyr Arg Ser Ser Ser Tyr
                565                 570                 575
Val Ala Asn Leu Cys Val Tyr Ala Asp Gln Asn Arg Val Lys Pro Ile
                580                 585                 590
Ala Leu Val Ile Pro Asn Glu Gly Pro Thr Lys Lys Leu Ala Gln Ser
                595                 600                 605
Leu Gly Val Asp Ser Asp Asp Trp Asp Ala Val Cys Ser Asn Lys Lys
        610                 615                 620
Val Val Lys Ala Val Leu Lys Asp Met Leu Asp Thr Gly Arg Ser Leu
625                 630                 635                 640
Gly Leu Ser Gly Ile Glu Leu Leu Gln Gly Ile Val Leu Leu Pro Gly
                645                 650                 655
Glu Trp Thr Pro Gln Asn Ser Tyr Leu Thr Ala Ala Gln Lys Leu Asn
                660                 665                 670
Arg Lys Lys Ile Val Asp Asp Asn Lys Lys Glu Ile Asp Glu Cys Tyr
                675                 680                 685
Glu Gln Ser
        690
```

```
<210> SEQ ID NO 38
<211> LENGTH: 1578
<212> TYPE: DNA
<213> ORGANISM: Saccharomyces cerevisiae
<220> FEATURE:
<221> NAME/KEY: CDS
<222> LOCATION: (1)..(1578)
<223> OTHER INFORMATION: ATF1

<400> SEQUENCE: 38 atg aat gaa atc gat gag aaa aat cag gcc ccc gtg caa caa gaa tgc      48
Met Asn Glu Ile Asp Glu Lys Asn Gln Ala Pro Val Gln Gln Glu Cys
1               5                   10                  15 ctg aaa gag atg att cag aat ggg cat gct cgg cgt atg gga tct gtt      96
Leu Lys Glu Met Ile Gln Asn Gly His Ala Arg Arg Met Gly Ser Val
            20                  25                  30 gaa gat ctg tat gtt gct ctc aac aga caa aac tta tat cga aac ttc     144
Glu Asp Leu Tyr Val Ala Leu Asn Arg Gln Asn Leu Tyr Arg Asn Phe
        35                  40                  45 tgc aca tat gga gaa ttg agt gat tac tgt act agg gat cag ctc aca     192
Cys Thr Tyr Gly Glu Leu Ser Asp Tyr Cys Thr Arg Asp Gln Leu Thr
    50                  55                  60 tta gct ttg agg gaa atc tgc ctg aaa aat cca act ctt tta cat att     240
Leu Ala Leu Arg Glu Ile Cys Leu Lys Asn Pro Thr Leu Leu His Ile
65                  70                  75                  80 gtt cta cca aca aga tgg cca aat cat gaa aat tat tat cgc agt tcc     288
Val Leu Pro Thr Arg Trp Pro Asn His Glu Asn Tyr Tyr Arg Ser Ser
                85                  90                  95 gaa tac tat tca cgg cca cat cca gtg cat gat tat att tca gta tta     336
Glu Tyr Tyr Ser Arg Pro His Pro Val His Asp Tyr Ile Ser Val Leu
            100                 105                 110 caa gaa ttg aaa ctg agt ggt gtg gtt ctc aat gaa caa cct gag tac     384
Gln Glu Leu Lys Leu Ser Gly Val Val Leu Asn Glu Gln Pro Glu Tyr
        115                 120                 125 agt gca gta atg aag caa ata tta gaa gaa ttc aaa aat agt aag ggt     432
Ser Ala Val Met Lys Gln Ile Leu Glu Glu Phe Lys Asn Ser Lys Gly
    130                 135                 140 tcc tat act gca aaa att ttt aaa ctt act acc act ttg act att cct     480
Ser Tyr Thr Ala Lys Ile Phe Lys Leu Thr Thr Thr Leu Thr Ile Pro
145                 150                 155                 160 tac ttt gga cca aca gga ccg agt tgg cgg cta att tgt ctt cca gaa     528
Tyr Phe Gly Pro Thr Gly Pro Ser Trp Arg Leu Ile Cys Leu Pro Glu
                165                 170                 175 gag cac aca gaa aag tgg aaa aaa ttt atc ttt gta tct aat cat tgc     576
Glu His Thr Glu Lys Trp Lys Lys Phe Ile Phe Val Ser Asn His Cys
            180                 185                 190 atg tct gat ggt cgg tct tcg atc cac ttt ttt cat gat tta aga gac     624
Met Ser Asp Gly Arg Ser Ser Ile His Phe Phe His Asp Leu Arg Asp
        195                 200                 205 gaa tta aat aat att aaa act cca cca aaa aaa tta gat tac att ttc     672
Glu Leu Asn Asn Ile Lys Thr Pro Pro Lys Lys Leu Asp Tyr Ile Phe
    210                 215                 220 aag tac gag gag gat tac caa tta ttg agg aaa ctt cca gaa ccg atc     720
Lys Tyr Glu Glu Asp Tyr Gln Leu Leu Arg Lys Leu Pro Glu Pro Ile
225                 230                 235                 240 gaa aag gtg ata gac ttt aga cca ccg tac ttg ttt att ccg aag tca     768
Glu Lys Val Ile Asp Phe Arg Pro Pro Tyr Leu Phe Ile Pro Lys Ser
                245                 250                 255 ctt ctt tcg ggt ttc atc tac aat cat ttg aga ttt tct tca aaa ggt     816
Leu Leu Ser Gly Phe Ile Tyr Asn His Leu Arg Phe Ser Ser Lys Gly
```

-continued

```
                260                 265                 270
gtc tgt atg aga atg gat gat gtg gaa aaa acc gat gat gtt gtc acc      864
Val Cys Met Arg Met Asp Asp Val Glu Lys Thr Asp Asp Val Val Thr
            275                 280                 285 gag atc atc aat att tca cca aca gaa ttt caa gcg att aaa gca aat      912
Glu Ile Ile Asn Ile Ser Pro Thr Glu Phe Gln Ala Ile Lys Ala Asn
        290                 295                 300 att aaa tca aat atc caa ggt aag tgt act atc act ccg ttt tta cat     960
Ile Lys Ser Asn Ile Gln Gly Lys Cys Thr Ile Thr Pro Phe Leu His
305                 310                 315                 320 gtt tgt tgg ttt gta tct ctt cat aaa tgg ggt aaa ttt ttc aaa cca    1008
Val Cys Trp Phe Val Ser Leu His Lys Trp Gly Lys Phe Phe Lys Pro
                325                 330                 335 ttg aac ttc gaa tgg ctt acg gat att ttt atc ccc gca gat tgc cgc    1056
Leu Asn Phe Glu Trp Leu Thr Asp Ile Phe Ile Pro Ala Asp Cys Arg
            340                 345                 350 tca caa cta cca gat gat gat gaa atg aga cag atg tac aga tat ggc    1104
Ser Gln Leu Pro Asp Asp Asp Glu Met Arg Gln Met Tyr Arg Tyr Gly
        355                 360                 365 gct aac gtt gga ttt att gac ttc acc ccc tgg ata agc gaa ttt gac    1152
Ala Asn Val Gly Phe Ile Asp Phe Thr Pro Trp Ile Ser Glu Phe Asp
370                 375                 380 atg aat gat aac aaa gaa aat ttt tgg cca ctt att gag cac tac cat    1200
Met Asn Asp Asn Lys Glu Asn Phe Trp Pro Leu Ile Glu His Tyr His
385                 390                 395                 400 gaa gta att tcg gaa gct tta aga aat aaa aag cat ctc cat ggc tta    1248
Glu Val Ile Ser Glu Ala Leu Arg Asn Lys Lys His Leu His Gly Leu
                405                 410                 415 ggg ttc aat ata caa ggc ttc gtt caa aaa tat gtg aac att gac aag    1296
Gly Phe Asn Ile Gln Gly Phe Val Gln Lys Tyr Val Asn Ile Asp Lys
            420                 425                 430 gta atg tgc gat cgt gcc atc ggg aaa aga cgc gga ggt aca ttg tta    1344
Val Met Cys Asp Arg Ala Ile Gly Lys Arg Arg Gly Gly Thr Leu Leu
        435                 440                 445 agc aat gta ggt ctg ttt aat cag tta gag gag ccc gat gcc aaa tat    1392
Ser Asn Val Gly Leu Phe Asn Gln Leu Glu Glu Pro Asp Ala Lys Tyr
450                 455                 460 tct ata tgc gat ttg gca ttt ggc caa ttt caa gga tcc tgg cac caa    1440
Ser Ile Cys Asp Leu Ala Phe Gly Gln Phe Gln Gly Ser Trp His Gln
465                 470                 475                 480 gca ttt tcc ttg ggt gtt tgt tcg act aat gta aag ggg atg aat att    1488
Ala Phe Ser Leu Gly Val Cys Ser Thr Asn Val Lys Gly Met Asn Ile
                485                 490                 495 gtt gtt gct tca aca aag aat gtt gtt ggt agt caa gaa tct ctc gaa    1536
Val Val Ala Ser Thr Lys Asn Val Val Gly Ser Gln Glu Ser Leu Glu
            500                 505                 510 gag ctt tgc tcc att tac aaa gct ctc ctt tta ggc cct tag            1578
Glu Leu Cys Ser Ile Tyr Lys Ala Leu Leu Leu Gly Pro
        515                 520                 525

<210> SEQ ID NO 39
<211> LENGTH: 525
<212> TYPE: PRT
<213> ORGANISM: Saccharomyces cerevisiae

<400> SEQUENCE: 39

Met Asn Glu Ile Asp Glu Lys Asn Gln Ala Pro Val Gln Gln Glu Cys
1               5                   10                  15

Leu Lys Glu Met Ile Gln Asn Gly His Ala Arg Arg Met Gly Ser Val
            20                  25                  30
```

```
Glu Asp Leu Tyr Val Ala Leu Asn Arg Gln Asn Leu Tyr Arg Asn Phe
        35                  40                  45

Cys Thr Tyr Gly Glu Leu Ser Asp Tyr Cys Thr Arg Asp Gln Leu Thr
    50                  55                  60

Leu Ala Leu Arg Glu Ile Cys Leu Lys Asn Pro Thr Leu Leu His Ile
65                  70                  75                  80

Val Leu Pro Thr Arg Trp Pro Asn His Glu Asn Tyr Tyr Arg Ser Ser
                85                  90                  95

Glu Tyr Tyr Ser Arg Pro His Pro Val His Asp Tyr Ile Ser Val Leu
                100                 105                 110

Gln Glu Leu Lys Leu Ser Gly Val Val Leu Asn Glu Gln Pro Glu Tyr
                115                 120                 125

Ser Ala Val Met Lys Gln Ile Leu Glu Glu Phe Lys Asn Ser Lys Gly
            130                 135                 140

Ser Tyr Thr Ala Lys Ile Phe Lys Leu Thr Thr Thr Leu Thr Ile Pro
145                 150                 155                 160

Tyr Phe Gly Pro Thr Gly Pro Ser Trp Arg Leu Ile Cys Leu Pro Glu
                165                 170                 175

Glu His Thr Glu Lys Trp Lys Lys Phe Ile Phe Val Ser Asn His Cys
                180                 185                 190

Met Ser Asp Gly Arg Ser Ser Ile His Phe His Asp Leu Arg Asp
            195                 200                 205

Glu Leu Asn Asn Ile Lys Thr Pro Pro Lys Lys Leu Asp Tyr Ile Phe
    210                 215                 220

Lys Tyr Glu Glu Asp Tyr Gln Leu Leu Arg Lys Leu Pro Glu Pro Ile
225                 230                 235                 240

Glu Lys Val Ile Asp Phe Arg Pro Pro Tyr Leu Phe Ile Pro Lys Ser
                245                 250                 255

Leu Leu Ser Gly Phe Ile Tyr Asn His Leu Arg Phe Ser Ser Lys Gly
            260                 265                 270

Val Cys Met Arg Met Asp Asp Val Glu Lys Thr Asp Asp Val Val Thr
        275                 280                 285

Glu Ile Ile Asn Ile Ser Pro Thr Glu Phe Gln Ala Ile Lys Ala Asn
    290                 295                 300

Ile Lys Ser Asn Ile Gln Gly Lys Cys Thr Ile Thr Pro Phe Leu His
305                 310                 315                 320

Val Cys Trp Phe Val Ser Leu His Lys Trp Gly Lys Phe Phe Lys Pro
                325                 330                 335

Leu Asn Phe Glu Trp Leu Thr Asp Ile Phe Ile Pro Ala Asp Cys Arg
            340                 345                 350

Ser Gln Leu Pro Asp Asp Asp Glu Met Arg Gln Met Tyr Arg Tyr Gly
            355                 360                 365

Ala Asn Val Gly Phe Ile Asp Phe Thr Pro Trp Ile Ser Glu Phe Asp
        370                 375                 380

Met Asn Asp Asn Lys Glu Asn Phe Trp Pro Leu Ile Glu His Tyr His
385                 390                 395                 400

Glu Val Ile Ser Glu Ala Leu Arg Asn Lys His Leu His Gly Leu
                405                 410                 415

Gly Phe Asn Ile Gln Gly Phe Val Gln Lys Tyr Val Asn Ile Asp Lys
                420                 425                 430

Val Met Cys Asp Arg Ala Ile Gly Lys Arg Arg Gly Gly Thr Leu Leu
        435                 440                 445
```

```
Ser Asn Val Gly Leu Phe Asn Gln Leu Glu Glu Pro Asp Ala Lys Tyr
    450                 455                 460

Ser Ile Cys Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
                485                 490                 495

Val Val Ala Ser Thr Lys Asn Val Val Gly Ser Gln Glu Ser Leu Glu
                500                 505                 510

Glu Leu Cys Ser Ile Tyr Lys Ala Leu Leu Leu Gly Pro
            515                 520                 525

<210> SEQ ID NO 40
<211> LENGTH: 1470
<212> TYPE: DNA
<213> ORGANISM: Spodoptera littoralis
<220> FEATURE:
<221> NAME/KEY: mRNA
<222> LOCATION: (1)..(1470)
<223> OTHER INFORMATION: mRNA coding sequence of delta 11 desaturase

<400> SEQUENCE: 40
```

| | | | | | |
|---|---|---|---|---|---|
| ggacactgac | atggactgaa | ggagtagaga | atcggcccgt | ggagttggcc | ttcattttca | 60 |
| gtcttatctc | tcggtgttat | ggtagtcact | tatatcggta | ttaaaataag | tgaataaggc | 120 |
| ttgtaaaaat | ggcgcaatgt | gtacaaacaa | caacgatttt | ggaacaaaaa | gaagagaaaa | 180 |
| cagtaacttt | gctggtacct | caagcgggaa | agaggaagtt | tgaaattgtg | tattttaata | 240 |
| tcatcacctt | cgcttactgg | catatagctg | gactatatgg | cctttatttg | tgcttcactt | 300 |
| caacaaaatg | ggcgacagtt | ttattctcat | tctttctatt | cgtcgtagca | gaagtagggg | 360 |
| tcacggctgg | ctcccacaga | ctttggtcgc | ataaaactta | caaagcaaaa | ctacctttac | 420 |
| aaattctgct | aatggtgatg | aattcccttg | catttcaaaa | cacagtcatt | gattgggtga | 480 |
| gagaccatcg | actccatcat | aagtatagcg | acactgatgc | cgatccccat | aatgcctccc | 540 |
| gaggattttt | ctattcgcac | gtcggttggc | tgcttgtgag | aaaacaccct | gatgtcaaga | 600 |
| aacgaggaaa | ggaaattgat | atatctgata | tttacaacaa | tccggtactg | aggttccaga | 660 |
| agaagtacgc | aattccttc | atcggggcag | tttgtttcgt | cttaccaaca | ttgataccgg | 720 |
| tttacggttg | gggagaaacc | tggactaatg | cctggcacgt | cgccatgctg | cggtacatta | 780 |
| tgaaccttaa | cgtcaccttc | ctggtcaaca | gcgctgctca | tatatatgga | aagagacctt | 840 |
| atgacaagaa | gatcctacca | tctcaaaaca | tagctgtgtc | cattgcaacc | tttggggaag | 900 |
| gtttccataa | ttatcatcat | gtatttccat | gggattatcg | cgcagctgaa | cttggaaata | 960 |
| acagtttgaa | tttccctacg | aaatttattg | atttctttgc | gtggatcgga | tgggcgtatg | 1020 |
| acctaaagac | tgtttcgaaa | gaaatgataa | aacaaggtc | aaaagaact | ggtgatggaa | 1080 |
| ctaatctatg | ggggttagaa | gatgtggata | ccccggagga | tttaaaaaat | acaaaaggcg | 1140 |
| aataggcaaa | cccttaaact | caaacagtga | ggtttaatgt | gatatttaga | attagaatta | 1200 |
| atttatttga | aattaaatga | aggttttgga | taactgtttt | taataataaa | aatagttttt | 1260 |
| cgattaaatt | ccttagatta | tttttaaagga | aatgtataag | gtactcgcgt | ggttagcaac | 1320 |
| ccagcagtcc | ctgtttatct | gtttttatga | atttattcta | tgaatgtaga | tgtcgcatga | 1380 |
| aattttaaaa | tgttgcattt | gtataatttt | acttatgaat | aaataaattt | attttttaaa | 1440 |
| aaaaaaaaa | aaaaaaaaaa | aaaaaaaaaa | | | | 1470 |

<210> SEQ ID NO 41

-continued

```
<211> LENGTH: 338
<212> TYPE: PRT
<213> ORGANISM: Spodoptera littoralis
<220> FEATURE:
<221> NAME/KEY: PEPTIDE
<222> LOCATION: (1)..(338)
<223> OTHER INFORMATION: delta 11 desaturase

<400> SEQUENCE: 41

Met Ala Gln Cys Val Gln Thr Thr Ile Leu Glu Gln Lys Glu Glu
1               5                   10                  15

Lys Thr Val Thr Leu Leu Val Pro Gln Ala Gly Lys Arg Lys Phe Glu
            20                  25                  30

Ile Val Tyr Phe Asn Ile Ile Thr Phe Ala Tyr Trp His Ile Ala Gly
            35                  40                  45

Leu Tyr Gly Leu Tyr Leu Cys Phe Thr Ser Thr Lys Trp Ala Thr Val
50                  55                  60

Leu Phe Ser Phe Phe Leu Phe Val Ala Glu Val Gly Val Thr Ala
65                  70                  75                  80

Gly Ser His Arg Leu Trp Ser His Lys Thr Tyr Lys Ala Lys Leu Pro
                85                  90                  95

Leu Gln Ile Leu Leu Met Val Met Asn Ser Leu Ala Phe Gln Asn Thr
            100                 105                 110

Val Ile Asp Trp Val Arg Asp His Arg Leu His His Lys Tyr Ser Asp
            115                 120                 125

Thr Asp Ala Asp Pro His Asn Ala Ser Arg Gly Phe Phe Tyr Ser His
130                 135                 140

Val Gly Trp Leu Leu Val Arg Lys His Pro Asp Val Lys Lys Arg Gly
145                 150                 155                 160

Lys Glu Ile Asp Ile Ser Asp Ile Tyr Asn Asn Pro Val Leu Arg Phe
                165                 170                 175

Gln Lys Lys Tyr Ala Ile Pro Phe Ile Gly Ala Val Cys Phe Val Leu
            180                 185                 190

Pro Thr Leu Ile Pro Val Tyr Gly Trp Gly Glu Thr Trp Thr Asn Ala
            195                 200                 205

Trp His Val Ala Met Leu Arg Tyr Ile Met Asn Leu Asn Val Thr Phe
210                 215                 220

Leu Val Asn Ser Ala Ala His Ile Tyr Gly Lys Arg Pro Tyr Asp Lys
225                 230                 235                 240

Lys Ile Leu Pro Ser Gln Asn Ile Ala Val Ser Ile Ala Thr Phe Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Phe Pro Thr Lys Phe Ile Asp
            275                 280                 285

Phe Phe Ala Trp Ile Gly Trp Ala Tyr Asp Leu Lys Thr Val Ser Lys
290                 295                 300

Glu Met Ile Lys Gln Arg Ser Lys Arg Thr Gly Asp Gly Thr Asn Leu
305                 310                 315                 320

Trp Gly Leu Glu Asp Val Asp Thr Pro Glu Asp Leu Lys Asn Thr Lys
                325                 330                 335

Gly Glu

<210> SEQ ID NO 42
<211> LENGTH: 1011
<212> TYPE: DNA
```

<213> ORGANISM: Agrotis segetum
<220> FEATURE:
<221> NAME/KEY: CDS
<222> LOCATION: (1)..(1011)
<223> OTHER INFORMATION: delta 11 desaturase

<400> SEQUENCE: 42

| | | | | | | | | | | | | | | | | |
|---|---|---|---|---|---|---|---|---|---|---|---|---|---|---|---|---|
| atg | gct | caa | ggt | gtc | caa | aca | act | acg | ata | ttg | agg | gag | gaa | gag | ccg | 48 |
| Met | Ala | Gln | Gly | Val | Gln | Thr | Thr | Thr | Ile | Leu | Arg | Glu | Glu | Glu | Pro | |
| 1 | | | | 5 | | | | | 10 | | | | | 15 | | |
| tca | ttg | act | ttc | gtg | gta | cct | caa | gaa | ccg | aga | aag | tat | caa | atc | gtg | 96 |
| Ser | Leu | Thr | Phe | Val | Val | Pro | Gln | Glu | Pro | Arg | Lys | Tyr | Gln | Ile | Val | |
| | | | 20 | | | | | 25 | | | | | 30 | | | |
| tac | cca | aac | ctt | atc | aca | ttt | ggg | tac | tgg | cat | ata | gct | ggt | tta | tac | 144 |
| Tyr | Pro | Asn | Leu | Ile | Thr | Phe | Gly | Tyr | Trp | His | Ile | Ala | Gly | Leu | Tyr | |
| | | 35 | | | | | 40 | | | | | 45 | | | | |
| ggg | cta | tat | ttg | tgc | ttt | act | tcg | gca | aaa | tgg | caa | aca | att | tta | ttc | 192 |
| Gly | Leu | Tyr | Leu | Cys | Phe | Thr | Ser | Ala | Lys | Trp | Gln | Thr | Ile | Leu | Phe | |
| 50 | | | | | 55 | | | | | 60 | | | | | | |
| agt | ttc | atg | ctc | gtt | gtg | tta | gca | gag | ttg | gga | ata | aca | gcc | ggc | gct | 240 |
| Ser | Phe | Met | Leu | Val | Val | Leu | Ala | Glu | Leu | Gly | Ile | Thr | Ala | Gly | Ala | |
| 65 | | | | 70 | | | | | 75 | | | | | 80 | | |
| cac | agg | tta | tgg | gcc | cac | aaa | aca | tat | aaa | gcg | aag | ctt | ccc | tta | caa | 288 |
| His | Arg | Leu | Trp | Ala | His | Lys | Thr | Tyr | Lys | Ala | Lys | Leu | Pro | Leu | Gln | |
| | | | | 85 | | | | | 90 | | | | | 95 | | |
| att | atc | ctg | atg | ata | ctg | aac | tcc | att | gcc | ttc | caa | aat | tcc | gcc | att | 336 |
| Ile | Ile | Leu | Met | Ile | Leu | Asn | Ser | Ile | Ala | Phe | Gln | Asn | Ser | Ala | Ile | |
| | | | 100 | | | | | 105 | | | | | 110 | | | |
| gat | tgg | gtg | agg | gac | cac | cgt | ctc | cat | cat | aag | tac | agt | gac | act | gat | 384 |
| Asp | Trp | Val | Arg | Asp | His | Arg | Leu | His | His | Lys | Tyr | Ser | Asp | Thr | Asp | |
| | | | 115 | | | | | 120 | | | | | 125 | | | |
| gca | gac | cct | cac | aat | gct | act | cgt | ggt | ttc | ttc | tat | tct | cat | gtt | gga | 432 |
| Ala | Asp | Pro | His | Asn | Ala | Thr | Arg | Gly | Phe | Phe | Tyr | Ser | His | Val | Gly | |
| 130 | | | | | 135 | | | | | 140 | | | | | | |
| tgg | ttg | ctc | gta | aga | aaa | cat | cca | gaa | gtc | aag | aga | cgt | gga | aag | gaa | 480 |
| Trp | Leu | Leu | Val | Arg | Lys | His | Pro | Glu | Val | Lys | Arg | Arg | Gly | Lys | Glu | |
| 145 | | | | | 150 | | | | | 155 | | | | | 160 | |
| ctt | gac | atg | tct | gat | att | tac | aac | aat | cca | gtg | ctg | aga | ttt | caa | aag | 528 |
| Leu | Asp | Met | Ser | Asp | Ile | Tyr | Asn | Asn | Pro | Val | Leu | Arg | Phe | Gln | Lys | |
| | | | | 165 | | | | | 170 | | | | | 175 | | |
| aag | tat | gct | ata | ccc | ttc | atc | ggg | gca | atg | tgc | ttc | gga | tta | cca | act | 576 |
| Lys | Tyr | Ala | Ile | Pro | Phe | Ile | Gly | Ala | Met | Cys | Phe | Gly | Leu | Pro | Thr | |
| | | | 180 | | | | | 185 | | | | | 190 | | | |
| ttt | atc | cct | gtt | tac | ttc | tgg | gga | gaa | acc | tgg | agt | aat | gct | tgg | cat | 624 |
| Phe | Ile | Pro | Val | Tyr | Phe | Trp | Gly | Glu | Thr | Trp | Ser | Asn | Ala | Trp | His | |
| | | 195 | | | | | 200 | | | | | 205 | | | | |
| atc | acc | atg | ctt | cgg | tac | atc | ctc | aac | cta | aac | att | act | ttc | ctg | gtc | 672 |
| Ile | Thr | Met | Leu | Arg | Tyr | Ile | Leu | Asn | Leu | Asn | Ile | Thr | Phe | Leu | Val | |
| | 210 | | | | | 215 | | | | | 220 | | | | | |
| aac | agt | gct | gct | cat | atc | tgg | gga | tac | aaa | cct | tat | gac | atc | aaa | ata | 720 |
| Asn | Ser | Ala | Ala | His | Ile | Trp | Gly | Tyr | Lys | Pro | Tyr | Asp | Ile | Lys | Ile | |
| 225 | | | | | 230 | | | | | 235 | | | | | 240 | |
| ttg | cct | gcc | caa | aat | ata | gca | gtt | tcc | ata | gta | acc | ggc | ggc | gaa | gtt | 768 |
| Leu | Pro | Ala | Gln | Asn | Ile | Ala | Val | Ser | Ile | Val | Thr | Gly | Gly | Glu | Val | |
| | | | | 245 | | | | | 250 | | | | | 255 | | |
| tcc | ata | act | acc | acc | acg | ttt | ttt | cct | tgg | gat | tat | cgt | gca | gca | gaa | 816 |
| Ser | Ile | Thr | Thr | Thr | Thr | Phe | Phe | Pro | Trp | Asp | Tyr | Arg | Ala | Ala | Glu | |
| | | | 260 | | | | | 265 | | | | | 270 | | | |
| ttg | ggg | aac | aat | tat | ctt | aat | ttg | acg | act | aag | ttc | ata | gat | ttc | ttc | 864 |
| Leu | Gly | Asn | Asn | Tyr | Leu | Asn | Leu | Thr | Thr | Lys | Phe | Ile | Asp | Phe | Phe | |
| | | | 275 | | | | | 280 | | | | | 285 | | | |

```
gct tgg atc gga tgg gct tac gat ctt aag acg gtg tcc agt gat gtt       912
Ala Trp Ile Gly Trp Ala Tyr Asp Leu Lys Thr Val Ser Ser Asp Val
290                 295                 300 ata aaa agt aag gcg gaa aga act ggt gat ggg acg aat ctt tgg ggt       960
Ile Lys Ser Lys Ala Glu Arg Thr Gly Asp Gly Thr Asn Leu Trp Gly
305                 310                 315                 320 tta gaa gac aaa ggt gaa gaa gat ttt ttg aaa atc tgg aaa gac aat      1008
Leu Glu Asp Lys Gly Glu Glu Asp Phe Leu Lys Ile Trp Lys Asp Asn
                325                 330                 335 taa                                                                  1011

<210> SEQ ID NO 43
<211> LENGTH: 336
<212> TYPE: PRT
<213> ORGANISM: Agrotis segetum

<400> SEQUENCE: 43

Met Ala Gln Gly Val Gln Thr Thr Thr Ile Leu Arg Glu Glu Pro
1               5                   10                  15

Ser Leu Thr Phe Val Val Pro Gln Glu Pro Arg Lys Tyr Gln Ile Val
                20                  25                  30

Tyr Pro Asn Leu Ile Thr Phe Gly Tyr Trp His Ile Ala Gly Leu Tyr
            35                  40                  45

Gly Leu Tyr Leu Cys Phe Thr Ser Ala Lys Trp Gln Thr Ile Leu Phe
50                  55                  60

Ser Phe Met Leu Val Val Leu Ala Glu Leu Gly Ile Thr Ala Gly Ala
65                  70                  75                  80

His Arg Leu Trp Ala His Lys Thr Tyr Lys Ala Lys Leu Pro Leu Gln
                85                  90                  95

Ile Ile Leu Met Ile Leu Asn Ser Ile Ala Phe Gln Asn Ser Ala Ile
            100                 105                 110

Asp Trp Val Arg Asp His Arg Leu His His Lys Tyr Ser Asp Thr Asp
            115                 120                 125

Ala Asp Pro His Asn Ala Thr Arg Gly Phe Phe Tyr Ser His Val Gly
            130                 135                 140

Trp Leu Leu Val Arg Lys His Pro Glu Val Lys Arg Gly Lys Glu
145                 150                 155                 160

Leu Asp Met Ser Asp Ile Tyr Asn Asn Pro Val Leu Arg Phe Gln Lys
                165                 170                 175

Lys Tyr Ala Ile Pro Phe Ile Gly Ala Met Cys Phe Gly Leu Pro Thr
            180                 185                 190

Phe Ile Pro Val Tyr Phe Trp Gly Glu Thr Trp Ser Asn Ala Trp His
        195                 200                 205

Ile Thr Met Leu Arg Tyr Ile Leu Asn Leu Asn Ile Thr Phe Leu Val
            210                 215                 220

Asn Ser Ala Ala His Ile Trp Gly Tyr Lys Pro Tyr Asp Ile Lys Ile
225                 230                 235                 240

Leu Pro Ala Gln Asn Ile Ala Val Ser Ile Val Thr Gly Gly Glu Val
                245                 250                 255

Ser Ile Thr Thr Thr Phe Phe Pro Trp Asp Tyr Arg Ala Ala Glu
            260                 265                 270

Leu Gly Asn Asn Tyr Leu Asn Leu Thr Thr Lys Phe Ile Asp Phe Phe
        275                 280                 285

Ala Trp Ile Gly Trp Ala Tyr Asp Leu Lys Thr Val Ser Ser Asp Val
290                 295                 300
```

```
Ile Lys Ser Lys Ala Glu Arg Thr Gly Asp Gly Thr Asn Leu Trp Gly
305                 310                 315                 320

Leu Glu Asp Lys Gly Glu Asp Phe Leu Lys Ile Trp Lys Asp Asn
                325                 330                 335

<210> SEQ ID NO 44
<211> LENGTH: 1050
<212> TYPE: DNA
<213> ORGANISM: Trichoplusia ni
<220> FEATURE:
<221> NAME/KEY: CDS
<222> LOCATION: (1)..(1050)
<223> OTHER INFORMATION: delta 11 desaturase

<400> SEQUENCE: 44 atg gct gtg atg gct caa aca gta caa gaa acg gct aca gtg ttg gaa      48
Met Ala Val Met Ala Gln Thr Val Gln Glu Thr Ala Thr Val Leu Glu
1               5                   10                  15 gag gaa gct cgc aca gtg act ctt gtg gct cca aag aca acg cca agg      96
Glu Glu Ala Arg Thr Val Thr Leu Val Ala Pro Lys Thr Thr Pro Arg
                20                  25                  30 aaa tat aaa tat ata tac acc aac ttt ctt aca ttt tca tat gcg cat     144
Lys Tyr Lys Tyr Ile Tyr Thr Asn Phe Leu Thr Phe Ser Tyr Ala His
            35                  40                  45 tta gct gca tta tac gga ctt tat ttg tgc ttc acc tct gcg aaa tgg     192
Leu Ala Ala Leu Tyr Gly Leu Tyr Leu Cys Phe Thr Ser Ala Lys Trp
        50                  55                  60 gaa aca ttg cta ttc tct ttc gta ctc ttc cac atg tca aat ata ggc     240
Glu Thr Leu Leu Phe Ser Phe Val Leu Phe His Met Ser Asn Ile Gly
65                  70                  75                  80 atc acc gca ggg gct cac cga ctc tgg act cac aag act ttc aaa gcc     288
Ile Thr Ala Gly Ala His Arg Leu Trp Thr His Lys Thr Phe Lys Ala
                85                  90                  95 aaa ttg cct ttg gaa att gtc ctc atg ata ttc aac tct tta gcc ttt     336
Lys Leu Pro Leu Glu Ile Val Leu Met Ile Phe Asn Ser Leu Ala Phe
            100                 105                 110 caa aac acg gct att aca tgg gct aga gaa cat cgg cta cat cac aaa     384
Gln Asn Thr Ala Ile Thr Trp Ala Arg Glu His Arg Leu His His
        115                 120                 125 tac agc gat act gat gct gat ccc cac aat gcg tca aga ggg ttc ttc     432
Tyr Ser Asp Thr Asp Ala Asp Pro His Asn Ala Ser Arg Gly Phe Phe
    130                 135                 140 tac tcg cat gtt ggc tgg cta tta gta aaa aaa cat ccc gat gtc ctg     480
Tyr Ser His Val Gly Trp Leu Leu Val Lys Lys His Pro Asp Val Leu
145                 150                 155                 160 aaa tat gga aaa act ata gac atg tcg gat gta tac aat aat cct gtg     528
Lys Tyr Gly Lys Thr Ile Asp Met Ser Asp Val Tyr Asn Asn Pro Val
                165                 170                 175 tta aaa ttt cag aaa aag tac gca gta ccc tta att gga aca gtt tgt     576
Leu Lys Phe Gln Lys Lys Tyr Ala Val Pro Leu Ile Gly Thr Val Cys
            180                 185                 190 ttt gct ctt cca act ttg att cca gtc tac tgt tgg ggc gaa tcg tgg     624
Phe Ala Leu Pro Thr Leu Ile Pro Val Tyr Cys Trp Gly Glu Ser Trp
        195                 200                 205 aac aac gct tgg cac ata gcc tta ttt cga tac ata ttc aat ctt aac     672
Asn Asn Ala Trp His Ile Ala Leu Phe Arg Tyr Ile Phe Asn Leu Asn
    210                 215                 220 gtg act ttc cta gtc aac agt gct gcg cat atc tgg ggg aat aag cct     720
Val Thr Phe Leu Val Asn Ser Ala Ala His Ile Trp Gly Asn Lys Pro
225                 230                 235                 240
```

```
tat gat aaa agc atc ttg ccc gct caa aac ctg ctg gtt tcc ttc cta      768
Tyr Asp Lys Ser Ile Leu Pro Ala Gln Asn Leu Leu Val Ser Phe Leu
            245                 250                 255 gca agt gga gaa ggc ttc cat aat tac cat cac gtc ttt cca tgg gat      816
Ala Ser Gly Glu Gly Phe His Asn Tyr His His Val Phe Pro Trp Asp
                260                 265                 270 tac cgc aca gca gaa tta ggg aat aac ttc ctg aat ttg acg acg ctg      864
Tyr Arg Thr Ala Glu Leu Gly Asn Asn Phe Leu Asn Leu Thr Thr Leu
            275                 280                 285 ttc att gat ttt tgt gcc tgg ttt gga tgg gct tat gac ttg aag tct      912
Phe Ile Asp Phe Cys Ala Trp Phe Gly Trp Ala Tyr Asp Leu Lys Ser
        290                 295                 300 gta tca gag gat att ata aaa cag aga gct aaa cga aca ggt gac ggt      960
Val Ser Glu Asp Ile Ile Lys Gln Arg Ala Lys Arg Thr Gly Asp Gly
305                 310                 315                 320 tct tca ggg gtc att tgg gga tgg gac gac aaa gac atg gac cgc gat     1008
Ser Ser Gly Val Ile Trp Gly Trp Asp Asp Lys Asp Met Asp Arg Asp
                325                 330                 335 ata aaa tct aaa gct aac att ttt tat gct aaa aag gaa tga              1050
Ile Lys Ser Lys Ala Asn Ile Phe Tyr Ala Lys Lys Glu
            340                 345

<210> SEQ ID NO 45
<211> LENGTH: 349
<212> TYPE: PRT
<213> ORGANISM: Trichoplusia ni

<400> SEQUENCE: 45

Met Ala Val Met Ala Gln Thr Val Gln Glu Thr Ala Thr Val Leu Glu
1               5                   10                  15

Glu Glu Ala Arg Thr Val Thr Leu Val Ala Pro Lys Thr Thr Pro Arg
                20                  25                  30

Lys Tyr Lys Tyr Ile Tyr Thr Asn Phe Leu Thr Phe Ser Tyr Ala His
            35                  40                  45

Leu Ala Ala Leu Tyr Gly Leu Tyr Leu Cys Phe Thr Ser Ala Lys Trp
        50                  55                  60

Glu Thr Leu Leu Phe Ser Phe Val Leu Phe His Met Ser Asn Ile Gly
65                  70                  75                  80

Ile Thr Ala Gly Ala His Arg Leu Trp Thr His Lys Thr Phe Lys Ala
                85                  90                  95

Lys Leu Pro Leu Glu Ile Val Leu Met Ile Phe Asn Ser Leu Ala Phe
            100                 105                 110

Gln Asn Thr Ala Ile Thr Trp Ala Arg Glu His Arg Leu His His Lys
        115                 120                 125

Tyr Ser Asp Thr Asp Ala Asp Pro His Asn Ala Ser Arg Gly Phe Phe
    130                 135                 140

Tyr Ser His Val Gly Trp Leu Leu Val Lys Lys His Pro Asp Val Leu
145                 150                 155                 160

Lys Tyr Gly Lys Thr Ile Asp Met Ser Asp Val Tyr Asn Asn Pro Val
                165                 170                 175

Leu Lys Phe Gln Lys Lys Tyr Ala Val Pro Leu Ile Gly Thr Val Cys
            180                 185                 190

Phe Ala Leu Pro Thr Leu Ile Pro Val Tyr Cys Trp Gly Glu Ser Trp
        195                 200                 205

Asn Asn Ala Trp His Ile Ala Leu Phe Arg Tyr Ile Phe Asn Leu Asn
    210                 215                 220

Val Thr Phe Leu Val Asn Ser Ala Ala His Ile Trp Gly Asn Lys Pro
```

```
                    225                 230                 235                 240

Tyr Asp Lys Ser Ile Leu Pro Ala Gln Asn Leu Leu Val Ser Phe Leu
                245                 250                 255

Ala Ser Gly Glu Gly Phe His Asn Tyr His His Val Phe Pro Trp Asp
            260                 265                 270

Tyr Arg Thr Ala Glu Leu Gly Asn Asn Phe Leu Asn Leu Thr Thr Leu
        275                 280                 285

Phe Ile Asp Phe Cys Ala Trp Phe Gly Trp Ala Tyr Asp Leu Lys Ser
    290                 295                 300

Val Ser Glu Asp Ile Ile Lys Gln Arg Ala Lys Arg Thr Gly Asp Gly
305                 310                 315                 320

Ser Ser Gly Val Ile Trp Gly Trp Asp Asp Lys Asp Met Asp Arg Asp
                325                 330                 335

Ile Lys Ser Lys Ala Asn Ile Phe Tyr Ala Lys Lys Glu
            340                 345

<210> SEQ ID NO 46
<211> LENGTH: 2235
<212> TYPE: DNA
<213> ORGANISM: Saccharomyces cerevisiae
<220> FEATURE:
<221> NAME/KEY: CDS
<222> LOCATION: (1)..(2235)
<223> OTHER INFORMATION: FAA2

<400> SEQUENCE: 46
```

| | | | | | | | | | | | | | | | | |
|---|---|---|---|---|---|---|---|---|---|---|---|---|---|---|---|---|
| atg | gcc | gct | cca | gat | tat | gca | ctt | acc | gat | tta | att | gaa | tcg | gat | cct | 48 |
| Met | Ala | Ala | Pro | Asp | Tyr | Ala | Leu | Thr | Asp | Leu | Ile | Glu | Ser | Asp | Pro | |
| 1 | | | | 5 | | | | | 10 | | | | | 15 | | |
| cgt | ttc | gaa | agt | ttg | aag | aca | aga | tta | gcc | ggt | tac | acc | aaa | ggc | tct | 96 |
| Arg | Phe | Glu | Ser | Leu | Lys | Thr | Arg | Leu | Ala | Gly | Tyr | Thr | Lys | Gly | Ser | |
| | | | 20 | | | | | 25 | | | | | 30 | | | |
| gat | gaa | tat | att | gaa | gag | cta | tac | tct | caa | tta | cca | ctg | acc | agc | tac | 144 |
| Asp | Glu | Tyr | Ile | Glu | Glu | Leu | Tyr | Ser | Gln | Leu | Pro | Leu | Thr | Ser | Tyr | |
| | | 35 | | | | | 40 | | | | | 45 | | | | |
| ccc | agg | tac | aaa | aca | ttt | tta | aag | aaa | cag | gcg | gtt | gcc | att | tcg | aat | 192 |
| Pro | Arg | Tyr | Lys | Thr | Phe | Leu | Lys | Lys | Gln | Ala | Val | Ala | Ile | Ser | Asn | |
| | 50 | | | | | 55 | | | | | 60 | | | | | |
| ccg | gat | aat | gaa | gct | ggt | ttt | agc | tcg | att | tat | agg | agt | tct | ctt | tct | 240 |
| Pro | Asp | Asn | Glu | Ala | Gly | Phe | Ser | Ser | Ile | Tyr | Arg | Ser | Ser | Leu | Ser | |
| 65 | | | | 70 | | | | | 75 | | | | | 80 | | |
| tct | gaa | aat | cta | gtg | agc | tgt | gtg | gat | aaa | aac | tta | aga | act | gca | tac | 288 |
| Ser | Glu | Asn | Leu | Val | Ser | Cys | Val | Asp | Lys | Asn | Leu | Arg | Thr | Ala | Tyr | |
| | | | | 85 | | | | | 90 | | | | | 95 | | |
| gat | cac | ttc | atg | ttt | tct | gca | agg | aga | tgg | cct | caa | cgt | gac | tgt | tta | 336 |
| Asp | His | Phe | Met | Phe | Ser | Ala | Arg | Arg | Trp | Pro | Gln | Arg | Asp | Cys | Leu | |
| | | | 100 | | | | | 105 | | | | | 110 | | | |
| ggt | tca | agg | cca | att | gat | aaa | gcc | aca | ggc | acc | tgg | gag | gaa | aca | ttc | 384 |
| Gly | Ser | Arg | Pro | Ile | Asp | Lys | Ala | Thr | Gly | Thr | Trp | Glu | Glu | Thr | Phe | |
| | | 115 | | | | | 120 | | | | | 125 | | | | |
| cgt | ttc | gag | tcg | tac | tcc | acg | gta | tct | aaa | aga | tgt | cat | aat | atc | gga | 432 |
| Arg | Phe | Glu | Ser | Tyr | Ser | Thr | Val | Ser | Lys | Arg | Cys | His | Asn | Ile | Gly | |
| | 130 | | | | | 135 | | | | | 140 | | | | | |
| agt | ggt | ata | ttg | tct | ttg | gta | aac | acg | aaa | agg | aaa | cgt | cct | ttg | gaa | 480 |
| Ser | Gly | Ile | Leu | Ser | Leu | Val | Asn | Thr | Lys | Arg | Lys | Arg | Pro | Leu | Glu | |
| 145 | | | | 150 | | | | | 155 | | | | | 160 | | |
| gcc | aat | gat | ttt | gtt | gtt | gct | atc | tta | tca | cac | aac | aac | cct | gaa | tgg | 528 |
| Ala | Asn | Asp | Phe | Val | Val | Ala | Ile | Leu | Ser | His | Asn | Asn | Pro | Glu | Trp | |
| | | | | 165 | | | | | 170 | | | | | 175 | | |

```
atc cta aca gat ttg gcc tgt cag gcc tat tct cta act aac acg gct    576
Ile Leu Thr Asp Leu Ala Cys Gln Ala Tyr Ser Leu Thr Asn Thr Ala
            180                 185                 190 ttg tac gaa aca tta ggt cca aac acc tcc gag tac ata ttg aat tta    624
Leu Tyr Glu Thr Leu Gly Pro Asn Thr Ser Glu Tyr Ile Leu Asn Leu
        195                 200                 205 acc gag gcc ccc att ctg att ttt gca aaa tca aat atg tat cat gta    672
Thr Glu Ala Pro Ile Leu Ile Phe Ala Lys Ser Asn Met Tyr His Val
    210                 215                 220 ttg aag atg gtg cct gat atg aaa ttt gtt aat act ttg gtt tgt atg    720
Leu Lys Met Val Pro Asp Met Lys Phe Val Asn Thr Leu Val Cys Met
225                 230                 235                 240 gat gaa tta act cat gac gag ctc cgt atg cta aat gaa tcg ttg cta    768
Asp Glu Leu Thr His Asp Glu Leu Arg Met Leu Asn Glu Ser Leu Leu
            245                 250                 255 ccc gtt aag tgc aac tct ctc aat gaa aaa atc aca ttt ttt tca ttg    816
Pro Val Lys Cys Asn Ser Leu Asn Glu Lys Ile Thr Phe Phe Ser Leu
        260                 265                 270 gag cag gta gaa caa gtt ggt tgc ttt aac aaa att cct gca att cca    864
Glu Gln Val Glu Gln Val Gly Cys Phe Asn Lys Ile Pro Ala Ile Pro
    275                 280                 285 cct acc cca gat tcc ttg tat act att tcg ttt act tct ggt act aca    912
Pro Thr Pro Asp Ser Leu Tyr Thr Ile Ser Phe Thr Ser Gly Thr Thr
290                 295                 300 ggt tta cct aaa ggt gtg gaa atg tct cac aga aac att gcg tct ggg    960
Gly Leu Pro Lys Gly Val Glu Met Ser His Arg Asn Ile Ala Ser Gly
305                 310                 315                 320 ata gca ttt gct ttt tct acc ttc aga ata ccg cca gat aaa aga aac    1008
Ile Ala Phe Ala Phe Ser Thr Phe Arg Ile Pro Pro Asp Lys Arg Asn
            325                 330                 335 caa cag tta tat gat atg tgt ttt ttg cca ttg gct cat att ttt gaa    1056
Gln Gln Leu Tyr Asp Met Cys Phe Leu Pro Leu Ala His Ile Phe Glu
        340                 345                 350 aga atg gtt att gcg tat gat cta gcc atc ggg ttt gga ata ggc ttc    1104
Arg Met Val Ile Ala Tyr Asp Leu Ala Ile Gly Phe Gly Ile Gly Phe
    355                 360                 365 tta cat aaa cca gac cca act gta ttg gta gag gat ttg aag att ttg    1152
Leu His Lys Pro Asp Pro Thr Val Leu Val Glu Asp Leu Lys Ile Leu
370                 375                 380 aaa cct tac gcg gtt gcc ctg gtt cct aga ata tta aca cgg ttt gaa    1200
Lys Pro Tyr Ala Val Ala Leu Val Pro Arg Ile Leu Thr Arg Phe Glu
385                 390                 395                 400 gcc ggt ata aaa aat gct ttg gat aaa tcg act gtc cag agg aac gta    1248
Ala Gly Ile Lys Asn Ala Leu Asp Lys Ser Thr Val Gln Arg Asn Val
            405                 410                 415 gca aat act ata ttg gat tct aaa tcg gcc aga ttt acc gca aga ggt    1296
Ala Asn Thr Ile Leu Asp Ser Lys Ser Ala Arg Phe Thr Ala Arg Gly
        420                 425                 430 ggt cca gat aaa tcg att atg aat ttt cta gtt tat cat cgc gta ttg    1344
Gly Pro Asp Lys Ser Ile Met Asn Phe Leu Val Tyr His Arg Val Leu
    435                 440                 445 att gat aaa atc aga gac tct tta ggt ttg tcc aat aac tcg ttt ata    1392
Ile Asp Lys Ile Arg Asp Ser Leu Gly Leu Ser Asn Asn Ser Phe Ile
450                 455                 460 att acc gga tca gct ccc ata tct aaa gat acc tta cta ttt tta aga    1440
Ile Thr Gly Ser Ala Pro Ile Ser Lys Asp Thr Leu Leu Phe Leu Arg
465                 470                 475                 480 agc gcc ttg gat att ggt ata aga cag ggc tac ggc tta act gaa act    1488
Ser Ala Leu Asp Ile Gly Ile Arg Gln Gly Tyr Gly Leu Thr Glu Thr
            485                 490                 495
```

| | | | | | | | | | | | | | | |
|---|---|---|---|---|---|---|---|---|---|---|---|---|---|---|
| ttt | gct | ggt | gtc | tgt | tta | agc | gaa | ccg | ttt | gaa | aaa | gat | gtc | gga | tct | 1536 |
| Phe | Ala | Gly | Val | Cys | Leu | Ser | Glu | Pro | Phe | Glu | Lys | Asp | Val | Gly | Ser | |
| | | | 500 | | | | | 505 | | | | | 510 | | | |

```
ttt gct ggt gtc tgt tta agc gaa ccg ttt gaa aaa gat gtc gga tct      1536
Phe Ala Gly Val Cys Leu Ser Glu Pro Phe Glu Lys Asp Val Gly Ser
            500                 505                 510 tgt ggt gcc ata ggt att tct gca gaa tgt aga ttg aag tct gtt cca      1584
Cys Gly Ala Ile Gly Ile Ser Ala Glu Cys Arg Leu Lys Ser Val Pro
            515                 520                 525 gaa atg ggt tac cat gcc gac aag gat tta aaa ggt gaa ctg caa att      1632
Glu Met Gly Tyr His Ala Asp Lys Asp Leu Lys Gly Glu Leu Gln Ile
530                 535                 540 cgt ggc cca cag gtt ttt gaa aga tat ttt aaa aat ccg aat gaa act      1680
Arg Gly Pro Gln Val Phe Glu Arg Tyr Phe Lys Asn Pro Asn Glu Thr
545                 550                 555                 560 tca aaa gcc gtt gac caa gat ggt tgg ttt tcc acg gga gat gtt gca      1728
Ser Lys Ala Val Asp Gln Asp Gly Trp Phe Ser Thr Gly Asp Val Ala
            565                 570                 575 ttt atc gat gca aaa ggt cgc atc agc gtc att gat cga gtc aag aac      1776
Phe Ile Asp Ala Lys Gly Arg Ile Ser Val Ile Asp Arg Val Lys Asn
            580                 585                 590 ttt ttc aag cta gca cat ggt gaa tat att gct cca gag aaa atc gaa      1824
Phe Phe Lys Leu Ala His Gly Glu Tyr Ile Ala Pro Glu Lys Ile Glu
        595                 600                 605 aat att tat tta tca tca tgc ccc tat atc acg caa ata ttt gtc ttt      1872
Asn Ile Tyr Leu Ser Ser Cys Pro Tyr Ile Thr Gln Ile Phe Val Phe
610                 615                 620 gga gat cct ttg aag aca ttt tta gtt ggc atc gtt ggt gtt gat gtt      1920
Gly Asp Pro Leu Lys Thr Phe Leu Val Gly Ile Val Gly Val Asp Val
625                 630                 635                 640 gat gca gcg caa ccg att tta gct gca aag cac cca gag gtg aaa acg      1968
Asp Ala Ala Gln Pro Ile Leu Ala Ala Lys His Pro Glu Val Lys Thr
                645                 650                 655 tgg act aag gaa gtg cta gta gaa aac tta aat cgt aat aaa aag cta      2016
Trp Thr Lys Glu Val Leu Val Glu Asn Leu Asn Arg Asn Lys Lys Leu
            660                 665                 670 agg aag gaa ttt tta aac aaa att aat aaa tgc atc gat ggg cta caa      2064
Arg Lys Glu Phe Leu Asn Lys Ile Asn Lys Cys Ile Asp Gly Leu Gln
        675                 680                 685 gga ttt gaa aaa ttg cac aac atc aaa gtc gga ctt gag cct ttg act      2112
Gly Phe Glu Lys Leu His Asn Ile Lys Val Gly Leu Glu Pro Leu Thr
690                 695                 700 ctc gag gat gat gtt gtg acg cca act ttt aaa ata aag cgt gcc aaa      2160
Leu Glu Asp Asp Val Val Thr Pro Thr Phe Lys Ile Lys Arg Ala Lys
705                 710                 715                 720 gca tca aaa ttc ttc aaa gat aca tta gac caa cta tac gcc gaa ggt      2208
Ala Ser Lys Phe Phe Lys Asp Thr Leu Asp Gln Leu Tyr Ala Glu Gly
                725                 730                 735 tca cta gtc aag aca gaa aag ctt tag                                  2235
Ser Leu Val Lys Thr Glu Lys Leu
            740

<210> SEQ ID NO 47
<211> LENGTH: 744
<212> TYPE: PRT
<213> ORGANISM: Saccharomyces cerevisiae

<400> SEQUENCE: 47

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
            20                  25                  30
```

```
Asp Glu Tyr Ile Glu Glu Leu Tyr Ser Gln Leu Pro Leu Thr Ser Tyr
             35                  40                  45

Pro Arg Tyr Lys Thr Phe Leu Lys Lys Gln Ala Val Ala Ile Ser Asn
 50                  55                  60

Pro Asp Asn Glu Ala Gly Phe Ser Ser Ile Tyr Arg Ser Ser Leu Ser
 65                  70                  75                  80

Ser Glu Asn Leu Val Ser Cys Val Asp Lys Asn Leu Arg Thr Ala Tyr
                 85                  90                  95

Asp His Phe Met Phe Ser Ala Arg Arg Trp Pro Gln Arg Asp Cys Leu
                100                 105                 110

Gly Ser Arg Pro Ile Asp Lys Ala Thr Gly Thr Trp Glu Glu Thr Phe
            115                 120                 125

Arg Phe Glu Ser Tyr Ser Thr Val Ser Lys Arg Cys His Asn Ile Gly
            130                 135                 140

Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
            195                 200                 205

Thr Glu Ala Pro Ile Leu Ile Phe Ala Lys Ser Asn Met Tyr His Val
210                 215                 220

Leu Lys Met Val Pro Asp Met Lys Phe Val Asn Thr Leu Val Cys Met
225                 230                 235                 240

Asp Glu Leu Thr His Asp Glu Leu Arg Met Leu Asn Glu Ser Leu Leu
                245                 250                 255

Pro Val Lys Cys Asn Ser Leu Asn Glu Lys Ile Thr Phe Phe Ser Leu
                260                 265                 270

Glu Gln Val Glu Gln Val Gly Cys Phe Asn Lys Ile Pro Ala Ile Pro
            275                 280                 285

Pro Thr Pro Asp Ser Leu Tyr Thr Ile Ser Phe Thr Ser Gly Thr Thr
            290                 295                 300

Gly Leu Pro Lys Gly Val Glu Met Ser His Arg Asn Ile Ala Ser Gly
305                 310                 315                 320

Ile Ala Phe Ala Phe Ser Thr Phe Arg Ile Pro Asp Lys Arg Asn
                325                 330                 335

Gln Gln Leu Tyr Asp Met Cys Phe Leu Pro Leu Ala His Ile Phe Glu
            340                 345                 350

Arg Met Val Ile Ala Tyr Asp Leu Ala Ile Gly Phe Gly Ile Gly Phe
            355                 360                 365

Leu His Lys Pro Asp Pro Thr Val Leu Val Glu Asp Leu Lys Ile Leu
            370                 375                 380

Lys Pro Tyr Ala Val Ala Leu Val Pro Arg Ile Leu Thr Arg Phe Glu
385                 390                 395                 400

Ala Gly Ile Lys Asn Ala Leu Asp Lys Ser Thr Val Gln Arg Asn Val
                405                 410                 415

Ala Asn Thr Ile Leu Asp Ser Lys Ser Ala Arg Phe Thr Ala Arg Gly
                420                 425                 430

Gly Pro Asp Lys Ser Ile Met Asn Phe Leu Val Tyr His Arg Val Leu
            435                 440                 445

Ile Asp Lys Ile Arg Asp Ser Leu Gly Leu Ser Asn Asn Ser Phe Ile
```

450                 455                 460
Ile Thr Gly Ser Ala Pro Ile Ser Lys Asp Thr Leu Leu Phe Leu Arg
465                 470                 475                 480

Ser Ala Leu Asp Ile Gly Ile Arg Gln Gly Tyr Gly Leu Thr Glu Thr
                485                 490                 495

Phe Ala Gly Val Cys Leu Ser Glu Pro Phe Glu Lys Asp Val Gly Ser
                500                 505                 510

Cys Gly Ala Ile Gly Ile Ser Ala Glu Cys Arg Leu Lys Ser Val Pro
                515                 520                 525

Glu Met Gly Tyr His Ala Asp Lys Asp Leu Lys Gly Glu Leu Gln Ile
                530                 535                 540

Arg Gly Pro Gln Val Phe Glu Arg Tyr Phe Lys Asn Pro Asn Glu Thr
545                 550                 555                 560

Ser Lys Ala Val Asp Gln Asp Gly Trp Phe Ser Thr Gly Asp Val Ala
                565                 570                 575

Phe Ile Asp Ala Lys Gly Arg Ile Ser Val Ile Asp Arg Val Lys Asn
                580                 585                 590

Phe Phe Lys Leu Ala His Gly Glu Tyr Ile Ala Pro Glu Lys Ile Glu
                595                 600                 605

Asn Ile Tyr Leu Ser Ser Cys Pro Tyr Ile Thr Gln Ile Phe Val Phe
                610                 615                 620

Gly Asp Pro Leu Lys Thr Phe Leu Val Gly Ile Val Gly Val Asp Val
625                 630                 635                 640

Asp Ala Ala Gln Pro Ile Leu Ala Ala Lys His Pro Glu Val Lys Thr
                645                 650                 655

Trp Thr Lys Glu Val Leu Val Glu Asn Leu Asn Arg Asn Lys Lys Leu
                660                 665                 670

Arg Lys Glu Phe Leu Asn Lys Ile Asn Lys Cys Ile Asp Gly Leu Gln
                675                 680                 685

Gly Phe Glu Lys Leu His Asn Ile Lys Val Gly Leu Glu Pro Leu Thr
                690                 695                 700

Leu Glu Asp Asp Val Val Thr Pro Thr Phe Lys Ile Lys Arg Ala Lys
705                 710                 715                 720

Ala Ser Lys Phe Phe Lys Asp Thr Leu Asp Gln Leu Tyr Ala Glu Gly
                725                 730                 735

Ser Leu Val Lys Thr Glu Lys Leu
                740

<210> SEQ ID NO 48
<211> LENGTH: 25
<212> TYPE: DNA
<213> ORGANISM: Artificial sequence
<220> FEATURE:
<223> OTHER INFORMATION: Artificial sequence
<220> FEATURE:
<221> NAME/KEY: primer_bind
<222> LOCATION: (1)..(25)
<223> OTHER INFORMATION: PR-14126 (Ased11_U1_fw)

<400> SEQUENCE: 48
agtgcaggua aaacaatggc tcaag                                         25

<210> SEQ ID NO 49
<211> LENGTH: 22
<212> TYPE: DNA
<213> ORGANISM: Artificial sequence
<220> FEATURE:
<223> OTHER INFORMATION: Artificial sequence

```
<220> FEATURE:
<221> NAME/KEY: primer_bind
<222> LOCATION: (1)..(22)
<223> OTHER INFORMATION: PR-14127 (Ased11_U1_rev)

<400> SEQUENCE: 49
cgtgcgautt agttgtcctt cc                                              22

<210> SEQ ID NO 50
<211> LENGTH: 25
<212> TYPE: DNA
<213> ORGANISM: Artificial sequence
<220> FEATURE:
<223> OTHER INFORMATION: Artificial sequence
<220> FEATURE:
<221> NAME/KEY: primer_bind
<222> LOCATION: (1)..(25)
<223> OTHER INFORMATION: PR-14128 (Sld11_U1_fw)

<400> SEQUENCE: 50
agtgcaggua aaacaatggc tcaat                                           25

<210> SEQ ID NO 51
<211> LENGTH: 21
<212> TYPE: DNA
<213> ORGANISM: Artificial sequence
<220> FEATURE:
<223> OTHER INFORMATION: Artificial sequence
<220> FEATURE:
<221> NAME/KEY: primer_bind
<222> LOCATION: (1)..(21)
<223> OTHER INFORMATION: PR-14129 (Sld11_U1_rev)

<400> SEQUENCE: 51
cgtgcgautc attcaccctt a                                               21

<210> SEQ ID NO 52
<211> LENGTH: 27
<212> TYPE: DNA
<213> ORGANISM: Artificial sequence
<220> FEATURE:
<223> OTHER INFORMATION: Artificial sequence
<220> FEATURE:
<221> NAME/KEY: primer_bind
<222> LOCATION: (1)..(27)
<223> OTHER INFORMATION: PR-14130 (Tnd11_U1_fw)

<400> SEQUENCE: 52
agtgcaggua aaacaatggc tgttatg                                         27

<210> SEQ ID NO 53
<211> LENGTH: 30
<212> TYPE: DNA
<213> ORGANISM: Artificial sequence
<220> FEATURE:
<223> OTHER INFORMATION: Artificial sequence
<220> FEATURE:
<221> NAME/KEY: primer_bind
<222> LOCATION: (1)..(30)
<223> OTHER INFORMATION: PR-14131 (Tnd11_U1_rev)

<400> SEQUENCE: 53
cgtgcgautc attctttctt agcgtagaaa                                      30
```